United States Patent
Vorac et al.

(10) Patent No.: US 11,479,168 B2
(45) Date of Patent: Oct. 25, 2022

(54) VEHICLE INTERIOR COMPONENT

(71) Applicant: Shanghai Yanfeng Jinqiao Automotive Trim Systems Co. Ltd., Novi, MI (US)

(72) Inventors: Shane M. Vorac, Caledonia, MI (US); Michael John Thomas, Ann Arbor, MI (US)

(73) Assignee: SHANGHAI YANFENG JINQIAO AUTOMOTIVE TRIM SYSTEMS CO. LTD., Novi, MI (US)

( * ) Notice: Subject to any disclaimer, the term of this patent is extended or adjusted under 35 U.S.C. 154(b) by 0 days.

(21) Appl. No.: 17/570,703

(22) Filed: Jan. 7, 2022

(65) Prior Publication Data
US 2022/0126750 A1 Apr. 28, 2022

Related U.S. Application Data

(63) Continuation of application No. PCT/US2021/038532, filed on Jun. 22, 2021.
(Continued)

(51) Int. Cl.
*B60Q 3/68* (2017.01)
*A61L 2/10* (2006.01)
(Continued)

(52) U.S. Cl.
CPC .................. *B60Q 3/68* (2017.02); *A61L 2/10* (2013.01); *B60Q 3/225* (2017.02); *B60Q 3/62* (2017.02);
(Continued)

(58) Field of Classification Search
None
See application file for complete search history.

(56) References Cited

U.S. PATENT DOCUMENTS

| 733,343 A | 7/1903 | Strong |
| 2,248,618 A | 7/1941 | Fischer |

(Continued)

FOREIGN PATENT DOCUMENTS

| CN | 106955368 A | 7/2017 |
| CN | 107218169 A | 9/2017 |

(Continued)

OTHER PUBLICATIONS

Extended European Search Report from the European Patent Office for EP Patent Application No. 18899964.3 dated Aug. 25, 2021, 9 Pages.

(Continued)

*Primary Examiner* — Daniel S Larkin
(74) *Attorney, Agent, or Firm* — Amin, Turocy & Watson, LLP

(57) ABSTRACT

A system/component for a vehicle interior configured to administer a dose of radiation to an object is disclosed. The system/component may comprise a base providing a compartment, a cover, a module comprising a radiation source and a control panel providing a user interface. The radiation source may administer radiation to the object; the user interface may be configured for operation of the module; the user interface may provide a signal; the signal may comprise an audible signal and/or a light signal. The radiation source may comprise an ultraviolet light source. The system may be operated according to a control program. The compartment may contain the object and the light source may comprise an LED arrangement to direct light onto the object in the compartment. The dose of radiation may be intended to sanitize biomatter. A method of operating the system/component is also disclosed.

19 Claims, 28 Drawing Sheets

Related U.S. Application Data

(60) Provisional application No. 63/168,833, filed on Mar. 31, 2021, provisional application No. 63/043,475, filed on Jun. 24, 2020.

(51) Int. Cl.

| | | |
|---|---|---|
| *B60Q 3/225* | (2017.01) | |
| *B60Q 3/82* | (2017.01) | |
| *B60Q 3/62* | (2017.01) | |
| *B60R 7/06* | (2006.01) | |

(52) U.S. Cl.
CPC .................. *B60Q 3/82* (2017.02); *B60R 7/06* (2013.01); *A61L 2202/14* (2013.01)

(56) References Cited

U.S. PATENT DOCUMENTS

| | | |
|---|---|---|
| D133,214 S | 7/1942 | Ohm |
| D148,191 S | 12/1947 | Shuler et al. |
| 3,314,746 A | 4/1967 | Millar |
| 3,698,780 A | 10/1972 | Collins et al. |
| 4,710,634 A | 12/1987 | Brookes |
| 4,786,812 A | 11/1988 | Humphreys |
| 4,896,042 A | 1/1990 | Humphreys |
| 4,899,057 A | 2/1990 | Koji |
| 4,907,316 A | 3/1990 | Kurz |
| 4,952,369 A | 8/1990 | Belilos |
| 5,008,933 A | 4/1991 | Kao et al. |
| 5,124,131 A | 6/1992 | Wekhof |
| 5,126,572 A | 6/1992 | Chu |
| 5,379,201 A | 1/1995 | Friedman |
| 5,422,487 A | 6/1995 | Sauska et al. |
| 5,459,944 A | 10/1995 | Tatsutani et al. |
| 5,744,094 A | 4/1998 | Castberg et al. |
| 5,837,207 A | 11/1998 | Summers |
| 5,866,076 A | 2/1999 | Fencl et al. |
| 5,894,130 A | 4/1999 | Bach |
| 5,920,075 A | 7/1999 | Whitehead |
| D425,273 S | 5/2000 | Stephens et al. |
| RE36,896 E | 10/2000 | Maarschalkerweerd |
| 6,132,784 A | 10/2000 | Brandt et al. |
| 6,221,314 B1 | 4/2001 | Bigelow |
| 6,239,442 B1 | 5/2001 | Limura |
| 6,242,753 B1 | 6/2001 | Sakurai |
| 6,258,736 B1 | 7/2001 | Massholder |
| 6,278,122 B1 | 8/2001 | Gagnon |
| 6,301,359 B1 | 10/2001 | Roberts |
| 6,371,424 B1 | 4/2002 | Shaw |
| D457,667 S | 5/2002 | Piepgras et al. |
| 6,403,030 B1 | 6/2002 | Horton, III |
| 6,433,344 B1 | 8/2002 | Salisbury et al. |
| 6,447,720 B1 | 9/2002 | Horton, III et al. |
| 6,447,721 B1 | 9/2002 | Horton, III et al. |
| 6,458,331 B1 | 10/2002 | Roberts |
| 6,490,351 B1 | 12/2002 | Roberts |
| 6,524,529 B1 | 2/2003 | Horton, III |
| D475,154 S | 5/2003 | Binsukor |
| 6,566,659 B1 | 5/2003 | Clark et al. |
| 6,579,495 B1 | 6/2003 | Maiden |
| 6,592,816 B1 | 7/2003 | Ebel et al. |
| 6,614,039 B2 | 9/2003 | Hollander |
| D483,511 S | 12/2003 | Lay et al. |
| 6,656,424 B1 | 12/2003 | Deal |
| 6,670,626 B2 | 12/2003 | Witham et al. |
| 6,680,844 B2 | 1/2004 | Kim |
| 6,692,694 B1 | 2/2004 | Curry et al. |
| D487,527 S | 3/2004 | Sieczkowski |
| 6,720,626 B1 | 4/2004 | Igarashi |
| 6,752,627 B2 | 6/2004 | Lin |
| 6,756,598 B2 | 6/2004 | Berg et al. |
| 6,797,966 B2 | 9/2004 | Summers et al. |
| D500,884 S | 1/2005 | O'Rourke |
| 6,838,057 B2 | 1/2005 | Russell et al. |
| D506,279 S | 6/2005 | Sirichai et al. |
| 6,906,337 B2 | 6/2005 | Wedekamp |
| 6,939,397 B2 | 9/2005 | Nelsen et al. |
| 6,953,940 B2 | 10/2005 | Leighley et al. |
| D524,956 S | 7/2006 | Chan |
| 7,077,372 B2 | 7/2006 | Moran |
| 7,175,807 B1 | 2/2007 | Jones |
| 7,202,484 B1 | 4/2007 | Tantillo |
| D544,627 S | 6/2007 | Quintal |
| 7,227,534 B2 | 6/2007 | Lin et al. |
| 7,250,615 B1 | 7/2007 | Soong et al. |
| 7,261,264 B2 | 8/2007 | Moran |
| 7,332,124 B2 | 2/2008 | Trifu et al. |
| 7,372,044 B2 | 5/2008 | Ross |
| 7,407,624 B2 | 8/2008 | Cumberland et al. |
| 7,424,314 B2 | 9/2008 | Park |
| 7,427,763 B2 | 9/2008 | Rudkowski |
| 7,462,849 B2 | 12/2008 | Ferres et al. |
| 7,547,893 B1 | 6/2009 | Tantillo |
| 7,598,501 B2 | 10/2009 | Jones |
| 7,612,492 B2 | 11/2009 | Lestician |
| 7,692,159 B2 | 4/2010 | Lane et al. |
| 7,692,172 B2 | 4/2010 | Leben |
| 7,759,873 B2 | 7/2010 | Mastenbroeck et al. |
| 7,801,334 B2 | 9/2010 | Shin et al. |
| 7,820,101 B1 | 10/2010 | Esquivel, II |
| 7,834,335 B2 | 11/2010 | Harmon et al. |
| D630,364 S | 1/2011 | Schmitt et al. |
| 7,888,657 B1 | 2/2011 | Zadro |
| 7,960,706 B2 | 6/2011 | Ullman |
| 7,969,505 B2 | 6/2011 | Saito |
| 7,989,779 B1 | 8/2011 | Ray et al. |
| 8,084,752 B2 | 12/2011 | Ranta et al. |
| 8,087,737 B2 | 1/2012 | Shoenfeld |
| 8,105,532 B2 | 1/2012 | Harmon et al. |
| 8,110,819 B2 | 2/2012 | Boyarsky et al. |
| 8,114,346 B2 | 2/2012 | Hyde et al. |
| 8,161,596 B2 | 4/2012 | Cheung et al. |
| 8,168,903 B2 | 5/2012 | Chen |
| 8,168,963 B2 | 5/2012 | Ratcliffe |
| D662,250 S | 6/2012 | Wauters |
| 8,226,255 B2 | 7/2012 | Fan |
| 8,226,887 B2 | 7/2012 | Harmon et al. |
| 8,242,466 B2 | 8/2012 | Uber |
| D669,204 S | 10/2012 | Snell et al. |
| 8,277,724 B2 | 10/2012 | Jung et al. |
| 8,283,639 B2 | 10/2012 | Lane et al. |
| 8,297,435 B2 | 10/2012 | Lathem |
| 8,299,445 B2 | 10/2012 | Yamada et al. |
| D671,254 S | 11/2012 | Miyatake et al. |
| 8,330,121 B2 | 12/2012 | Douglas |
| 8,378,324 B2 | 2/2013 | Gardner, III |
| 8,399,854 B1 | 3/2013 | Crawford |
| 8,431,910 B1 | 4/2013 | Perry |
| 8,458,954 B2 | 6/2013 | Yamada et al. |
| D686,772 S | 7/2013 | Waltz et al. |
| 8,479,900 B2 | 7/2013 | Scicluna |
| 8,481,970 B2 | 7/2013 | Cooper et al. |
| 8,519,361 B2 | 8/2013 | Leben |
| 8,536,541 B2 | 9/2013 | Taylor et al. |
| 8,569,715 B1 | 10/2013 | Tantillo |
| D694,448 S | 11/2013 | Li |
| 8,575,567 B2 | 11/2013 | Lyslo et al. |
| 8,581,522 B2 | 11/2013 | Inskeep |
| 8,597,569 B2 | 12/2013 | Gruen et al. |
| 8,598,539 B2 | 12/2013 | Chuang |
| 8,606,981 B2 | 12/2013 | Engelhardt et al. |
| 8,624,203 B2 | 1/2014 | Tullo et al. |
| 8,680,496 B2 | 3/2014 | Leben |
| 8,696,985 B2 | 4/2014 | Gil et al. |
| 8,758,679 B2 | 6/2014 | Hyde et al. |
| D712,104 S | 8/2014 | Stickney et al. |
| 8,841,634 B2 | 9/2014 | Statham et al. |
| 8,841,970 B2 * | 9/2014 | Mehrabi .............. H03F 3/45 330/288 |
| 8,859,994 B2 | 10/2014 | Deal |
| 8,884,258 B1 | 11/2014 | Liao et al. |
| 8,895,939 B2 | 11/2014 | Lyslo et al. |
| D720,876 S | 1/2015 | Haverfield |
| 9,125,957 B2 | 9/2015 | Freue et al. |

(56) References Cited

U.S. PATENT DOCUMENTS

| | | |
|---|---|---|
| 9,138,499 B2 | 9/2015 | Bettles et al. |
| 9,144,617 B2 | 9/2015 | Deng |
| 9,144,618 B2 | 9/2015 | Kreitenberg |
| 9,233,179 B2 | 1/2016 | Ranta et al. |
| 9,242,018 B2 | 1/2016 | Cole et al. |
| D750,310 S | 2/2016 | Cole et al. |
| 9,358,313 B2 | 6/2016 | Deal |
| 9,370,600 B1 | 6/2016 | DuPuis et al. |
| 9,371,033 B2 | 6/2016 | Dellock et al. |
| 9,492,575 B2 | 11/2016 | Holub et al. |
| 9,517,280 B2 | 12/2016 | Lynn et al. |
| 9,526,215 B2 | 12/2016 | Suntych |
| 9,550,006 B2 | 1/2017 | Boodaghians et al. |
| 9,583,968 B2 * | 2/2017 | Salter .................. H02J 50/10 |
| 9,662,410 B2 | 5/2017 | Mackin |
| 9,687,575 B2 | 6/2017 | Farren |
| 9,700,642 B2 | 7/2017 | Neister |
| 9,782,504 B2 | 10/2017 | Holub et al. |
| 9,855,353 B1 | 1/2018 | Stacy |
| 9,901,652 B2 | 2/2018 | Cole et al. |
| 9,907,870 B2 | 3/2018 | Boodaghians et al. |
| 9,974,873 B2 | 5/2018 | Cole |
| 9,993,571 B2 | 6/2018 | Lin et al. |
| 10,052,395 B1 | 8/2018 | Salter et al. |
| 10,052,396 B2 | 8/2018 | Salter et al. |
| 10,145,055 B1 | 12/2018 | Harlan et al. |
| 10,272,166 B2 | 4/2019 | Mackin |
| 10,363,326 B2 | 7/2019 | Dellock et al. |
| 10,413,622 B2 | 9/2019 | Mackin |
| 10,534,895 B2 | 1/2020 | Ambrose et al. |
| 10,661,719 B2 | 5/2020 | McCarthy et al. |
| 10,906,074 B1 * | 2/2021 | Salter .................. B08B 7/0057 |
| 2001/0042842 A1 | 11/2001 | Leighley et al. |
| 2002/0005834 A1 | 1/2002 | Oh |
| 2002/0085947 A1 | 7/2002 | Deal |
| 2002/0190171 A1 | 12/2002 | Stock |
| 2005/0236013 A1 | 10/2005 | Huston et al. |
| 2006/0097189 A1 | 5/2006 | Lim |
| 2006/0120915 A1 | 6/2006 | Lewandowski |
| 2006/0158353 A1 | 7/2006 | Tseng |
| 2006/0188389 A1 | 8/2006 | Levy |
| 2006/0213792 A1 | 9/2006 | Nguyen et al. |
| 2006/0216193 A1 | 9/2006 | Johnson et al. |
| 2007/0023710 A1 | 2/2007 | Tom et al. |
| 2007/0053188 A1 | 3/2007 | New et al. |
| 2007/0071636 A1 | 3/2007 | Bovino et al. |
| 2007/0195550 A1 | 8/2007 | Tsai |
| 2007/0231192 A1 | 10/2007 | Jung et al. |
| 2007/0231193 A1 | 10/2007 | Jung et al. |
| 2007/0251812 A1 | 11/2007 | Hayman, Jr. |
| 2007/0258852 A1 | 11/2007 | Hootsmans et al. |
| 2008/0002049 A1 | 1/2008 | Saito |
| 2008/0008620 A1 | 1/2008 | Alexiadis |
| 2008/0067418 A1 | 3/2008 | Ross |
| 2008/0199354 A1 | 8/2008 | Gordon |
| 2008/0253941 A1 | 10/2008 | Wichers et al. |
| 2008/0267831 A1 | 10/2008 | Lee |
| 2009/0117001 A1 | 5/2009 | Hyde et al. |
| 2009/0123331 A1 | 5/2009 | Ross |
| 2009/0140891 A1 | 6/2009 | Ragusa et al. |
| 2009/0180934 A1 | 7/2009 | Khoshbin |
| 2009/0191100 A1 | 7/2009 | Deal |
| 2009/0212234 A1 | 8/2009 | Vestal |
| 2009/0218512 A1 | 9/2009 | Ranta et al. |
| 2009/0246073 A1 | 10/2009 | Murphy |
| 2009/0252646 A1 | 10/2009 | Holden et al. |
| 2009/0314308 A1 | 12/2009 | Kim et al. |
| 2009/0317436 A1 | 12/2009 | Wilson et al. |
| 2010/0104471 A1 | 4/2010 | Harmon et al. |
| 2010/0111775 A1 | 5/2010 | Hyde et al. |
| 2010/0126190 A1 | 5/2010 | Ha |
| 2010/0127189 A1 | 5/2010 | Boyarsky et al. |
| 2010/0127984 A1 | 5/2010 | Chen |
| 2011/0054574 A1 | 3/2011 | Felix |
| 2011/0158862 A1 | 6/2011 | Kim et al. |
| 2011/0174992 A1 | 7/2011 | Sakita |
| 2011/0215261 A1 | 9/2011 | Lyslo et al. |
| 2011/0256019 A1 | 10/2011 | Gruen et al. |
| 2011/0291995 A1 | 12/2011 | Shr et al. |
| 2012/0112100 A1 | 5/2012 | Lo |
| 2012/0121457 A1 | 5/2012 | Farren |
| 2012/0141322 A1 | 6/2012 | Fogg |
| 2012/0141323 A1 | 6/2012 | Fogg |
| 2012/0176241 A1 | 7/2012 | Pasch et al. |
| 2012/0187313 A1 | 7/2012 | Clark et al. |
| 2012/0221192 A1 | 8/2012 | Seibt |
| 2012/0227211 A1 | 9/2012 | Hwang et al. |
| 2012/0248332 A1 | 10/2012 | Kreitenberg et al. |
| 2012/0282135 A1 | 11/2012 | Trapani |
| 2012/0286038 A1 | 11/2012 | Wu |
| 2012/0305787 A1 | 12/2012 | Henson |
| 2012/0305804 A1 | 12/2012 | Goldman |
| 2013/0017122 A1 | 1/2013 | Jung et al. |
| 2013/0045132 A1 | 2/2013 | Tumanov |
| 2013/0062534 A1 | 3/2013 | Cole |
| 2013/0129567 A1 | 5/2013 | Gray |
| 2013/0240756 A1 | 9/2013 | Segal |
| 2013/0270446 A1 | 10/2013 | Dardona et al. |
| 2013/0330235 A1 | 12/2013 | Stibich et al. |
| 2013/0341533 A1 | 12/2013 | Leben |
| 2014/0048724 A1 | 2/2014 | Marshall |
| 2014/0059796 A1 | 3/2014 | Boodaghians et al. |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0061509 A1 | 3/2014 | Shur et al. |
| 2014/0091236 A1 | 4/2014 | Jhawar et al. |
| 2014/0131595 A1 | 5/2014 | Nathan et al. |
| 2014/0140888 A1 | 5/2014 | Neisler |
| 2014/0175280 A1 | 6/2014 | Tantillo |
| 2014/0241941 A1 | 8/2014 | Kreitenberg |
| 2014/0284499 A1 | 9/2014 | Schumacher |
| 2014/0301893 A1 | 10/2014 | Stroup et al. |
| 2014/0322073 A1 | 10/2014 | Link et al. |
| 2014/0336495 A1 | 11/2014 | Bittner |
| 2015/0028228 A1 | 1/2015 | Almasy et al. |
| 2015/0217011 A1 | 8/2015 | Bettles et al. |
| 2016/0089459 A1 | 3/2016 | Boodaghians et al. |
| 2016/0114067 A1 | 4/2016 | Dobrinsky et al. |
| 2016/0136314 A1 | 5/2016 | Kreitenberg |
| 2016/0204634 A1 | 7/2016 | Parlow et al. |
| 2016/0375165 A1 | 12/2016 | Cole et al. |
| 2017/0045807 A1 | 2/2017 | Ye |
| 2017/0202988 A1 | 7/2017 | Clark |
| 2017/0296686 A1 | 10/2017 | Cole |
| 2018/0064833 A1 | 3/2018 | Childress et al. |
| 2019/0022260 A1 | 1/2019 | Cole |
| 2019/0076558 A1 | 3/2019 | Zhang-Miske et al. |
| 2019/0126190 A1 | 5/2019 | Boulet et al. |
| 2019/0282718 A1 | 9/2019 | Cole |

FOREIGN PATENT DOCUMENTS

| | | |
|---|---|---|
| CN | 107791941 A | 3/2018 |
| CN | 107073282 B | 9/2020 |
| DE | 1 196 598 B | 7/1965 |
| DE | 199 61 991 A1 | 7/2001 |
| DE | 10 2009 040 765 A1 | 2/2011 |
| DE | 10 2016 110 547 A1 | 12/2016 |
| DE | 10 2015 115 029 A1 | 4/2017 |
| DE | 10 2017 113 179 A1 | 12/2017 |
| DE | 10 2018 002 328 A1 | 9/2019 |
| EP | 2 668 964 A1 | 12/2013 |
| EP | 2 809 358 A4 | 11/2015 |
| EP | 3 287 146 A1 | 2/2018 |
| EP | 3 061 465 B1 | 4/2018 |
| GB | 2527964 B | 3/2016 |
| JP | 2012-254673 A | 12/2012 |
| JP | 5197550 B2 | 5/2013 |
| KR | 0178167 B1 | 4/1999 |
| KR | 20-0400220 Y1 | 11/2005 |
| KR | 10-0685728 B1 | 2/2007 |
| KR | 10-0740903 B1 | 7/2007 |

(56) References Cited

FOREIGN PATENT DOCUMENTS

| | | |
|---|---|---|
| KR | 10-2008-9008502 A | 1/2008 |
| KR | 10-1241660 B1 | 3/2013 |
| KR | 10-1408941 B1 | 6/2014 |
| KR | 10-2014-0095356 A | 8/2014 |
| KR | 10-2015-0017544 A | 2/2015 |
| KR | 10-2015-0112079 A | 10/2015 |
| KR | 10-2015-0116800 A | 10/2015 |
| KR | 10-2015-0137293 A | 12/2015 |
| KR | 10-2016-0057215 A | 5/2016 |
| KR | 10-1640093 B1 | 7/2016 |
| KR | 10-2087940 B1 | 3/2020 |
| KR | 10-2176420 B1 | 11/2020 |
| WO | 2008/010684 A1 | 1/2008 |
| WO | 2010/060079 A1 | 5/2010 |
| WO | 2013/116566 A1 | 8/2013 |
| WO | 2015/012592 A1 | 1/2015 |
| WO | 2017/204774 A1 | 11/2017 |
| WO | 2018/030987 A1 | 2/2018 |
| WO | 2019/068189 A1 | 4/2019 |
| WO | 2019/139743 A1 | 7/2019 |
| WO | 2020/043485 A2 | 3/2020 |

OTHER PUBLICATIONS

International Search Report and Written Opinion received for PCT Application Serial No. PCT/US2018/66184 dated Mar. 25, 2019, 8 pages.

Wikipedia "Ultraviolet", Retrieved from https://en.wikipedia.org/w/index.php?title=Ultraviolet&oldid=810528029, Nov. 15, 2017, 33 pages.

International Search Report and Written Opinion received for PCT Application Serial No. PCT/US2021/38532 dated Nov. 12, 2021, 19 pages.

* cited by examiner

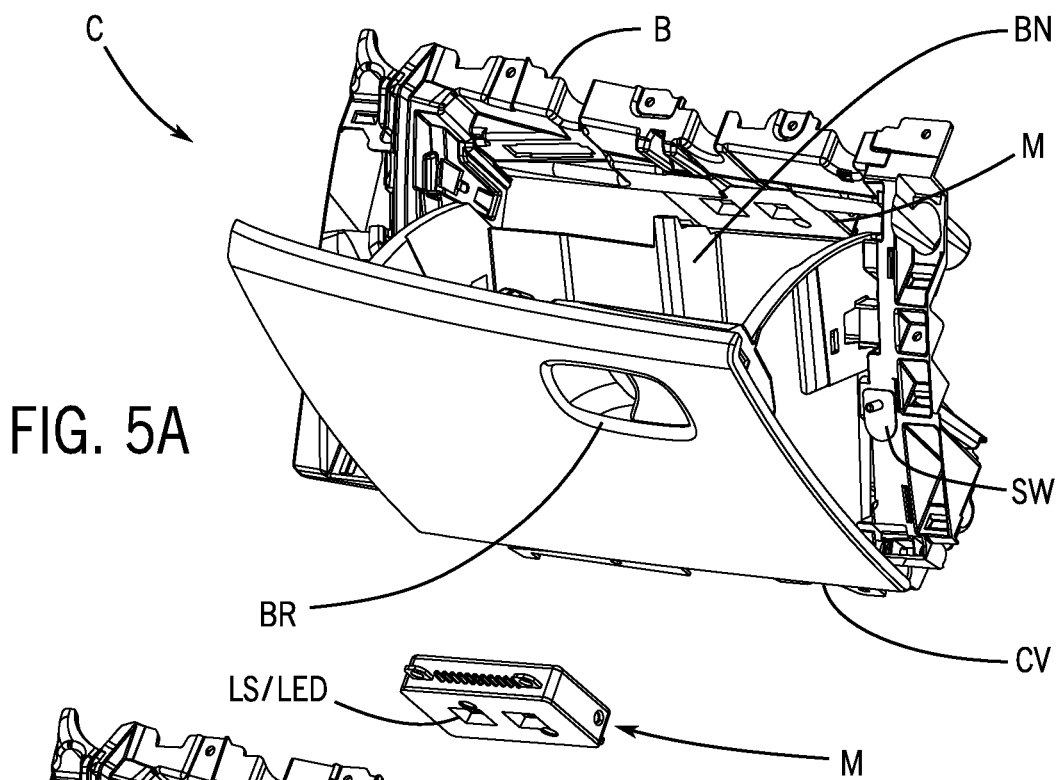
FIG. 5A
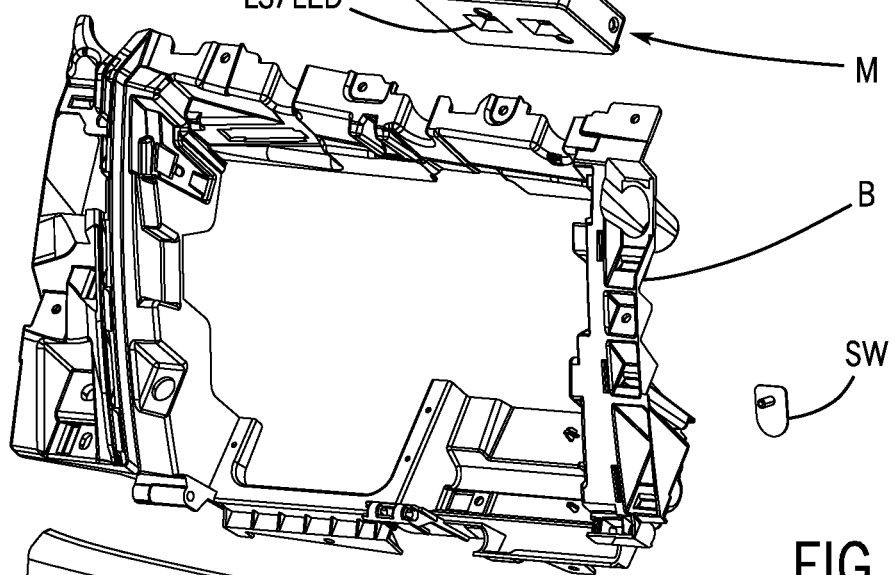
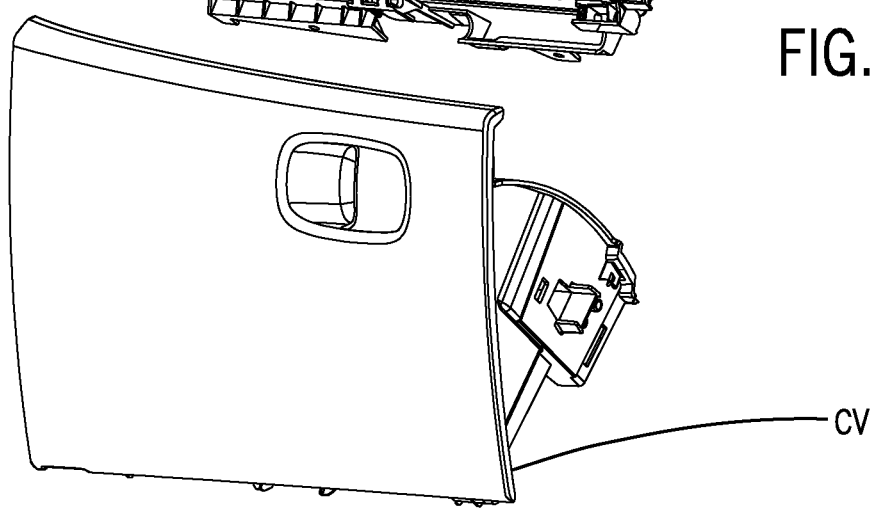
FIG. 5B

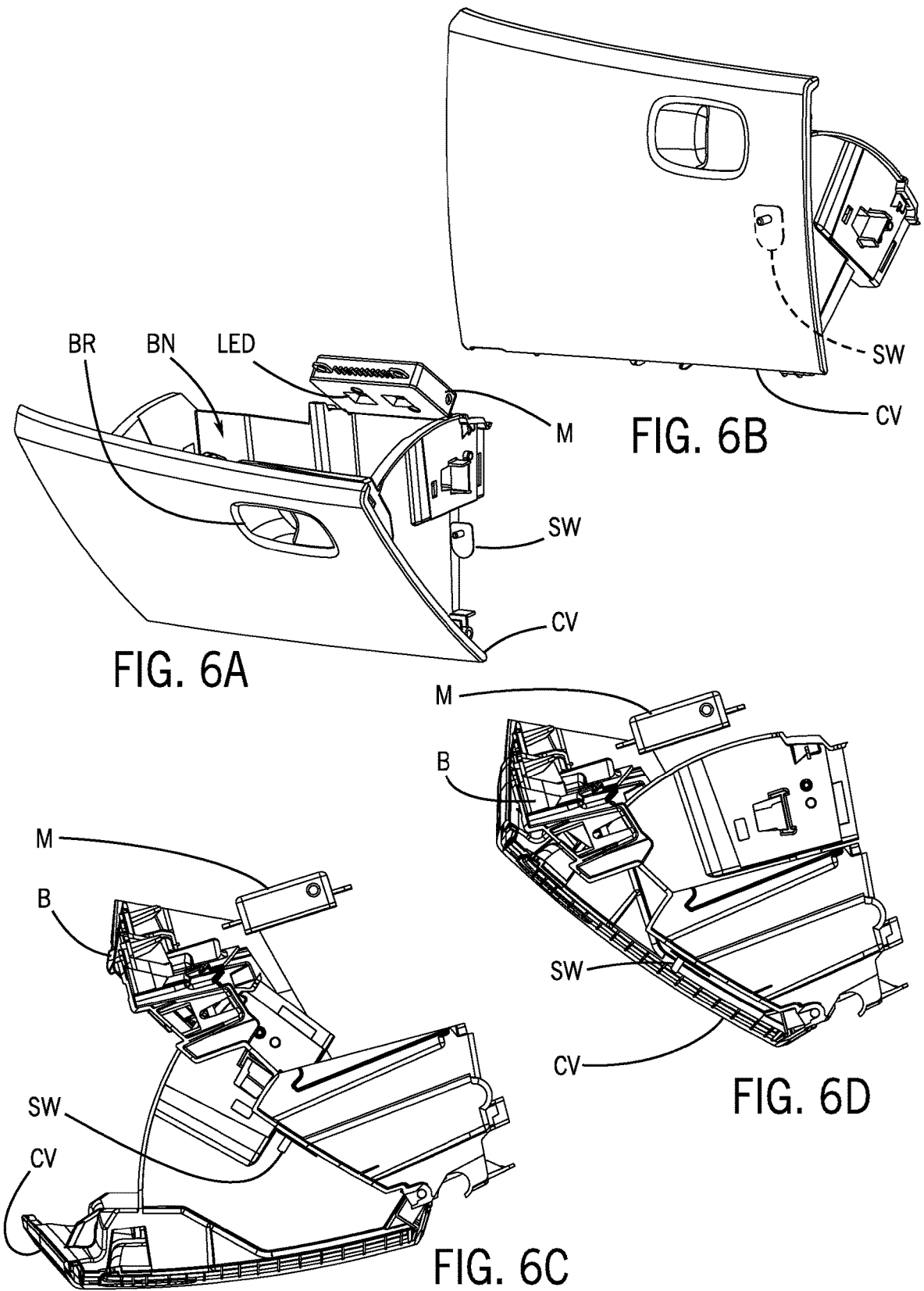

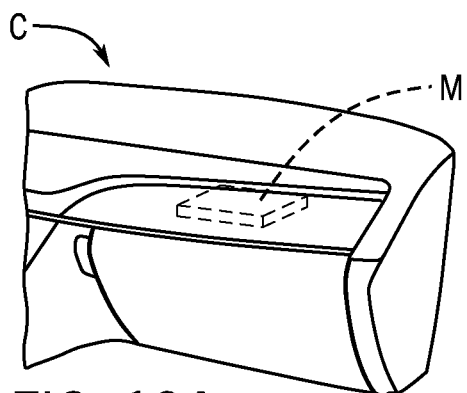
FIG. 13A
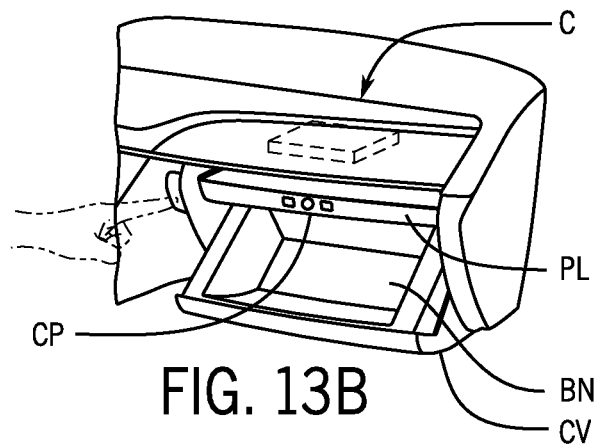
FIG. 13B
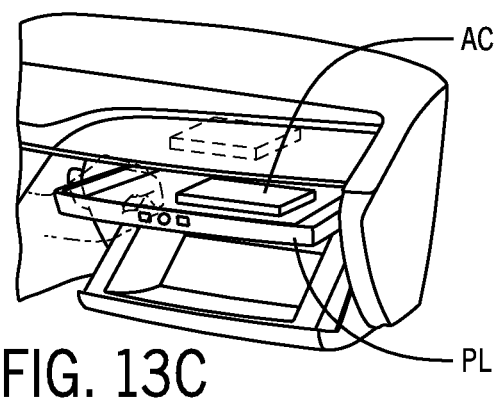
FIG. 13C
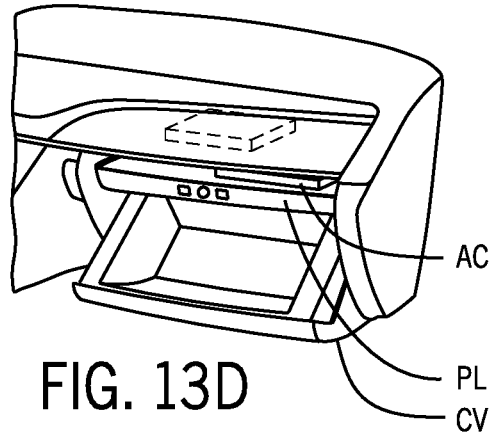
FIG. 13D
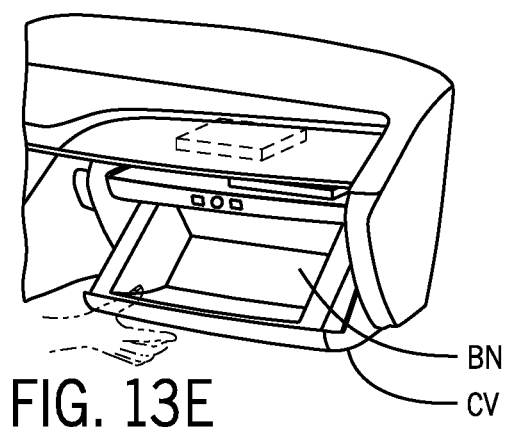
FIG. 13E
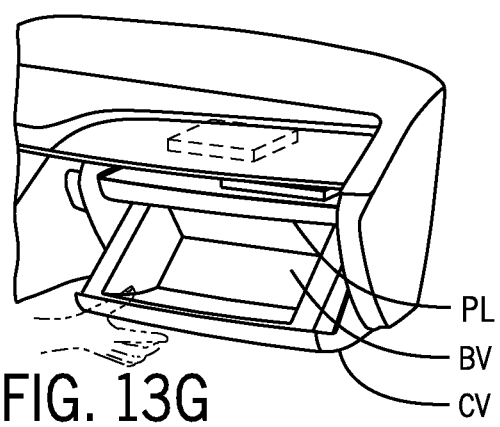
FIG. 13G
FIG. 13F

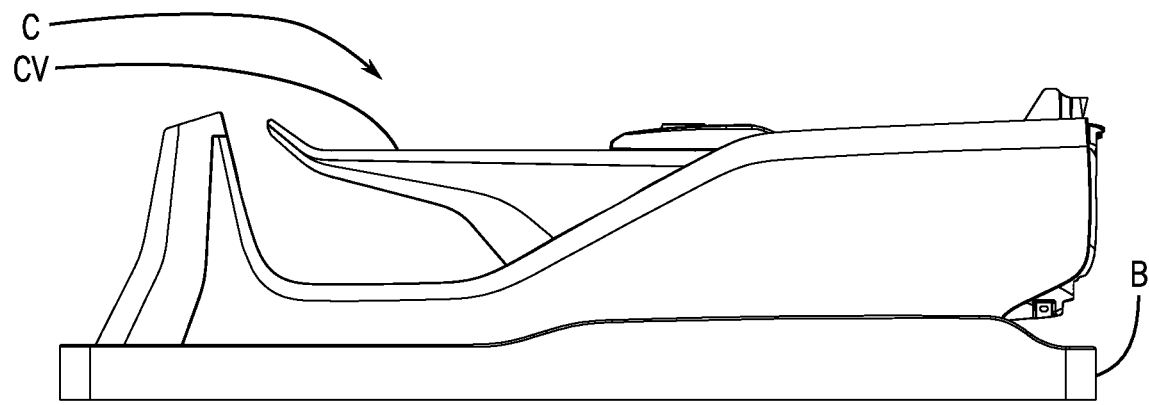
FIG. 28A
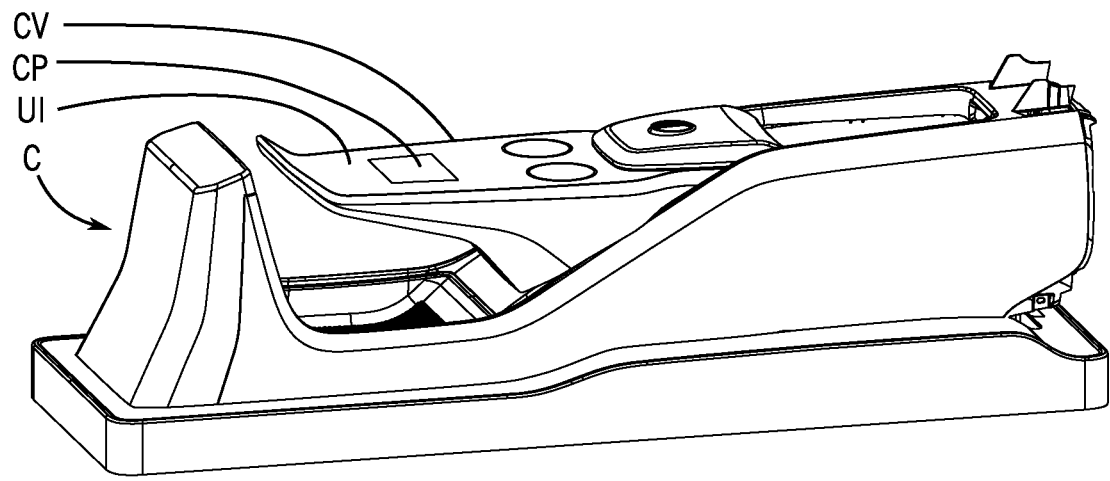
FIG. 28B
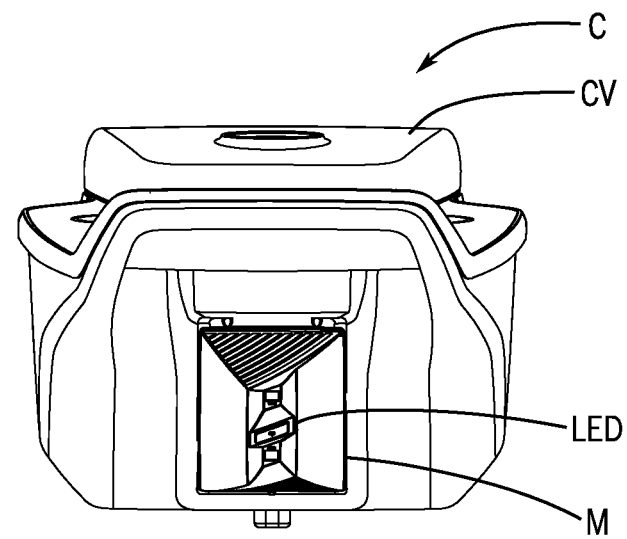
FIG. 28C
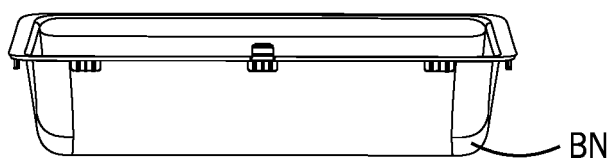

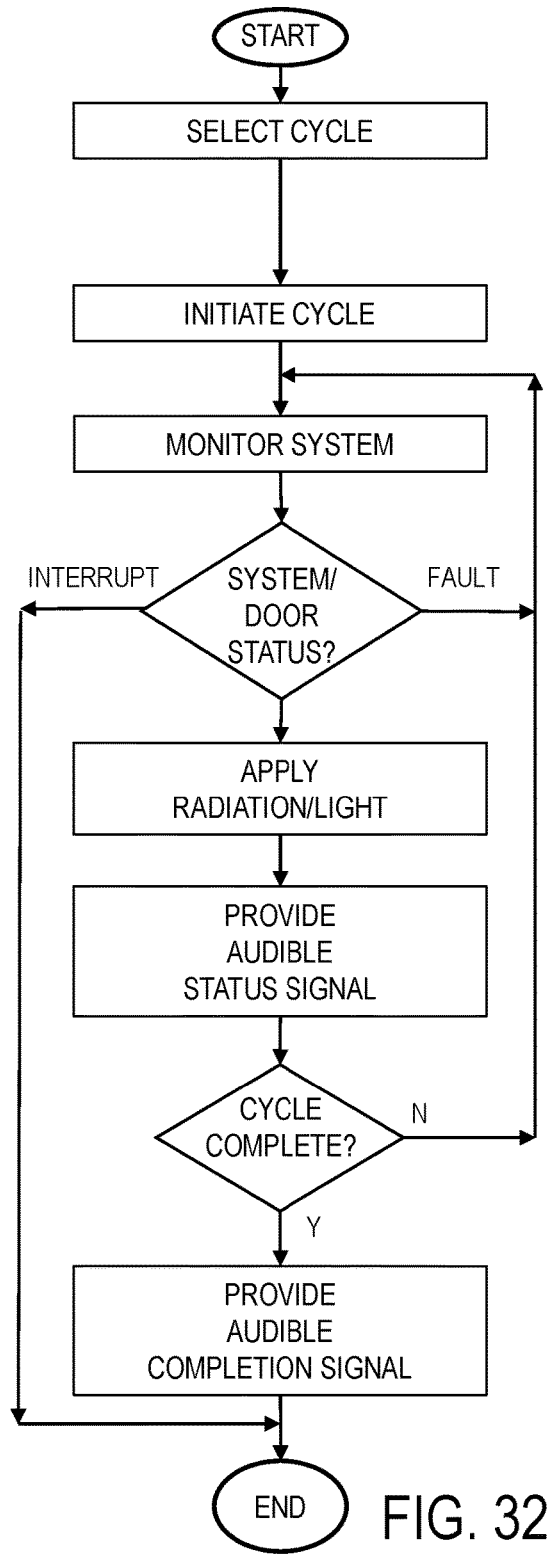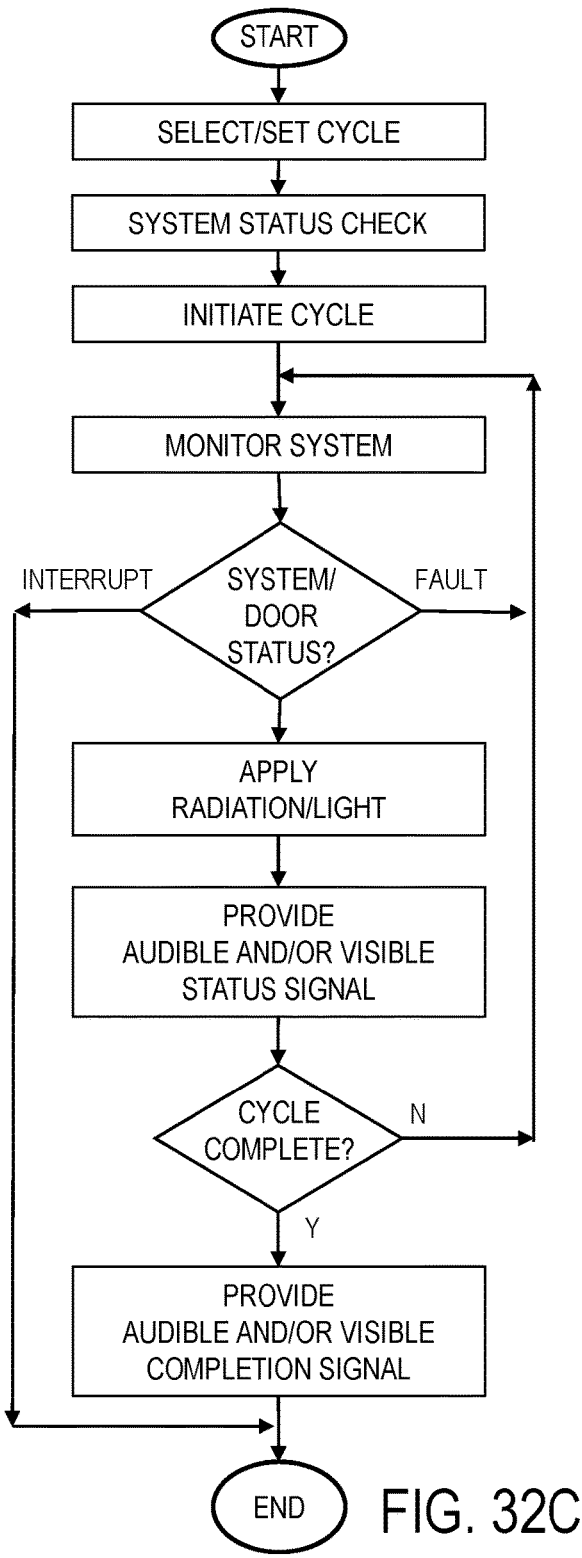
FIG. 32B
FIG. 32C

VEHICLE INTERIOR COMPONENT

CROSS-REFERENCE TO RELATED APPLICATIONS

The present application is a continuation of PCT/International Patent Application No. PCT/US2021/038532 titled "VEHICLE INTERIOR COMPONENT" filed Jun. 22, 2021, which claims the benefit of (a) U.S. Patent Application No. 63/043,475 titled "VEHICLE INTERIOR COMPONENT" filed Jun. 24, 2020 and (b) U.S. Patent Application No. 63/168,833 titled "VEHICLE INTERIOR COMPONENT" filed Mar. 31, 2021.

The present application claims priority to and incorporates by reference in full the following patent applications: (a) U.S. Patent Application No. 63/168,833 titled "VEHICLE INTERIOR COMPONENT" filed Mar. 31, 2021; (b) U.S. Patent Application No. 63/043,475 titled "VEHICLE INTERIOR COMPONENT" filed Jun. 24, 2020; (c) PCT/International Patent Application No. PCT/US2021/038532 titled "VEHICLE INTERIOR COMPONENT" filed Jun. 22, 2021.

The present application incorporates by reference in full the following patent applications: (a) PCT/International Patent Application No. PCT/US2018/012056 titled "VEHICLE INTERIOR COMPONENT" filed Jan. 2, 2018; (b) U.S. patent application Ser. No. 16/109,240 titled "VEHICLE INTERIOR COMPONENT" filed Aug. 22, 2018 (now U.S. Pat. No. 10,661,719); (c) PCT/International Patent Application No. PCT/US2018/066184 titled "SYSTEM FOR TREATMENT/IRRADIATION OF A SURFACE IN A VEHICLE INTERIOR" filed Dec. 18, 2018; (d) U.S. patent application Ser. No. 16/902,669 titled "SYSTEM AND METHOD FOR TREATMENT/IRRADIATION OF A SURFACE IN A VEHICLE INTERIOR" filed Jun. 16, 2020; (e) U.S. Patent Application No. 63/043,475 titled "VEHICLE INTERIOR COMPONENT" filed Jun. 24, 2020; (f) U.S. Patent Application No. 63/168,833 titled "VEHICLE INTERIOR COMPONENT" filed Mar. 31, 2021.

FIELD

The present invention relates to a vehicle interior component for treatment/radiation of an object/article in a vehicle interior.

The present invention relates to a system and method for treatment/radiation of an object/article in a vehicle interior.

BACKGROUND

It is known to treat an object/article with radiation such as from an ultraviolet light source.

It would be advantageous to provide an improved component; system; and/or method for treatment/radiation of an object/article in a vehicle interior.

SUMMARY

The present invention relates to a component for a vehicle interior configured to administer a dose of radiation to an object comprising a base comprising a compartment for the object, a cover moveable relative to the base from a closed position to an open position providing access to the compartment, a module comprising a radiation source and a user interface comprising a control panel for the module. The radiation source may be configured to administer the dose of radiation to the object in the compartment. The user interface may be configured to provide a signal comprising an audible signal and/or a light signal. The user interface may be presented by a light guide on the cover. The object may comprise biomatter; the dose of radiation may be intended to sanitize the object of biomatter. The component may comprise a sensor configured to detect whether the object is in the compartment. The compartment may be configured to contain the object; the radiation source may comprise an LED arrangement configured to direct light onto the object in the compartment. The radiation source may comprise a light source; the light source may comprise at least one of (a) an LED; (b) an LED lamp; (c) an LED array; (d) at least one LED; (e) a set of two LEDs; (f) a lamp installed within the base; (g) a light emitting diode installed within the base; (h) a UV-C LED installed within the base; (i) an LED arrangement; and/or (j) an ultraviolet light source. The light guide may comprise at least one of (a) a light guide aligned with the user interface; and/or (b) a light pipe aligned with the user interface.

The present invention relates to a system for a vehicle interior configured to administer a dose of radiation to an object comprising a component comprising a base providing a compartment and a cover, a module comprising a radiation source operated by a control program and a control panel configured to provide a user interface in operation of the module. The user interface may comprise presentation of a signal. The compartment may be configured to contain the object. The cover may be configured to move between a closed position and an open position to allow access within the compartment. The radiation source may be configured to administer the dose of radiation to the object according to the control program. The control panel may comprise an indicator light. The user interface may comprise a light transmissive light guide on the cover. The light guide may be aligned with the indicator light on the control panel when the cover is in the closed position. The compartment may comprise a bin; the radiation source may be configured to direct radiation into the bin. The system may comprise a control system for the module; the control system may be operated according to the control program on a cycle intended to administer a dose of ultraviolet light to the object. The cover may comprise a door; the control system for the module may be operated by a method comprising the steps of (a) opening the door; (b) placing the object; (c) closing the door; (d) administering the dose of light to the object; (e) opening the door; and (f) removing the object. The signal may comprise at least one of (a) a completion signal or (b) a fault signal or (c) an interrupt signal for the module. The signal may be provided by at least one of (a) an indicator; (b) a sound transmitter; (c) a light; and/or (d) light-transmissive elements to provide illumination. The cover may comprise a door for a glove box and the control program may be configured to turn off the radiation source if a switch detects that the door is open. The signal may comprise at least one of (a) a blinking light when in operation during administration of the dose of radiation or (b) a solid light when the dose of radiation is completed or (c) a light that is off when the module is not in operation. The signal may comprise at least one of (a) a sound during administration of the dose of radiation; (b) a sound to indicate completion of administration of the dose of radiation; (c) an alert in a fault condition; (d) an audible tone at an interval during administration of radiation; and/or (e) a pattern comprising a tone at an interval when in operation and a tone when completed. The system may comprise a tray configured to move between a retracted position and an extended position. The component may comprise at least one of a storage compartment; a glove box; a console; a floor console; an overhead console; a trim panel; a door panel; and/or a removable compartment. The system may be operated according to a method comprising the steps of setting a cycle of operation of the system, initiating the cycle of operation of the system, monitoring the system in operation and providing the signal at the user interface. Monitoring the system in operation may comprise determining status of the system; operation of the system may comprise at least one of applying the dose of radiation to the object or ending the cycle if a fault is detected. The signal may be provided to indicate status of the system. The component may comprise a sensor to indicate status and monitoring the system in operation may comprise monitoring status indicated by the sensor.

The present invention relates to a component for a vehicle interior configured to administer a dose of radiation to an object comprising a base comprising a compartment for the object, a cover moveable relative to the base from a closed position to an open position providing access to the compartment, a module comprising a radiation source, a user interface comprising a control panel for the module and a platform configured to position the object for access when the cover is in the open position. The radiation source may be configured to administer the dose of radiation to the object in the compartment. The user interface may be configured to provide a signal comprising an audible signal and/or a light signal. The dose of radiation may comprise a dose of ultraviolet light. The platform may be configured to position the object for administration of the dose of ultraviolet light when the cover is in the closed position. The radiation source may comprise an upper light source and a lower light source separated from the upper light source by the platform. The platform may comprise a mesh configured to facilitate passage of light from the lower light source to the object.

The present invention relates to a component for a vehicle interior configured to administer a dose of radiation to an object comprising a base comprising a compartment for the object, a cover moveable relative to the base from a closed position to an open position providing access to the compartment, a module comprising a radiation source and a user interface comprising a control panel for the module. The radiation source may be configured to administer the dose of radiation to the object in the compartment. The user interface may be configured to provide a signal comprising an audible signal and/or a light signal. The object may comprise biomatter; the dose of radiation may be intended to sanitize the object of biomatter. The component may comprise a sensor configured to detect whether the cover is in the closed position. The module may be configured to administer the dose of radiation only when the sensor detects that the cover is in the closed position. The component may comprise a sensor configured to detect whether the object is in the compartment. The control panel may comprise at least one of (a) an indicator light; (b) a speaker; and/or (c) a button. The control panel may be on the cover. The control panel may comprise a button adjacent to the cover. The control panel may be separate from the base. The control panel may comprise a remote button within the vehicle interior. The dose of radiation may be selected at the control panel. The component may comprise a control system for the module. The control system may be operated on a cycle intended to administer the dose of ultraviolet light to the object. The control system may be operable by a control program. The control program may be configured to provide a fault signal to stop operation of the radiation source when a fault condition is detected. A fault condition may be detected when at least one of (a) the object is not detected in the compartment; and/or (b) the cover is not detected in a closed position. The fault condition may be detected at a sensor. The compartment may be configured to contain the object; the radiation source may comprise an LED arrangement configured to direct light onto the object in the compartment. The radiation source may comprise an ultraviolet light source. The radiation source may comprise a light source; the light source may comprise at least one of (a) an LED; (b) an LED lamp; (c) an LED array; (d) at least one LED; (e) a set of two LEDs; (f) a lamp installed within the base; (g) a light emitting diode installed within the base; (h) a UV-C LED installed within the base; (i) an LED arrangement; and/or (j) an ultraviolet light source. The user interface may be configured for operation of the module; the user interface may comprise a light signal. The user interface may be presented by a light guide on the cover. The light guide may be aligned with an indicator light on the control panel when the cover is in the closed position. The compartment may comprise a removable bin for the object. The cover may comprise at least one of (a) a light guide aligned with the user interface; and/or (b) a light pipe aligned with the user interface. The cover may comprise a door; the control system for the module may be operated by a method comprising the steps of (a) opening the door; (b) placing the object; (c) closing the door; (d) administering the dose of light to the object; (e) opening the door; and (f) removing the object. The component may comprise a platform configured to position the object for access when the cover is in the open position; the dose of radiation may comprise a dose of ultraviolet light; the platform may be configured to position the object for administration of the dose of ultraviolet light when the cover is in the closed position. The radiation source may comprise an upper light source and a lower light source separated from the upper light source by the platform; the platform may comprise a mesh configured to facilitate passage of light from the lower light source to the object. The base may comprise at least one of (a) a platform for the object; (b) a shelf for the object; and/or (c) a first compartment for a first object and a second compartment for a second object. The base may be configured to be installed in an instrument panel. The base may be configured to be installed under an instrument panel. The component may comprise a glove box; the cover may comprise a door for the glove box. The component may comprise at least one of (a) a storage compartment; (b) a console; and/or (c) a removable compartment.

The present invention relates to a system for a vehicle interior configured to administer a dose of radiation to an object comprising a component comprising a base providing a compartment and a cover, a module comprising a radiation source operated by a control program, and a control panel configured to provide a user interface in operation of the module. The user interface may comprise presentation of a signal; the compartment may be configured to contain the object; the cover may be configured to move between a closed position and an open position to allow access within the compartment; and the radiation source may be configured to administer the dose of radiation to the object according to the control program. The radiation may comprise ultraviolet light; the radiation source may comprise an ultraviolet light source configured to administer the dose of ultraviolet light to the object. The user interface may be configured for operation of the module. The component may comprise a platform. The cover may be configured to be moved to the closed position for administration of the dose of radiation. The cover may be configured to be moved to the open position relative to the base providing access to the compartment. The compartment may comprise a bin; the radiation source may be configured to direct radiation into the bin. The control panel may comprise an indicator light; the user interface may comprise a light transmissive light guide on the cover; the light guide may be aligned with the indicator light on the control panel when the cover is in the closed position. The base may comprise the user interface; the cover may comprise at least one of (a) a light guide aligned with the user interface; and/or (b) a light pipe aligned with the user interface. The system may comprise a control system for the module; the control system may be operated according to the control program on a cycle intended to administer a dose of ultraviolet light to the object. The cover may comprise a door; the control system for the module may be operated by a method comprising the steps of (a) opening the door; (b) placing the object; (c) closing the door; (d) administering the dose of light to the object; (e) opening the door; and (f) removing the object. The signal of the user interface may comprise at least one of a light signal and/or an audible signal. The light signal may be provided at the control panel. The audible signal may be provided at the control panel. The control panel may comprise an operator control configured to operate the module of the component; the operator control may be configured to select an operation cycle for the module. The signal may comprise a completion signal. The signal may comprise at least one of (a) a fault signal; and/or (b) an interrupt signal for the module. The signal may be provided by at least one of (a) an indicator; (b) a sound transmitter; (c) a light; and/or (d) light-transmissive elements to provide illumination. The radiation source may comprise an LED arrangement configured to provide at least 100 mW of LED light. The LED light may comprise a wavelength of about 275 nm. The LED arrangement may comprise two LED lights; each LED light of the two LED lights may comprise an LED configured to provide at least 100 mA total UVC energy. The control program may be configured to operate the module with an operation cycle comprising a cycle time of between 15 seconds and 120 seconds. The compartment may be configured to place the object at about 15 cm from the radiation source. The radiation source may be configured to provide at least a 3 log reduction in virus/bacteria on the object. The radiation source may be configured to provide at least a 99 percent reduction in active biomatter on the object. The module may be configured to provide 100 mA of UVC power; the control program may be configured to operate the module with an operation cycle comprising a cycle time of about 120 seconds. The control panel may comprise an override switch. The component may comprise a glovebox comprising a switch configured to turn off the radiation source. The cover may comprise a door for the glove box and the control program may be configured to turn off the radiation source if the switch detects that the door is open. The control panel may comprise a push button to activate the module. The control panel may comprise a remote button to activate the module. The signal from the user interface may be configured to indicate of status of operation of the module. The signal may comprise a blinking light when in operation during administration of the dose of radiation and a solid light when the dose of radiation is completed. The signal may comprise a light that is off when the module is not in operation. The signal may comprise a sound during administration of the dose of radiation. The signal may comprise a sound to indicate completion of administration of the dose of radiation. The signal may comprise an alert in a fault condition. The signal may comprise an audible tone at an interval during administration of radiation. The signal may comprise a pattern comprising a tone at an interval when in operation and a tone when completed. The component may comprise at least one of a storage compartment; a glove box; a console; a floor console; an overhead console; a trim panel; and/or a door panel. The system may be operated according to a method comprising the steps of setting a cycle of operation of the system, initiating the cycle of operation of the system, monitoring the system in operation and providing the signal at the user interface. Monitoring the system in operation may comprise determining status of the system; operation of the system may comprise at least one of applying the dose of radiation to the object or ending the cycle if a fault is detected. The signal may be provided to indicate status of the system. The signal may comprise at least one of (a) a completion signal when the cycle of operation is completed; (b) an operation signal during operation of the system; and/or (c) a fault signal if the cycle of operation is not completed. The component may comprise a sensor to indicate status, and monitoring the system in operation may comprise monitoring status indicated by the sensor. Status of the system may comprise at least one of (a) presence of the object in the compartment; and/or (b) status of the cover. The cover may comprise a door movable from an open position to a closed position; status of the system may comprise detection of whether the door is in the open position of the door. When the door is in the open position of the door, the step of monitoring the system in operation may comprise indicating a fault status and providing a fault signal.

The present invention relates to a vehicle interior component configured to administer a dose of ultraviolet light from a module providing an ultraviolet light source directed to an object comprising a base, a tray coupled to the base and comprising a compartment, and a user interface. The ultraviolet light source may be configured to administer the dose of ultraviolet light to the object in the compartment; the user interface may be configured for operation of the module; the tray may be configured to move relative to the base from a retracted position for administration of the dose of ultraviolet light to an extended position for access. The component may comprise a mechanism configured to (a) retain the tray in the retracted position; and (b) guide movement of the tray from the retracted position to the extended position. The mechanism may be configured to move the tray from the retracted position to the extended position after administration of the dose of ultraviolet light. The mechanism may comprise (a) a latch configured to retain the tray in the retracted position and (b) an actuator configured to unlatch the tray after administration of the dose of ultraviolet light. The mechanism may comprise a motor configured to move the tray between the retracted position and the extended position; the motor may be configured to move the tray from the retracted position to the extended position after administration of the dose of ultraviolet light. The ultraviolet light source may comprise an upper lamp and a lower lamp separated from the upper lamp by the tray. The component may comprise a bin coupled to the base comprising a receptacle into which an article can be stowed and configured to move relative to the base in an opening direction from a closed position to an open position for access; the ultraviolet light source may be configured to administer a dose of ultraviolet light to the article in the receptacle. The component may comprise (a) a cover configured to cover the tray and the bin and (b) a mechanism; the mechanism may be configured to guide movement of the cover and the bin.

The tray may be configured to move between the retracted position and the extended position when the bin is in the closed position and the open position. The component may comprise a button; the mechanism may be configured to move the cover and the tray in response to actuation of the button. The component may comprise a control system for the module; the control system for the module may be operated by a method comprising the steps of (a) extending the tray, (b) placing the object, (c) retracting the tray, (d) administering the dose of light to the object, (e) extending the tray, and (f) removing the object.

The present invention relates to a component for a vehicle interior configured to stow an article comprising a base, a bin coupled to the base comprising a receptacle into which the article can be stowed and configured to move relative to the base in an opening direction from a closed position to an open position for access, a tray coupled to the base and configured to move relative to the base from a retracted position to an intermediate position for access, a cover coupled to the base configured to move from an upward position to cover the tray to a lowered position to uncover the tray and a module coupled to the base providing an ultraviolet light source configured to administer a dose of ultraviolet light to the article. The bin may be configured to move relative to the base from the closed position to the open position when the tray is in the retracted position and the intermediate position. The tray may be configured to move from the retracted position to the intermediate position when the bin is in the closed position and the open position. The tray may be configured to move relative to the base from the intermediate position to an extended position. The tray may be configured to move from the intermediate position to the extended position when the bin is in the closed position and the open position. The component may comprise a mechanism configured to (a) latch the tray to the base in the retracted position, and (b) unlatch the tray from the base. The component may comprise a mechanism configured to (a) retain the bin in the closed position (b) guide movement of the bin from the closed position to the open position and (c) guide movement of the cover from the upward position to the lowered position. The component may comprise a mechanism configured to (a) retain the tray in the retracted position and (b) move the tray from the retracted position to the intermediate position. The component may comprise a mechanism configured to (a) retain the tray in the retracted position and (b) guide movement of the tray from the retracted position to the intermediate position. The mechanism may be configured to move the tray from the retracted position to the intermediate position after administration of the dose of ultraviolet light. The component may comprise a user interface configured for operation of the module; at least one of (a) the base; and/or (b) the tray may comprise the user interface; the cover may comprise a light guide aligned with the user interface.

The present invention relates to a vehicle interior component configured to administer a dose of ultraviolet light from a module providing an ultraviolet light source directed to an object comprising a base configured to provide a compartment, a cover moveable from a closed position to an open position providing access to the compartment, a user interface and a platform for the object. The ultraviolet light source may be configured to administer the dose of ultraviolet light to the object in the compartment; the user interface may be configured for operation of the module; the platform may be configured to move with the cover between the closed position and the open position. The platform may be configured to position the object for access when the cover is in the open position; the platform may be configured to position the object for administration of the dose of ultraviolet light when the cover is in the closed position. The ultraviolet light source may comprise an upper light source and a lower light source separated from the upper light source by the platform; the platform may comprise a mesh configured to facilitate passage of light from the lower light source to the object. The cover may comprise a door; the control system for the module may be operated by a method comprising the steps of (a) opening the door, (b) placing the object, (c) closing the door, (d) administering the dose of light to the object, (e) opening the door, and (f) removing the object.

The present invention relates to a vehicle interior component configured to administer a dose of ultraviolet light from a module providing an ultraviolet light source directed to an object comprising a cover moveable from a closed position to an open position providing access to a compartment, a user interface and a platform for the object. The ultraviolet light source may be configured to administer the dose of ultraviolet light to the object; the user interface may be configured for operation of the module; the platform may be configured to move with the cover between the closed position and the open position. The platform may be configured to position the object for access when the cover is in the open position; the platform may be configured to position the object for administration of the dose of ultraviolet light when the cover is in the closed position. The cover may comprise a door; the control system for the module may be operated by a method comprising the steps of (a) opening the door, (b) placing the object, (c) closing the door, (d) administering the dose of light to the object, (e) opening the door, and (f) removing the object.

The present invention relates to a vehicle interior component configured to administer a dose of ultraviolet light from a module providing an ultraviolet light source directed to an object comprising a cover moveable from a closed position to an open position providing access to a compartment; a user interface; and a platform for the object. The ultraviolet light source may be configured to administer the dose of ultraviolet light to the object. The user interface may be configured for operation of the module. The platform may be configured to move with the cover between the closed position and the open position. The component may comprise a base configured to provide the compartment. The base may comprise a control panel for the user interface; the control panel may comprise an indicator light; the user interface may comprise a light transmissive light guide on the cover; the light guide may be aligned with the indicator light on the control panel when the cover is in the closed position. The base may comprise the user interface; the cover may comprise at least one of (a) a light guide aligned with the user interface; and/or (b) a light pipe aligned with the user interface. The ultraviolet light source may comprise at least one of (a) an LED; (b) an LED lamp; (c) an LED array; (d) at least one LED; (e) a set of two LEDs; (f) a lamp installed within the base; (g) a light emitting diode installed within the base; and/or (h) a UV-C LED installed within the base. The base may comprise the platform for the object. The ultraviolet light source may comprise a lamp installed within the base. The module may be mounted in the base. The base may be configured to be installed in/under an instrument panel. The component may comprise a control panel for the user interface; the control panel may comprise a button. The component may comprise a glove box; the cover may comprise a door for the glove box. The platform may be configured to position the object for access when the cover is in the open position; the platform may be configured to position the object for administration of the dose of ultraviolet light when the cover is in the closed position. The ultraviolet light source may comprise an upper light source and a lower light source separated from the upper light source by the platform; the platform may comprise a mesh configured to facilitate passage of light from the lower light source to the object. The user interface may comprise a control panel. The platform may comprise a shelf. The platform may comprise a first compartment for a first object and a second compartment for a second object. The component may comprise a harness for the cover; the cover may comprise the user interface. The component may comprise a glove box. The component may comprise a control system for the module; the control system may be operated on a cycle intended to administer a dose of ultraviolet light to the object. The cover may comprise a door. The control system for the module may be operated by a method comprising the steps of (a) opening the door; (b) placing the object; (c) closing the door; (d) administering the dose of light to the object; (e) opening the door; and (f) removing the object. The object may comprise biomatter; the dose of ultraviolet light may be intended to sanitize the object of biomatter.

The present invention relates to a vehicle interior component configured to administer a dose of ultraviolet light from a module providing an ultraviolet light source directed to an object comprising a base; a tray coupled to the base and comprising a compartment; and a user interface. The ultraviolet light source may be configured to administer the dose of ultraviolet light to the object in the compartment. The user interface may be configured for operation of the module. The tray may be configured to move relative to the base from a retracted position for administration of the dose of ultraviolet light to an extended position for access. The component may comprise a mechanism configured to (a) retain the tray in the retracted position (b) guide movement of the tray from the retracted position to the extended position. The mechanism may be configured to move the tray from the retracted position to the extended position after administration of the dose of ultraviolet light. The mechanism may comprise (a) a latch configured to retain the tray in the retracted position and (b) an actuator configured to unlatch the tray after administration of the dose of ultraviolet light. The latch may comprise a push-push latch. The mechanism may be configured to move the tray from the retracted position to the extended position in response to an external force applied to the tray. The mechanism may comprise a motor configured to move the tray between the retracted position and the extended position; the motor may be configured to move the tray from the retracted position to the extended position after administration of the dose of ultraviolet light. The ultraviolet light source may comprise an upper lamp and a lower lamp separated from the upper lamp by the tray. The tray may comprise a mesh configured to facilitate passage of light from the lower lamp to the article. The component may comprise a cover coupled to the base; the cover may be configured to move from (a) an upward position to cover the tray to (b) a lowered position to uncover the tray. The cover may be configured to prevent movement of the tray when the cover is in the upward position; the cover may be configured to allow movement of the tray when the cover is in the lowered position. The component may comprise a harness for the cover; the cover may comprise the user interface. At least one of (a) the base; and/or (b) the tray may comprise the user interface; the cover may comprise a light guide aligned with the user interface. The component may comprise a bin coupled to the base comprising a receptacle into which an article can be stowed and configured to move relative to the base in an opening direction from a closed position to an open position for access; the ultraviolet light source may be configured to administer a dose of ultraviolet light to the article in the receptacle. The component may comprise (a) a cover configured to cover the tray and the bin and (b) a mechanism; the mechanism may be configured to guide movement of the cover and the bin. The mechanism may comprise (a) a latch configured to retain the bin in the closed position and (b) a gear and a rack configured to guide movement of the cover and the bin. The tray may be configured to move between the retracted position and the extended position when the bin is in the closed position and the open position. The component may comprise a button; the mechanism may be configured to move the cover and the tray in response to actuation of the button. The component may comprise a first button and a second button. The first button may be configured to (a) move the cover relative to the bin from the upward position to the lowered position to uncover the tray and (b) move the tray relative to the base from the retracted position to the intermediate/extended position for access. The first button may be configured to move the tray relative to the base from the retracted position to the intermediate/extended position for access when the first button is pressed after the second button. The second button may be configured to move the bin relative to the base from the closed position to the open position for access. The second button may be configured to (a) move the cover from the upward position to the lowered position and (b) move the bin relative to the base from the closed position to the open position for access. The ultraviolet light source may comprise at least one of (a) a lamp installed within the base; (b) a light emitting diode installed within the base; and/or (c) a UV-C LED installed within the base. The module may be mounted in the base. The component may comprise a platform in the base for the object. The user interface may comprise a control panel. The component may comprise a control system for the module. The control system may be operated on a cycle intended to administer a dose of ultraviolet light to the object. The control system for the module may be operated by a method comprising the steps of (a) extending the tray; (b) placing the object; (c) retracting the tray; (d) administering the dose of light to the object; (e) extending the tray; and (f) removing the object. The component may comprise a glove box. The base may be configured to be installed in/under an instrument panel. The object may comprise biomatter; the dose of ultraviolet light may be intended to sanitize the object of biomatter.

The present invention relates to a component for a vehicle interior configured to stow an article comprising a base; a bin coupled to the base comprising a receptacle into which the article can be stowed and configured to move relative to the base in an opening direction from a closed position to an open position for access; a tray coupled to the base and configured to move relative to the base from a retracted position to an intermediate/extended position for access; a cover coupled to the base configured to move from an upward position to cover the tray to a lowered position to uncover the tray; and a module coupled to the base providing an ultraviolet light source. The bin may be configured to move relative to the base from the closed position to the open position when the tray is in the retracted position and the intermediate/extended position. The ultraviolet light source may be configured to administer a dose of ultraviolet light to the article. The tray may be configured to move from the retracted position to the intermediate/extended position when the bin is in the closed position and the open position. The tray may be configured to move relative to the base from the intermediate/extended position to an extended position. The component may comprise a spring SG; the spring may be configured to move the tray from the extended position to the intermediate/extended position. The tray may be configured to move from the intermediate/extended position to the extended position when the bin is in the closed position and the open position. The component may comprise a mechanism configured to (a) latch the tray to the base in the retracted position and (b) unlatch the tray from the base. The component may comprise a mechanism configured to (a) retain the bin in the closed position (b) guide movement of the bin from the closed position to the open position and (c) guide movement of the cover from the upward position to the lowered position. The component may comprise a mechanism configured to (a) retain the tray in the retracted position and (b) move the tray from the retracted position to the intermediate/extended position. The component may comprise a mechanism configured to (a) retain the tray in the retracted position (b) guide movement of the tray from the retracted position to the intermediate/extended position. The mechanism may be configured to move the tray from the retracted position to the intermediate/extended position after administration of the dose of ultraviolet light. The component may comprise a user interface configured for operation of the module. At least one of (a) the base; and/or (b) the tray may comprise the user interface; the cover may comprise a light guide aligned with the user interface. The component may comprise a harness for the cover; the cover may comprise the user interface.

The present invention relates to a vehicle interior component configured to administer a dose of ultraviolet light from a module providing an ultraviolet light source directed to an object comprising a base configured to provide the compartment; a cover moveable from a closed position to an open position providing access to the compartment; a user interface; and a platform for the object. The ultraviolet light source may be configured to administer the dose of ultraviolet light to the object in the compartment. The user interface may be configured for operation of the module. The platform may be configured to move with the cover between the closed position and the open position. The platform may be configured to position the object for access when the cover is in the open position; the platform may be configured to position the object for administration of the dose of ultraviolet light when the cover is in the closed position. The ultraviolet light source may comprise an upper light source and a lower light source separated from the upper light source by the platform; the platform may comprise a mesh configured to facilitate passage of light from the lower light source to the object. The ultraviolet light source may comprise a lamp installed within the base. The module may be mounted in the base. The user interface may comprise a control panel. The platform may comprise a shelf. The platform may comprise a first compartment for a first object and a second compartment for a second object. The component may comprise a harness for the cover; the cover may comprise the user interface. The component may comprise a glove box. The base may be configured to be installed in/under an instrument panel. The component may comprise a control system for the module; the control system may be operated on a cycle intended to administer a dose of ultraviolet light to the object. The cover may comprise a door. The control system for the module may be operated by a method comprising the steps of (a) opening the door; (b) placing the object; (c) closing the door; (d) administering the dose of light to the object; (e) opening the door; and (f) removing the object. The object may comprise biomatter; the dose of ultraviolet light may be intended to sanitize the object of biomatter. The base may comprise the user interface; the cover may comprise at least one of (a) a light guide aligned with the user interface; and/or (b) a light pipe aligned with the user interface.

The present invention relates to a component for a vehicle interior configured to administer a dose of light from a module providing a light source directed to an object comprising a base configured to provide a compartment; a cover for the base; a control panel configured to provide a user interface; the light source may be configured to administer the dose of light to the object; the user interface may be configured for operation of the module. The dose of light may comprise ultraviolet radiation; the cover may be moveable from a closed position to an open position relative to base. The component may comprise a sensor configured to detect whether the cover may be in the closed position. The compartment may be configured to contain the object and the light source may comprise an LED arrangement configured to direct light onto the object in the compartment. The module may comprise the LED arrangement. The component may comprise a sensor configured to detect whether an object may be in the compartment. The user interface may be configured to provide a signal; the signal may comprise an audible signal and/or a light signal. The component may comprise a storage compartment, a console, a removable compartment. The control panel may be on the cover; the control panel may be separate from the base; the control panel may comprise a remote button within the vehicle interior.

The present invention relates to a component for a vehicle interior configured to administer a dose of radiation to an object comprising a base configured to provide a compartment; a cover for the base; a module comprising radiation source; a control panel for the module configured to provide a user interface; the radiation source may be configured to administer the dose of radiation to the object; the user interface may be configured for operation of the module; the user interface may be configured to provide a signal; the signal may comprise an audible signal and/or a light signal. The radiation source may comprise a light source. The light source may comprise ultraviolet light source. The compartment may be configured to contain the object and the light source may comprise an LED arrangement configured to direct light onto the object in the compartment. The cover may be moveable from a closed position to an open position relative to the base providing access to the compartment. The component may comprise a sensor configured to detect whether the cover may be in the closed position. The module may be configured to administer the dose of radiation only when the sensor detects that the cover may be in the closed position. The compartment may comprise a removable bin for the object. The control panel for the user interface may comprise an indicator light. The control panel for the user interface may comprise a speaker. The control panel for the user interface may comprise a button. The control panel for the user interface may comprise a button adjacent to the cover. The user interface may comprise a light signal. The user interface may be presented by a transmissive light guide on the cover; the light guide may be aligned with an indicator light on the control panel when the cover may be in a closed position. The cover may comprise at least one of (a) a light guide aligned with the user interface; and/or (b) a light pipe aligned with the user interface. The radiation source may comprise an ultraviolet light source; the ultraviolet light source may comprise at least one of (a) an LED; (b) an LED lamp; (c) an LED array; (d) at least one LED; (e) a set of two LEDs; (f) a lamp installed within the base; (g) a light emitting diode installed within the base; and/or (h) a UV-C LED installed within the base. The ultraviolet light source may comprise a lamp installed within the base. The module may be mounted in the base. The base may be configured to be installed in/under an instrument panel. The control panel may comprise a button. The component may comprise a glove box; the cover may comprise a door for the glove box. The component may comprise a platform configured to position the object for access when the cover may be in the open position; the platform may be configured to position the object for administration of the dose of ultraviolet light when the cover may be in the closed position. The ultraviolet light source may comprise an upper light source and a lower light source separated from the upper light source by the platform; the platform may comprise a mesh configured to facilitate passage of light from the lower light source to the object. The base may comprise a platform for the object; the platform may comprise a shelf; the platform may comprise a first compartment for a first object and a second compartment for a second object. The component may comprise a storage compartment comprising the platform; the platform may comprise the compartment of the base. The component may comprise a control system for the module; the control system may be operated on a cycle intended to administer a dose of ultraviolet light to the object. The cover may comprise a door; the control system for the module may be operated by a method comprising the steps of (a) opening the door; (b) placing the object; (c) closing the door; (d) administering the dose of light to the object; (e) opening the door; and (f) removing the object. The object may comprise biomatter; the dose of radiation is intended to sanitize the object of biomatter.

The present invention relates to a system for a vehicle interior configured to administer a dose of radiation to an object comprising a component comprising a base and a cover and a compartment for the object; a module comprising a radiation source operated by a control program; a control panel configured to provide a user interface in operation of the module; the user interface may comprise presentation of a signal; the radiation source may be configured to administer the dose of radiation to the object according to a control program. The radiation may comprise ultraviolet light; the radiation source may comprise an ultraviolet light source configured to administer the dose of ultraviolet light to the object. The user interface may be configured for operation of the module. The component may comprise a platform. The cover may be configured to move between a closed position and an open position. The cover may be configured to be moved to the closed position for administration of the dose of radiation. The cover may be configured to be moved to the open position relative to the base providing access to the compartment. The compartment may comprise a bin; the radiation source may be configured to direct radiation into the bin. The radiation source may comprise at least one LED. The radiation source may comprise an ultraviolet light source configured to administer a dose of ultraviolet light to the object. The base may be configured to provide the compartment. The control panel may comprise an indicator light; the user interface may comprise a light transmissive light guide on the cover; the light guide may be aligned with the indicator light on the control panel when the cover may be in the closed position. The base may comprise the user interface; the cover may comprise at least one of (a) a light guide aligned with the user interface; and/or (b) a light pipe aligned with the user interface. The radiation source may comprise at least one of (a) an LED; (b) an LED lamp; (c) an LED array; (d) at least one LED; (e) a set of two LEDs; (f) a lamp installed within the base; (g) a light emitting diode installed within the base; and/or (h) a UV-C LED installed within the base. The radiation source may comprise a lamp installed within the base. The module may be mounted in the base; the base may be configured to be installed in/under an instrument panel. The control panel may comprise a button. The component may comprise a control system for the module; the control system may be operated according to the control program on a cycle intended to administer a dose of ultraviolet light to the object. The cover may comprise a door; the control system for the module may be operated by a method comprising the steps of (a) opening the door; (b) placing the object; (c) closing the door; (d) administering the dose of light to the object; (e) opening the door; and (f) removing the object. The signal of the user interface may comprise at least one of a light signal and/or an audible signal; the light signal may be provided at the control panel; the audible signal may be provided at the control panel. The signal of the user interface may be provided by the control program of the module. The signal may comprise feedback. The control panel may comprise an operator control configured to operate the module of the component; the operator control may be configured to select an operation cycle for the module; the operation cycle may comprise administration of the dose of radiation to the object. The signal may comprise a completion signal for the module. The completion signal may be configured to indicate completion of an operation cycle for the module. The signal may comprise a fault signal for the module. The signal may comprise an interrupt signal for the module. The signal may be provided by an indicator; the indicator may comprise a sound transmitter; the indicator may comprise a light. The light may comprise a light-transmissive element to provide illumination. The radiation source may comprise an LED arrangement configured to provide at least 100 mW of LED light; the LED light comprise a wavelength of about 275 nm. The LED arraignment may comprise two LED lights; each LED light may comprise a 50 mA LED configured to provide at least 100 mA total UVC energy. The control program may be configured to operate the module with an operation cycle. The operation cycle may comprise a 60 second cycle time. The compartment may be configured to place the object at about 15 cm from the radiation source; the radiation source may be configured to provide at least a 3 log reduction in virus/bacteria on the object; the radiation source may be configured to provide at least a 99.9 percent reduction in active biomatter on the object. The module may be configured to provide 100 mA of UVC power; the operation cycle may comprise a cycle time of about 120 seconds. The control panel may comprise an override switch. The component may comprise a glovebox comprising a switch configured to turn off the radiation source; the cover may comprise a door for the glove box and the control program may be configured to turn off the radiation source if the switch detects that the door is open. The control panel may comprise a push button to activate the module. The control panel may comprise a remote button to activate the module. The remote button may be within the vehicle interior. The remote button may be within the center stack of the vehicle interior. The user interface may comprise LED lights. The user interface may comprise a button. The signal from the user interface may be configured to indicate of status of operation of the module. The signal may comprise a blinking light when in operation during administration of the dose of radiation and a solid light administration of the dose of radiation may be completed. The signal may comprise a light that may be off when the module may be not in operation. The signal may comprise a sound during administration of the dose of radiation. The signal may comprise a sound to indicate completion of administration of the dose of radiation. The signal may comprise an alert in a fault condition. The signal may comprise an audible tone every 5 seconds during administration of radiation. The signal may comprise a buzzer with transmit with a pattern. The pattern may comprise a tone every 1 second when in operation and for 4 seconds when completed. The component may comprise at least one of a storage compartment, a glove box, a console, a floor console, an overhead console, a trim panel, and/or a door panel. The object may comprise biomatter; the dose of radiation may be intended to sanitize the object of biomatter.

The system may be operated according to a method comprising the steps of: (a) setting a cycle for operation of the system; (b) initiating the cycle for operation of the system; (c) monitoring the system in operation; and (d) providing the signal at the user interface; monitoring the system in operation may comprise determining status of the system; operation of the system may comprise at least one of applying the dose of radiation to the object or ending the cycle if a fault is detected; the signal may be provided to indicate status of the system. The status of the system may be determined according to the control program. Ending the cycle if a fault is detected may comprise an interrupt of operation; ending the cycle may comprise not applying the dose of radiation to the object. The signal may comprise a completion signal when the cycle of operation is completed. The signal may comprise an operation signal during operation of the system. The signal may comprise a fault signal if the cycle of operation is not completed. Setting the cycle may comprise selection of the cycle at the control panel. The component may comprise a sensor to indicate status; and monitoring the system in operation may comprise monitoring status indicated by the sensor. Status may comprise presence of the object in the compartment; status may comprise status of the cover. The cover may comprise a door movable from an open position to a closed position; status may comprise detection of whether the door is in an open position; when the door is in an open position the step of monitoring the system in operation may comprise indicating a fault status and providing a fault signal. Monitoring the system may comprise ending the cycle by interrupt if the fault status is not corrected. Monitoring the system may comprise ending the cycle if interrupt status is detected. Interrupt status may be provided at the control panel. The signal may be provided according to the control program. The cycle for operation may be provided according to the control program. The control program may comprise a cycle time. The control program may operate using data from a control system. The control program may be configured to operate the module to administer the dose of radiation to the object; the object may comprise biomatter; the dose of radiation is intended to sanitize the object of biomatter.

FIGURES

FIG. 5A is a schematic perspective view of a component/system for treatment/radiation of an article/object in a vehicle interior according to an exemplary embodiment.

FIG. 5B is a schematic exploded perspective view of a component/system for treatment/radiation of an article/object in a vehicle interior according to an exemplary embodiment.

FIGS. 6A and 6B are schematic perspective views of a component/system for treatment/radiation of an article/object in a vehicle interior according to an exemplary embodiment.

FIGS. 6C and 6D are schematic side elevation section views of a component/system for treatment/radiation of an article/object in a vehicle interior according to an exemplary embodiment.

FIGS. 11A and 1B are schematic perspective views of a component/system for treatment/radiation of an article/object in a vehicle interior according to an exemplary embodiment.

FIGS. 13A through 13G are schematic perspective views of a component/system for treatment/radiation of an article/object in a vehicle interior according to an exemplary embodiment.

FIG. 28A is a schematic side elevation view of a component/system for treatment/radiation of an article/object in a vehicle interior according to an exemplary embodiment.

FIG. 28B is a schematic perspective view of a component/system for treatment/radiation of an article/object in a vehicle interior according to an exemplary embodiment.

FIG. 28C is a schematic partial rear elevation view of a component/system for treatment/radiation of an article/object in a vehicle interior according to an exemplary embodiment.

FIGS. 32A through 32D are schematic flow diagrams of operation of a component/system for treatment/radiation of an article/object in a vehicle interior according to an exemplary embodiment.

DESCRIPTION

Referring to FIGS. 1A-1C and 2A-2C, a vehicle V is shown with an interior I comprising components C such as an instrument panel IP providing a storage compartment shown as a glove box GB and a console shown as a floor console FC providing a storage compartment. As indicated schematically in FIG. 1C, the component C may comprise a system configured to provide a control panel CP. See also FIG. 2C.

Figure 1A:
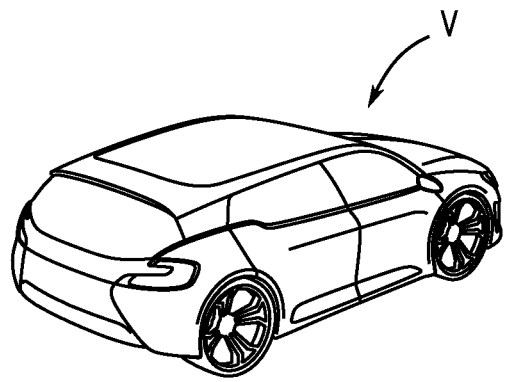
FIG. 1A is a schematic perspective view of a vehicle according to an exemplary embodiment.
Figure 1B:
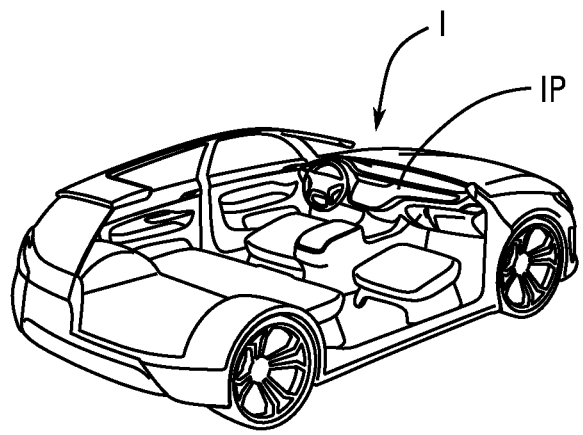
FIGS. 1B and 1C are schematic perspective cut-away views of a vehicle showing an interior according to an exemplary embodiment.
Figure 1C:
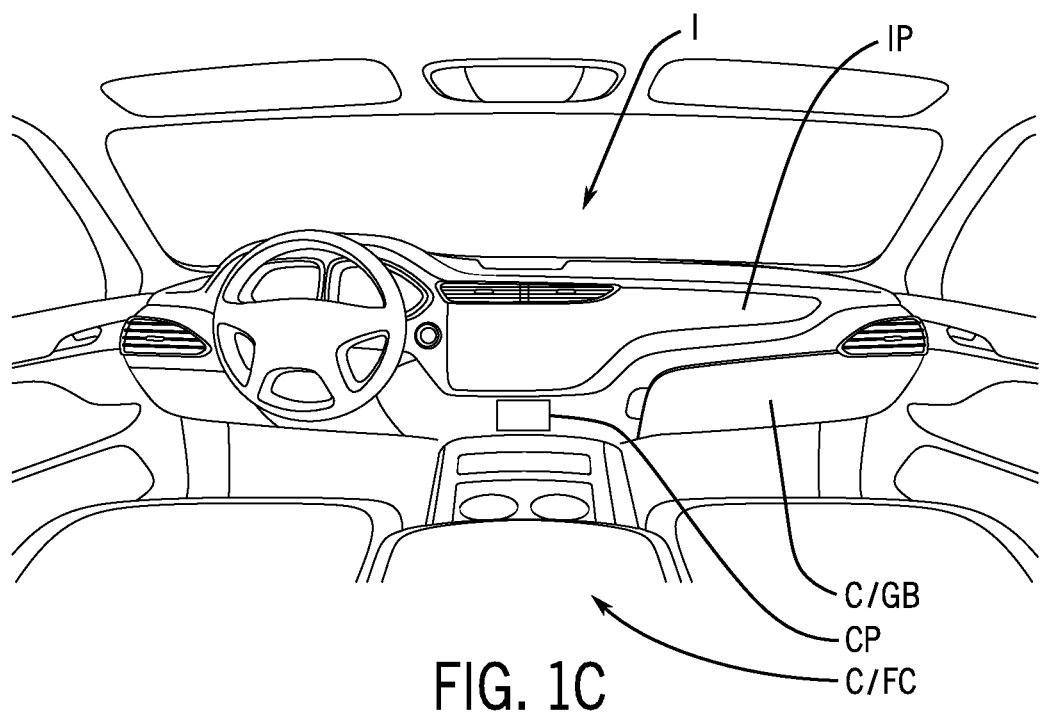
Figure 2A:
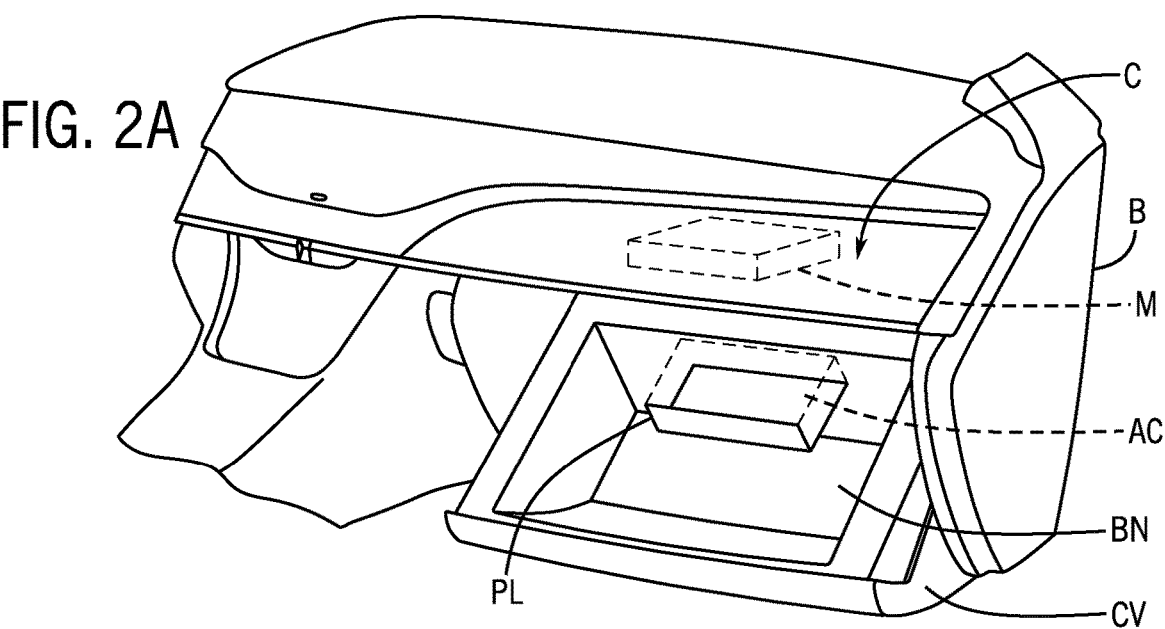
FIGS. 2A to 2B are schematic perspective views of a component/system for the interior of the vehicle according to an exemplary embodiment.
Figure 2B:
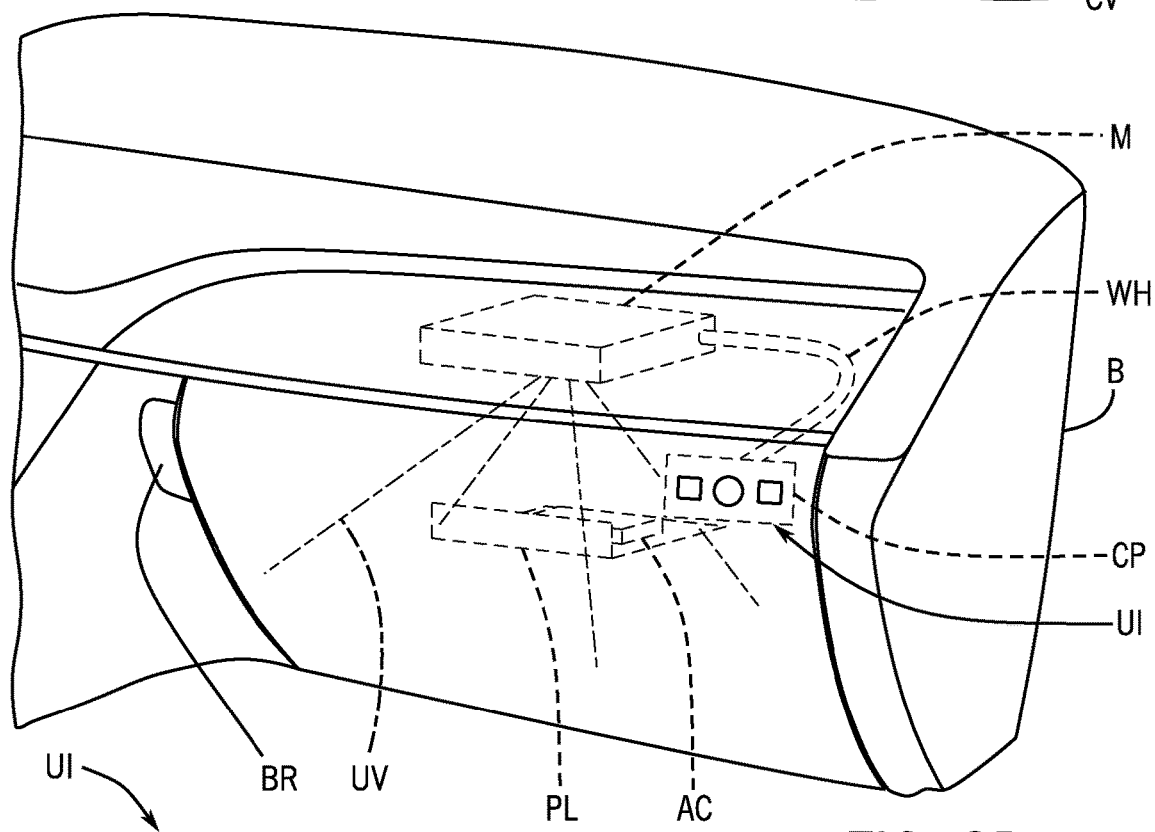

As shown schematically according to an exemplary embodiment in FIGS. 2A-2B, the system/component C may comprise a base/frame B and a compartment/bin BN with a pivoting cover CV. See also FIGS. 5A-5B and 6A-6D. As indicated schematically in FIGS. 2A-2C, 3A-3C, 4A-4B, 30A-30B and 31A-31B, the system/component C may comprise a module M configured to administer radiation such as ultraviolet light UV from a light source LS to an article AC within the compartment/bin BN. See also FIGS. 5A-5B, 6A-6D, 25, 26, 27A and 28A-28C. As shown schematically, the system/component may comprise a control panel CP configured to present a user interface UI providing instrumentation and/or control elements (e.g. such as button BT, indicator/icon IC, etc.) for operation/monitoring of the module M. See also FIGS. 3A-3C (showing system arrangement comprising module/controller operable with data/control program and with light source/LED, fan, etc.) and 31A-31B (showing system arrangement). As indicated schematically in FIGS. 2A-2C, 3A-3C, 4A-4B, 30A-30B, 31A-31B and 32A-32D, the module M of the system/component C may comprise a radiation system configured to administer a dose of radiation such as UV light to the article; the module M may comprise a controller configured to be operated by the control panel CP; the system/component C may be configured to be operated by the controller/control system with a control program through the control panel with an input device and/or indicator such as an output audible signal (e.g. speaker) and/or visible signal (e.g. light) for instrumentation and/or control at the user interface; the control system/control program for the system may provide for operation and control and indicators of an occupant of the vehicle (e.g. an operation cycle, selection of a cycle, etc.). See also FIGS. 1C, 6A-6D, 11A-11B, 12, 13A-13F, 15A-15F, 19A-19F, 25, 26, 27A-27B, 28A-28C and 29.

Figure 2C:
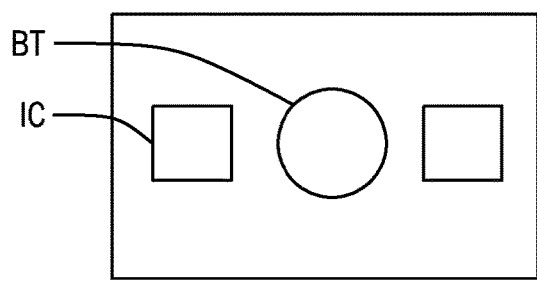
FIG. 2C is schematic diagram of a user interface/control panel according to an exemplary embodiment.
Figure 3A:
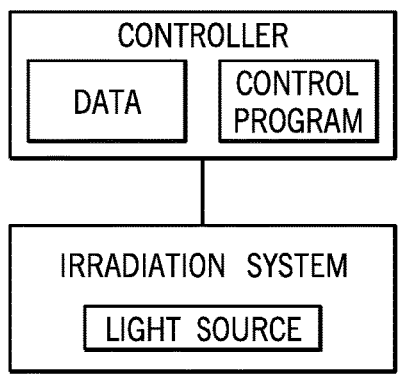
FIGS. 3A and 3B are schematic block diagrams of a component/system for treatment/radiation of an article/object in a vehicle interior according to an exemplary embodiment.
Figure 3B:
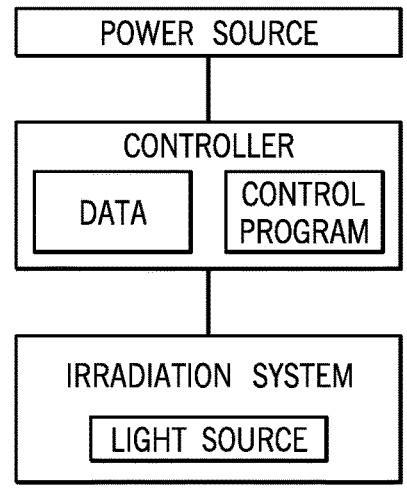
Figure 3C:
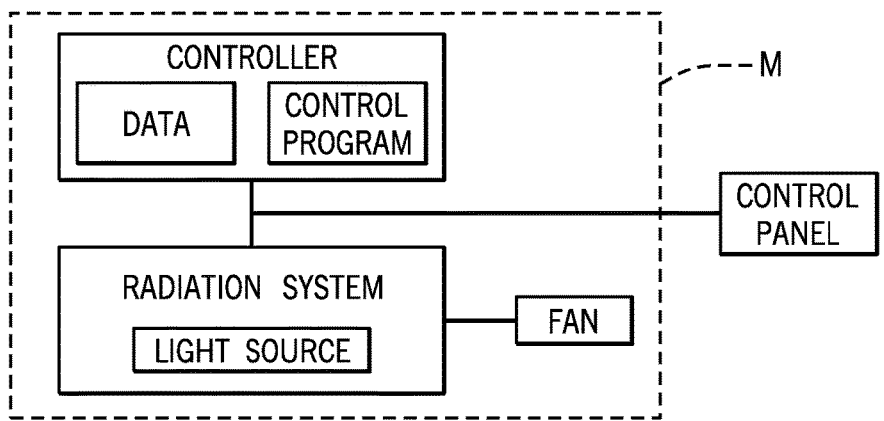
FIG. 3C is a schematic block diagram of a component/system for treatment/radiation of an article/object in a vehicle interior according to an exemplary embodiment.
Figure 4A:
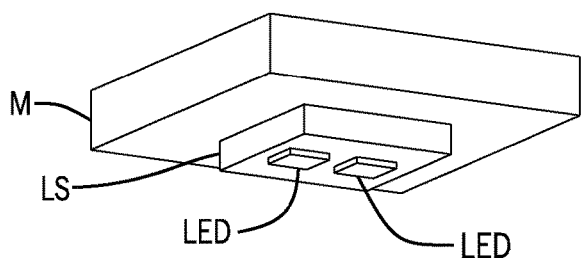
FIGS. 4A and 4B are schematic perspective views of a component/system for treatment/radiation of an article/object in a vehicle interior according to an exemplary embodiment.
Figure 4B:
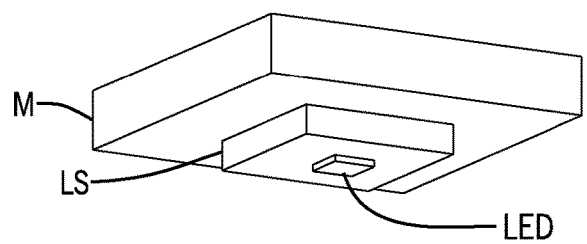
Figure 7A:
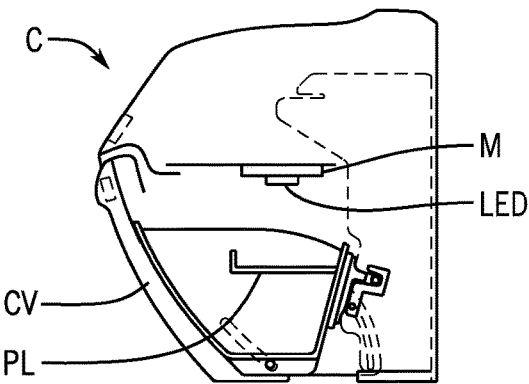
FIGS. 7A through 7F are schematic side views of a component/system for treatment/radiation of an article/object in a vehicle interior according to an exemplary embodiment.
Figure 7B:
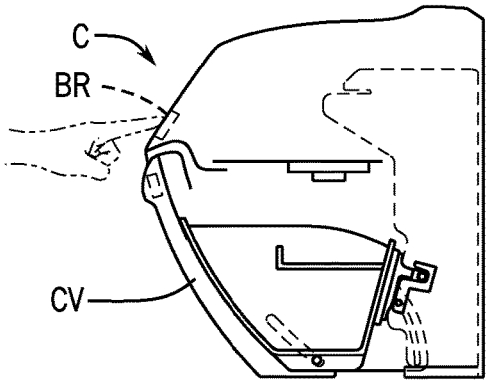
Figure 7C:
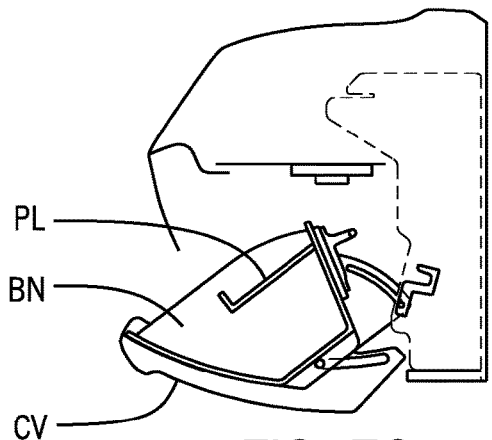
Figure 7D:
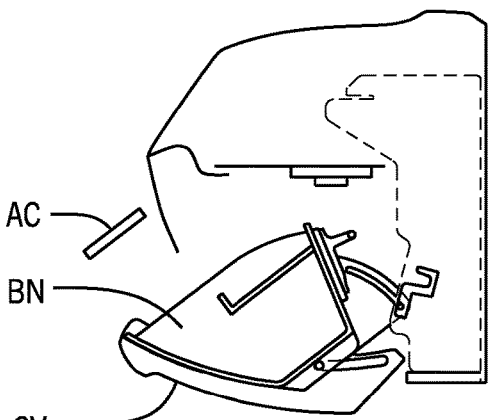
Figure 7E:
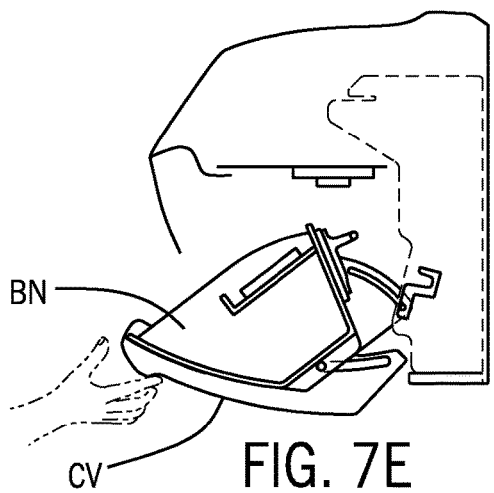
Figure 7F:
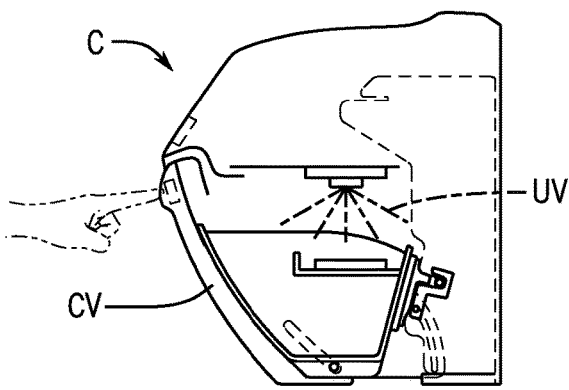
Figure 8A:
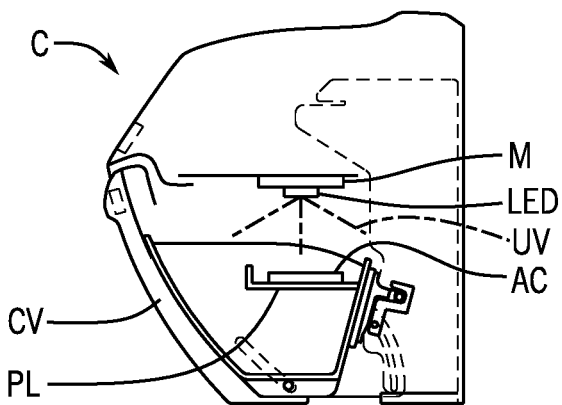
FIGS. 8A through 8F are schematic side views of a component/system for treatment/radiation of an article/object in a vehicle interior according to an exemplary embodiment.
Figure 8B:
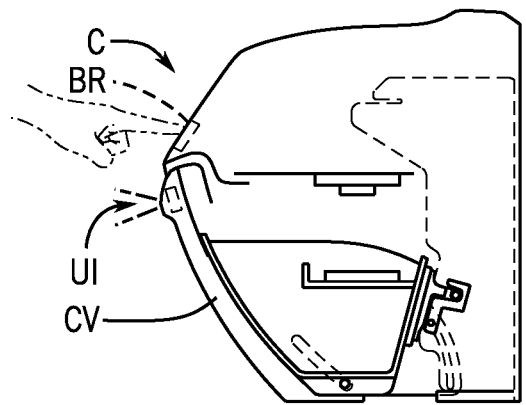
Figure 8C:
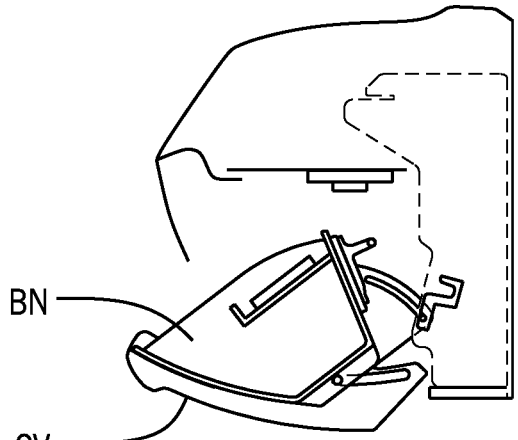
Figure 8D:
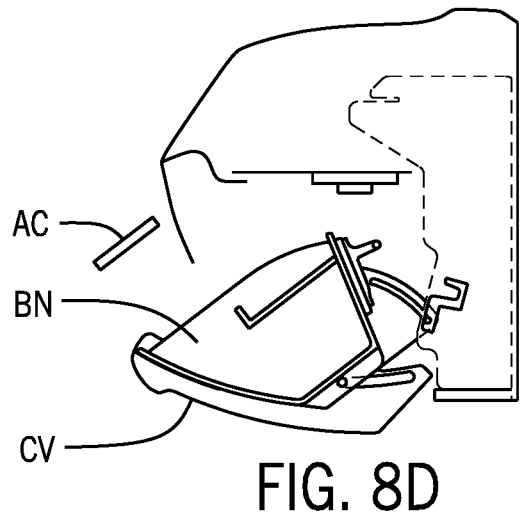
Figure 8E:
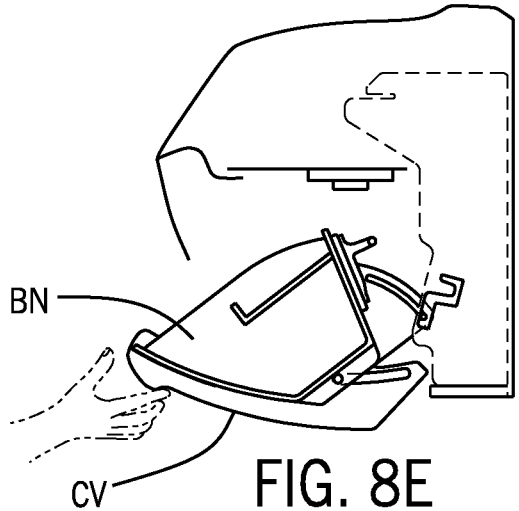
Figure 8F:
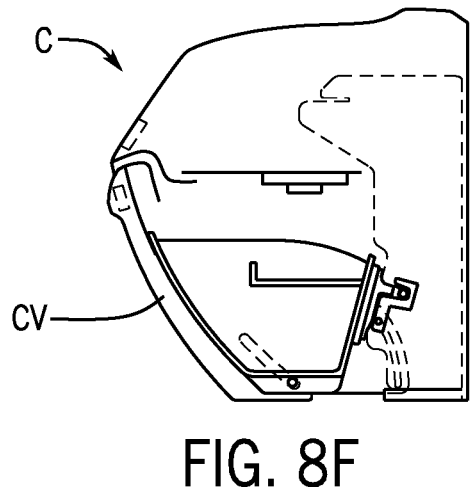
Figure 9A:
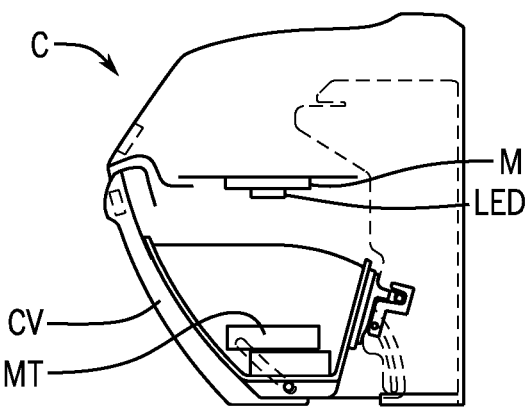
FIGS. 9A through 9F are schematic side views of a component/system for treatment/radiation of an article/object in a vehicle interior according to an exemplary embodiment.
Figure 9B:
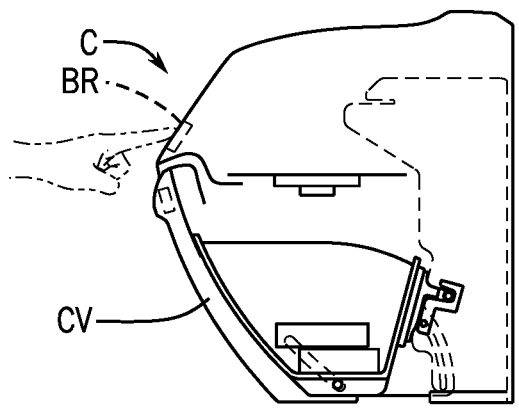
Figure 9C:
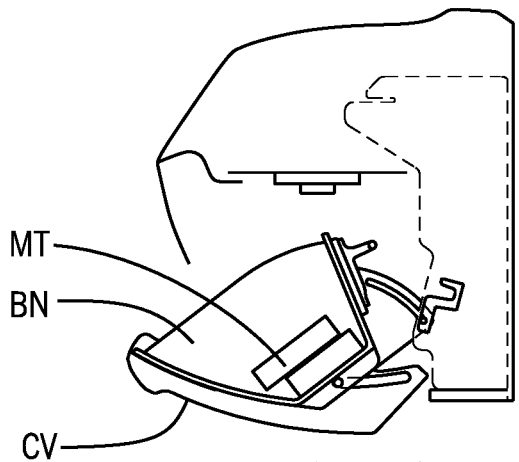
Figure 9D:
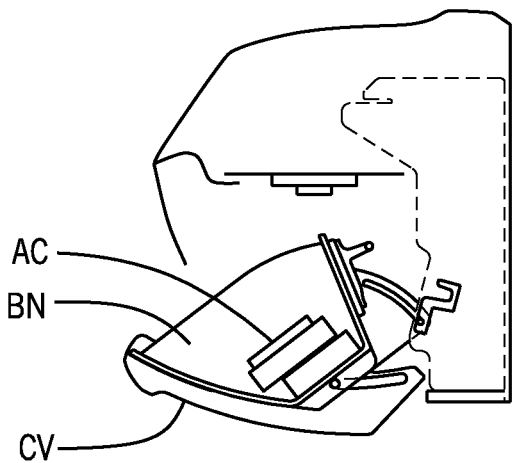
Figure 9E:
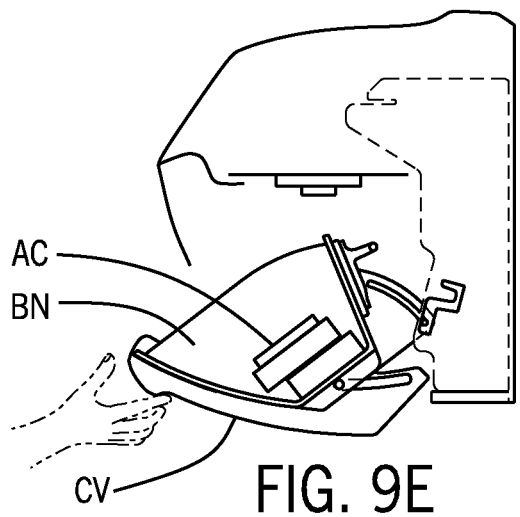
Figure 9F:
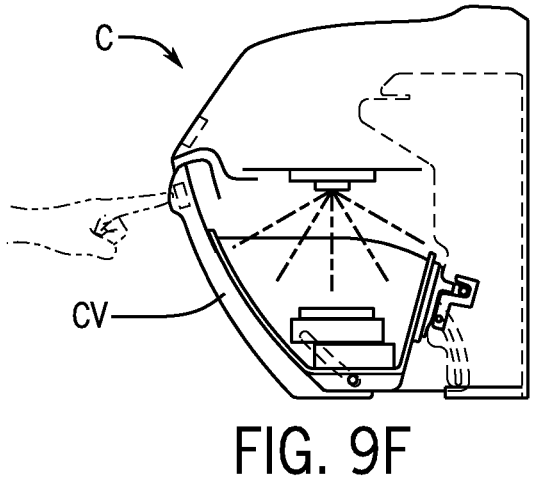
Figure 10A:
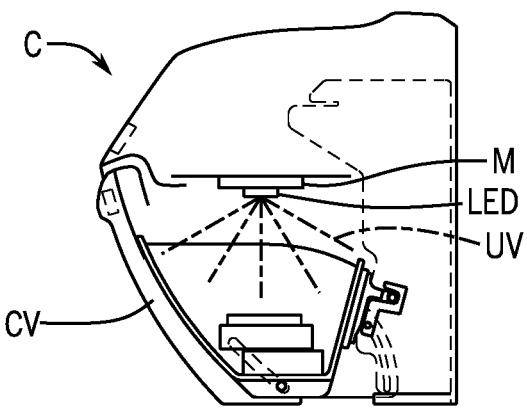
FIGS. 10A through 10F are schematic side views of a component/system for treatment/radiation of an article/object in a vehicle interior according to an exemplary embodiment.
Figure 10B:
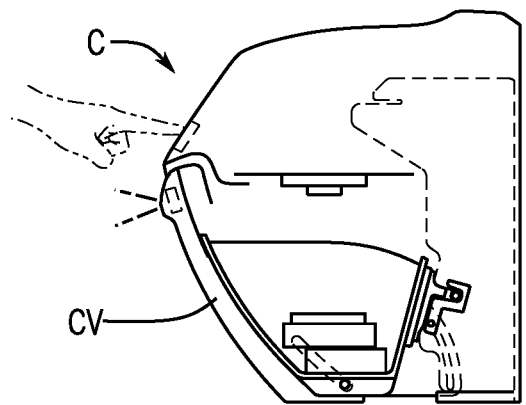
Figure 10C:
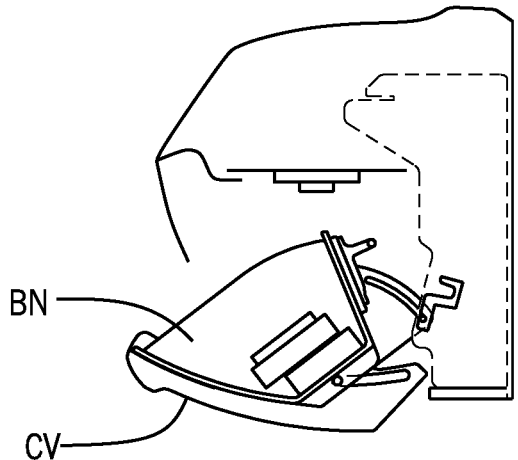
Figure 10D:
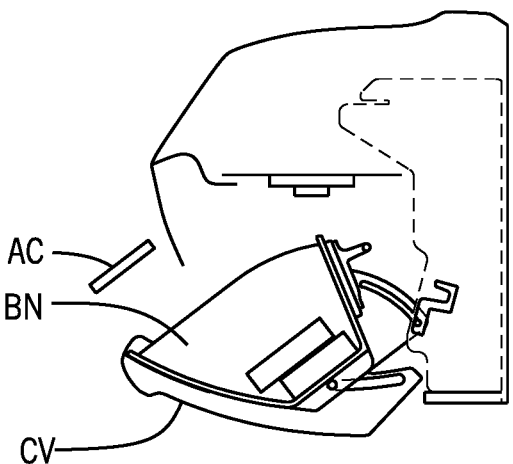
Figure 10E:
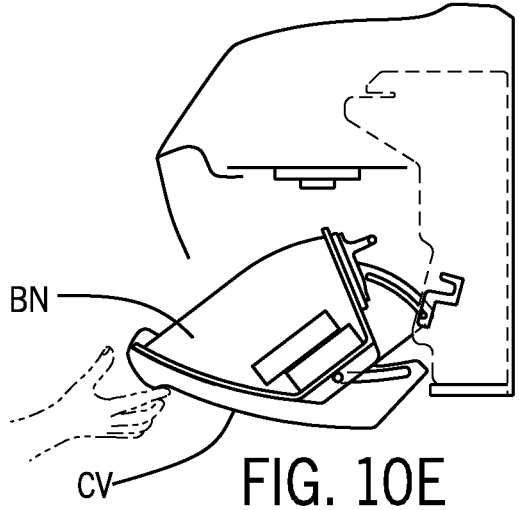
Figure 10F:
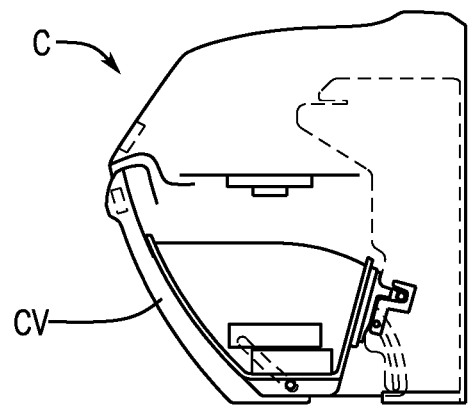
Figure 11A:
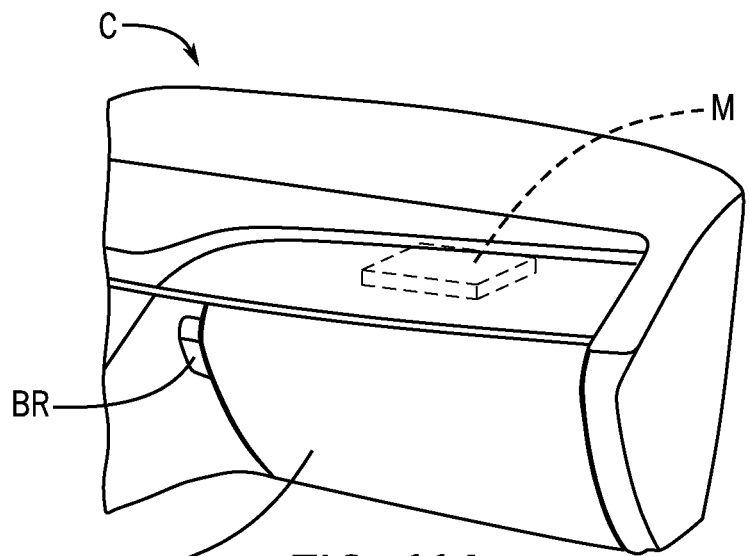
Figure 11B:
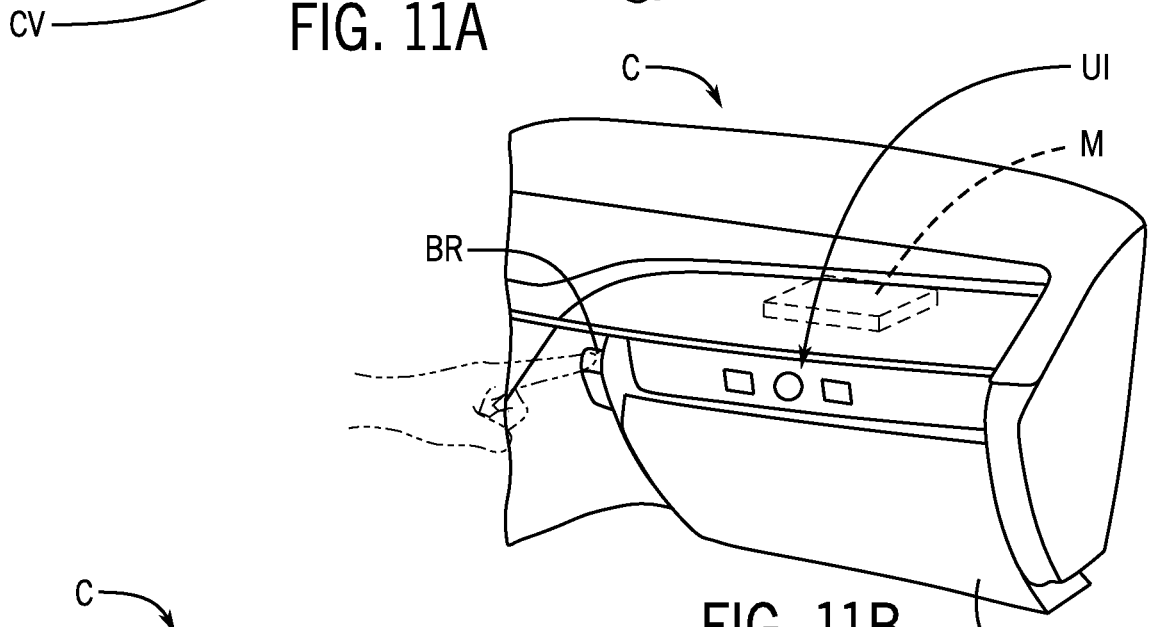
Figure 12:
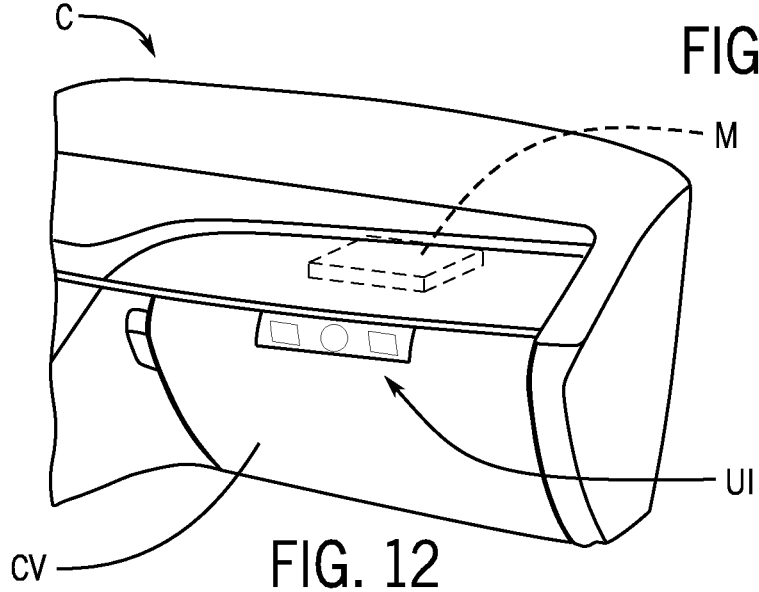
FIG. 12 is a schematic perspective view of a component/system for treatment/radiation of an article/object in a vehicle interior according to an exemplary embodiment.
Figure 14A:
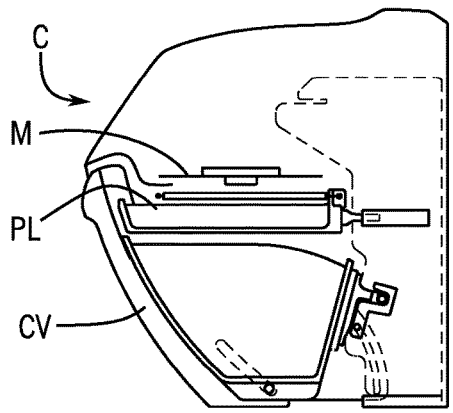
FIGS. 14A through 14F are schematic side views of a component/system for treatment/radiation of an article/object in a vehicle interior according to an exemplary embodiment.
Figure 14B:
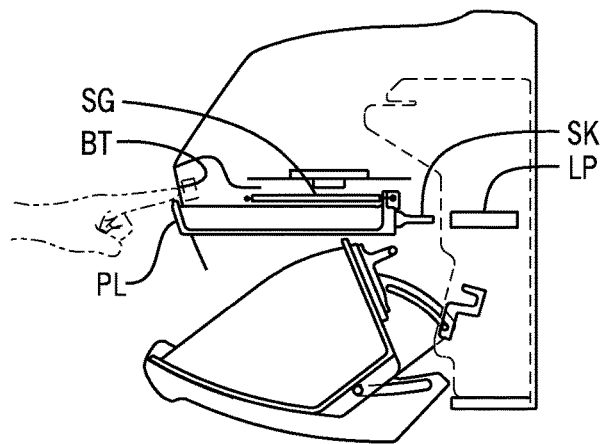
Figure 14C:
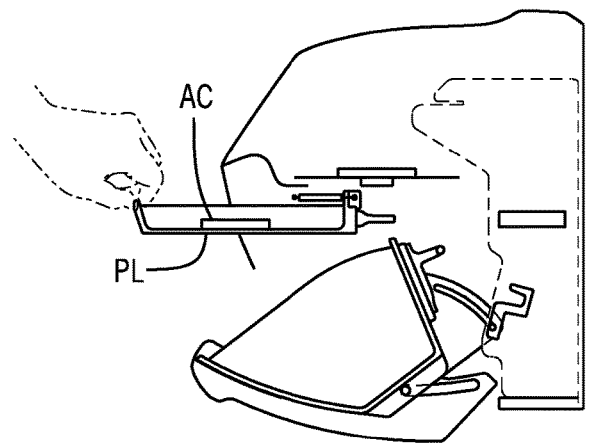
Figure 14D:
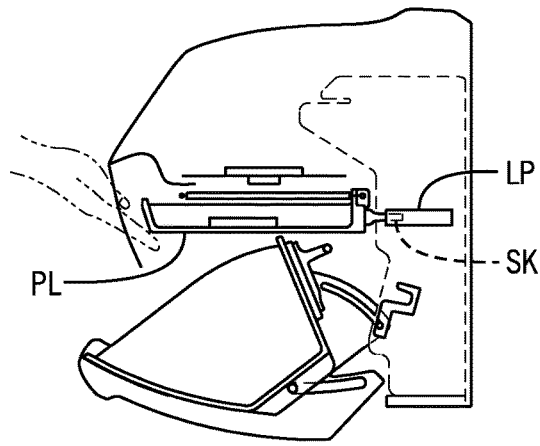
Figure 14E:
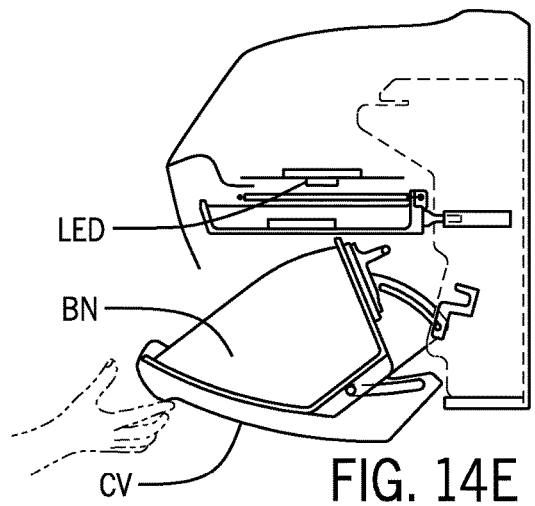
Figure 14F:
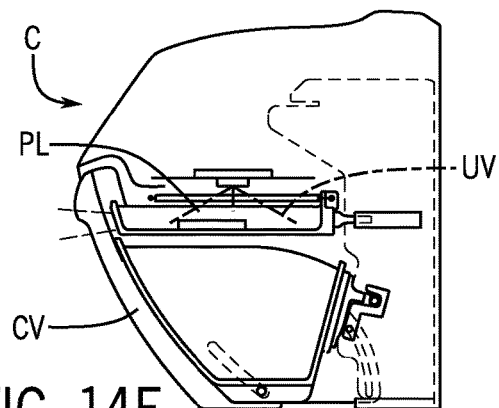
Figure 15A:
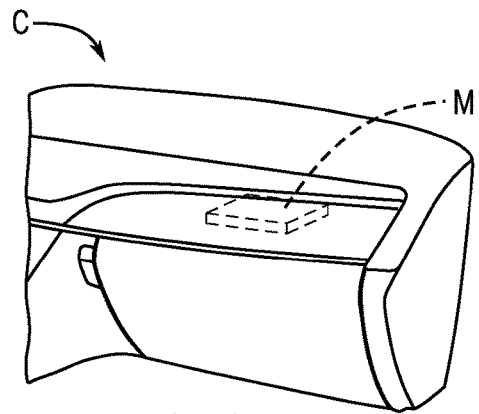
FIGS. 15A through 15F are schematic perspective views of a component/system for treatment/radiation of an article/object in a vehicle interior according to an exemplary embodiment.
Figure 15B:
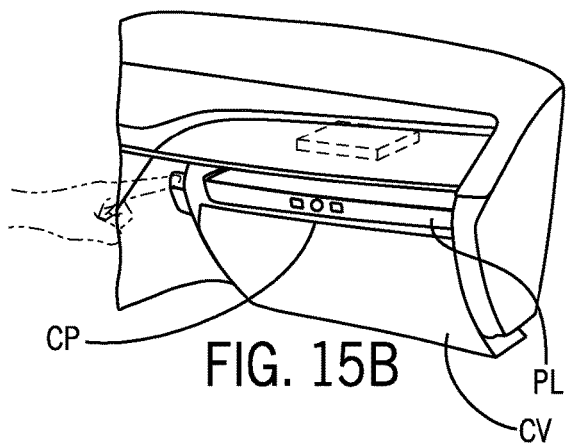
Figure 15C:
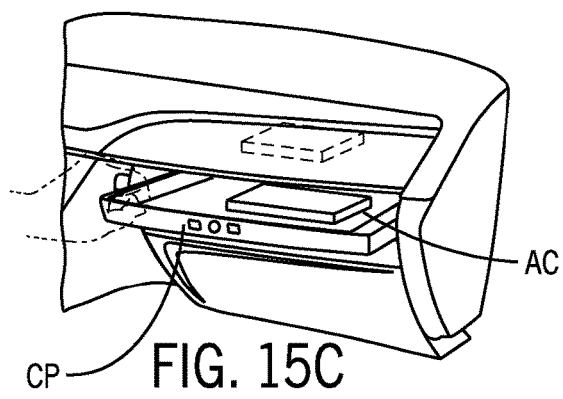
Figure 15D:
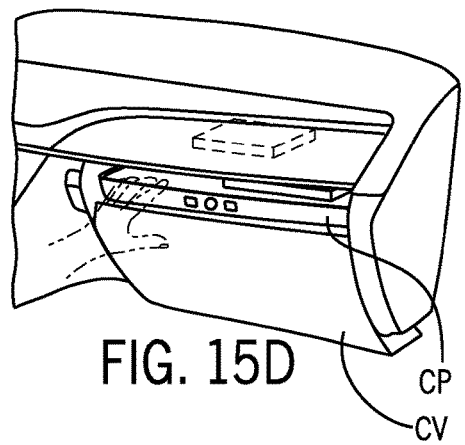
Figure 15E:
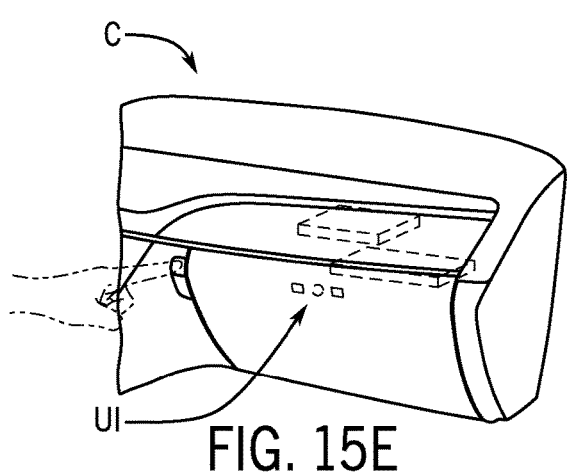
Figure 15F:
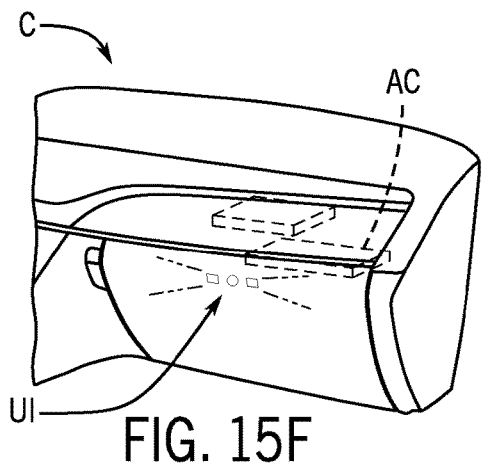
Figure 16A:
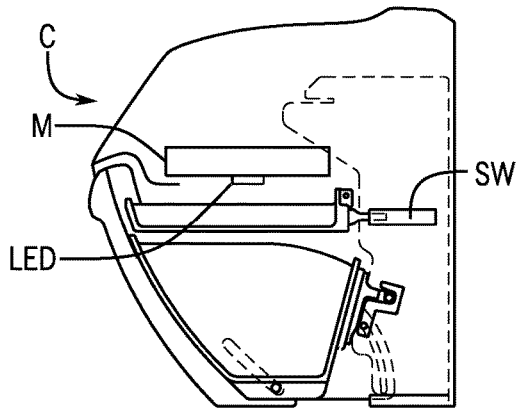
FIGS. 16A through 16F are schematic side views of a component/system for treatment/radiation of an article/object in a vehicle interior according to an exemplary embodiment.
Figure 16B:
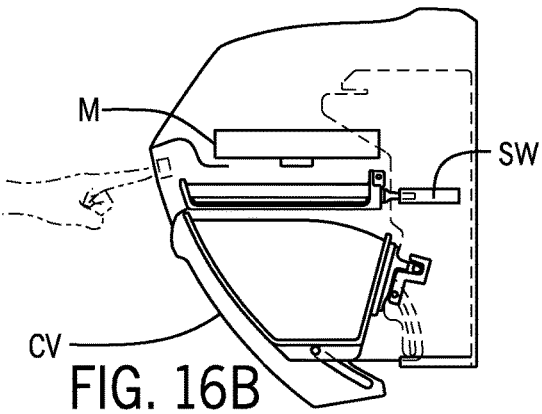
Figure 16C:
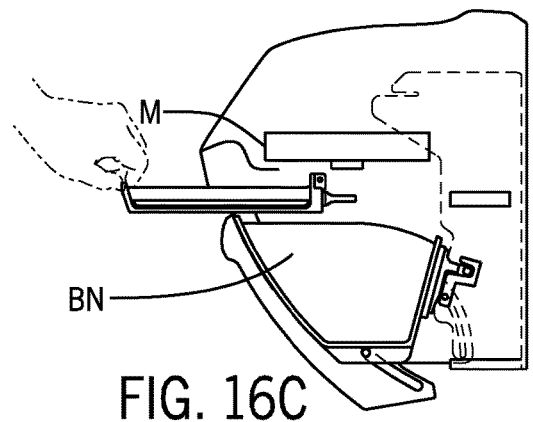
Figure 16D:
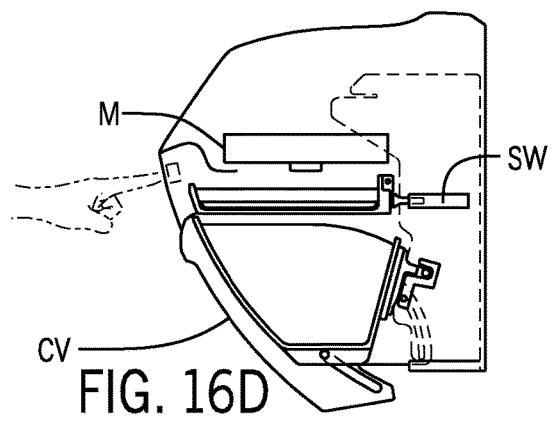
Figure 16E:
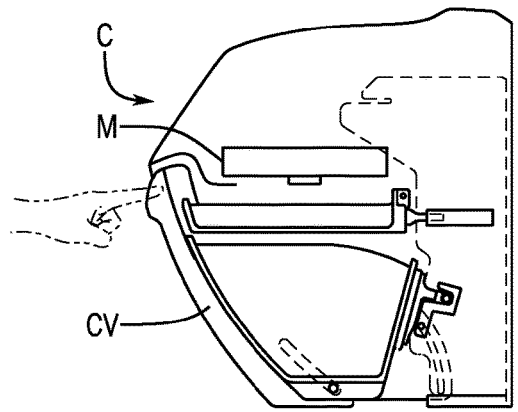
Figure 16F:
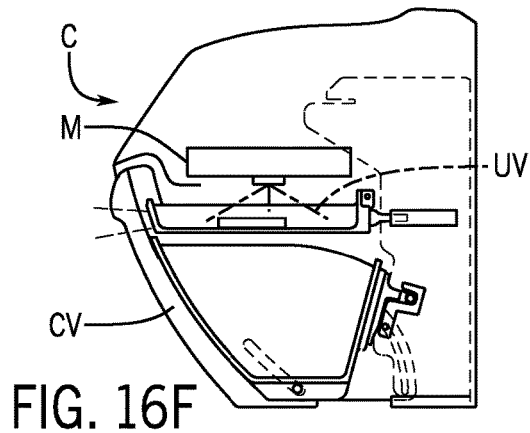
Figure 17A:
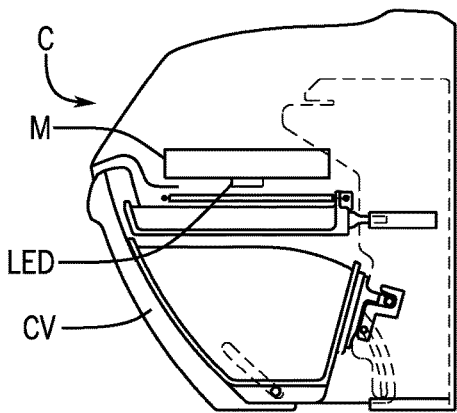
FIGS. 17A through 17F are schematic side views of a component/system for treatment/radiation of an article/object in a vehicle interior according to an exemplary embodiment.
Figure 17B:
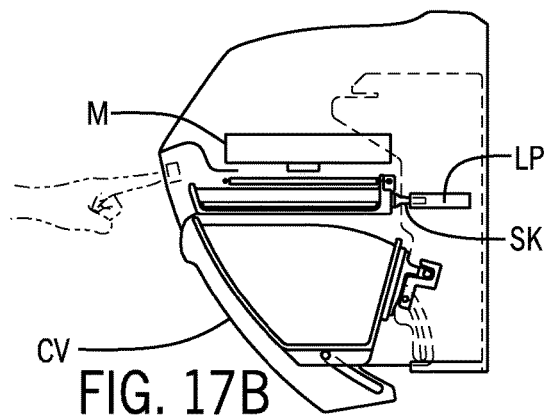
Figure 17C:
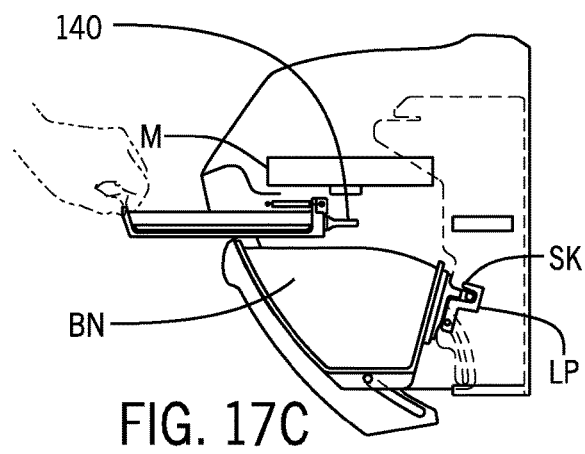
Figure 17D:
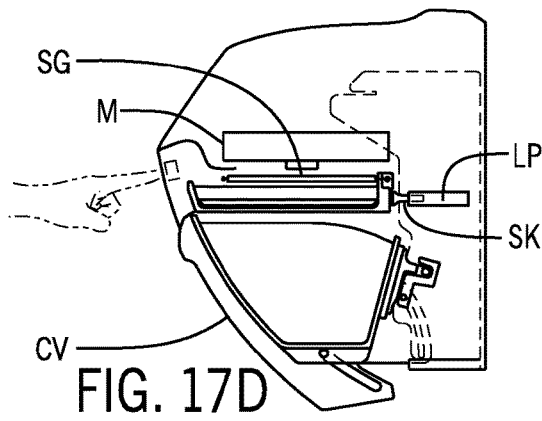
Figure 17E:
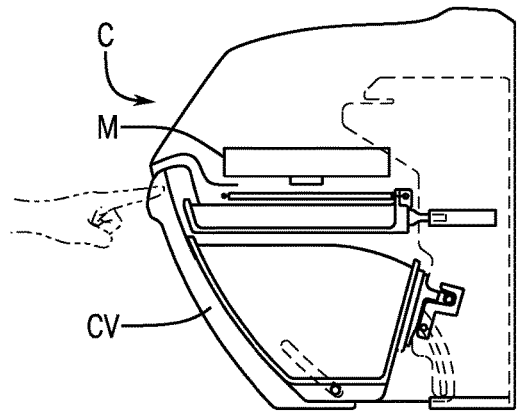
Figure 17F:
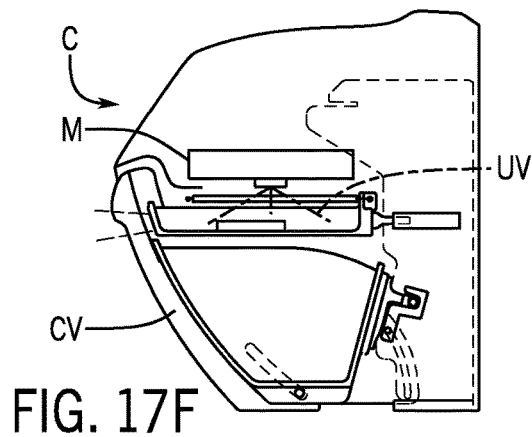
Figure 18A:
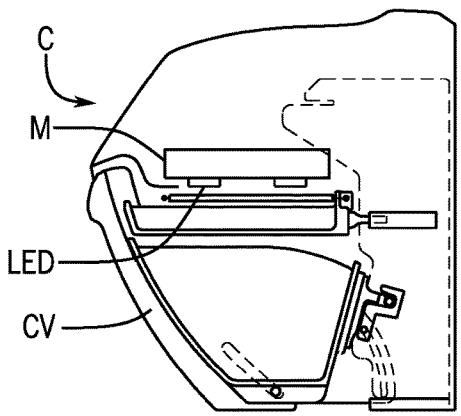
FIGS. 18A through 18F are schematic side views of a component/system for treatment/radiation of an article/object in a vehicle interior according to an exemplary embodiment.
Figure 18B:
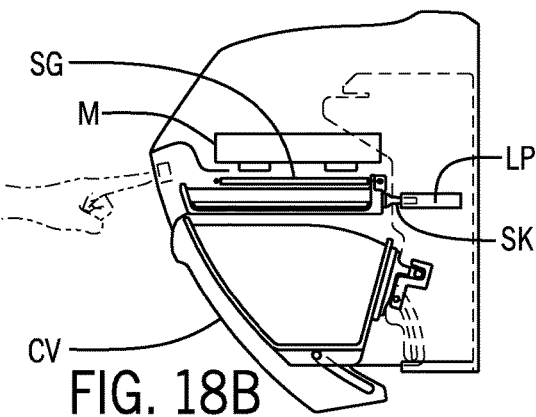
Figure 18C:
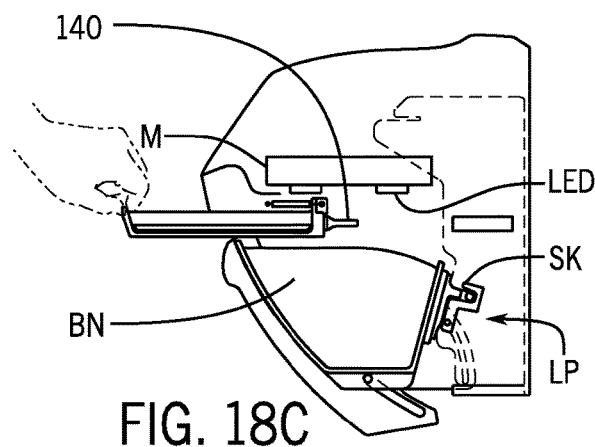
Figure 18D:
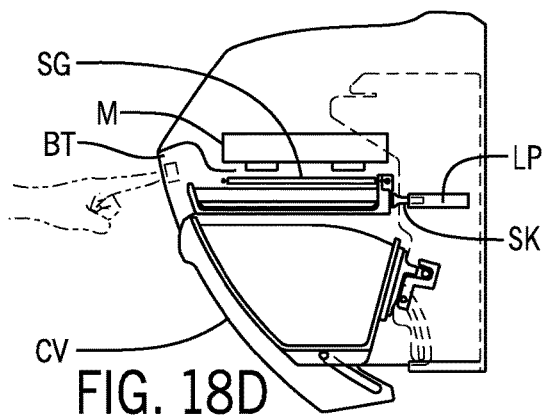
Figure 18E:
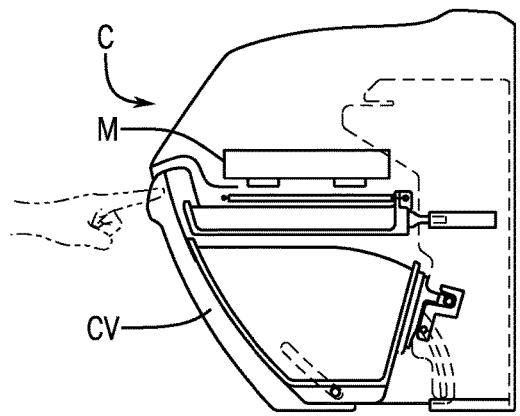
Figure 18F:
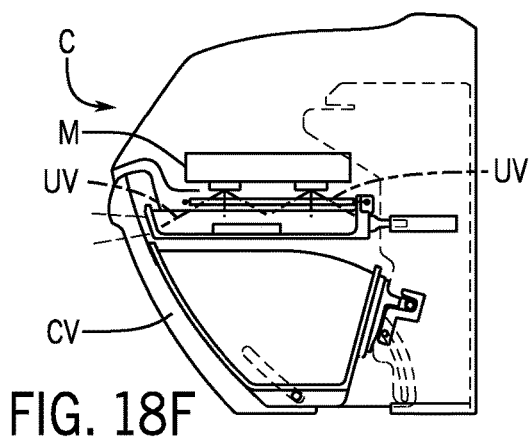
Figure 19A:
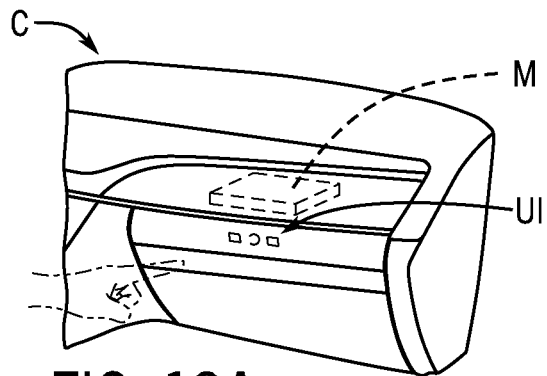
FIGS. 19A through 19F are schematic perspective views of a component/system for treatment/radiation of an article/object in a vehicle interior according to an exemplary embodiment.
Figure 19B:
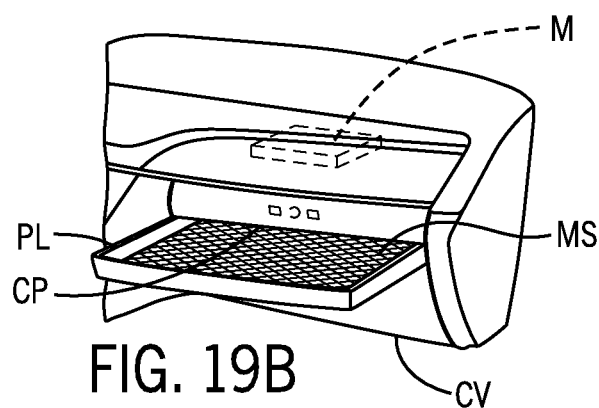
Figure 19C:
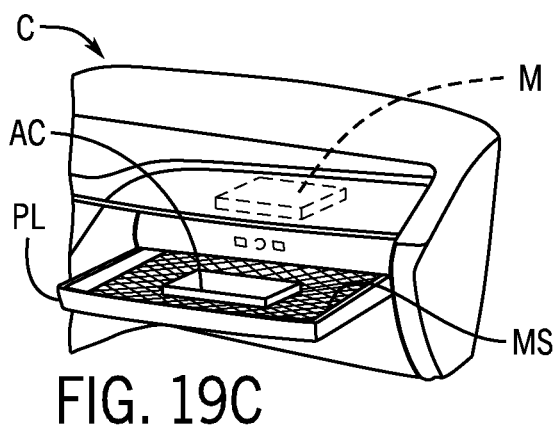
Figure 19D:
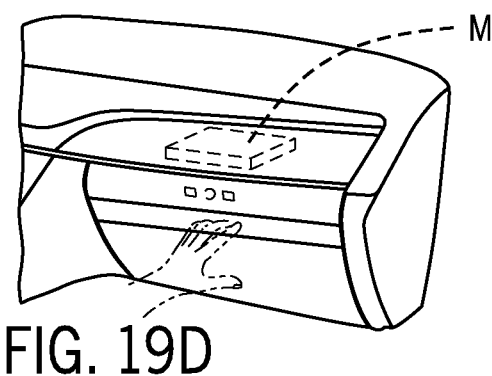
Figure 19E:
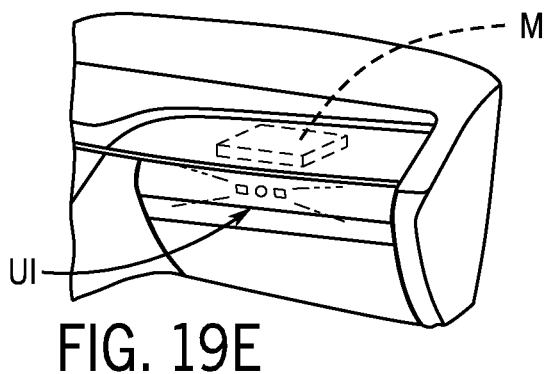
Figure 19F:
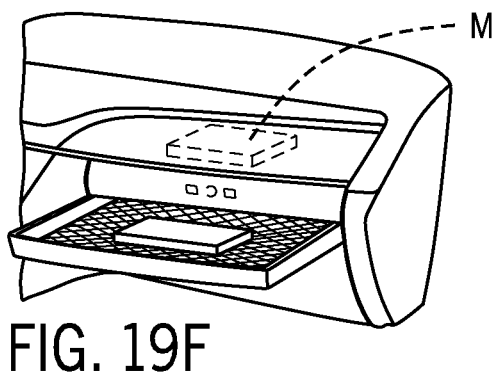

Referring to FIGS. 2A-2C, the system/component C may comprise a base/frame B with a compartment/bin BN (e.g. for materials, articles, objects, etc.) and a cover CV movable between a closed position and an open position to facilitate access; the system/component C may comprise a module M with cable/connection to a control panel CP configured to present a user interface UI comprising an input device/operator control shown as a button BT and an indicator IC (e.g. configured to provide indicator signals such as visual/light from a light/light panel and/or audible/sound from a sound transmitter/speaker). See also FIGS. 1C, 3A-3C, 31A-31B and 32A-32D. As shown schematically in FIGS. 2A-2C, the system/component C may comprise an operator control such as a button/release BR for the cover; the bin/compartment BN may comprise a shelf/platform PL for objects such as articles AC; as indicated radiation shown as UV light from light source LS (with the LED arrangement) may be directed from the module M onto articles AC within the bin BN and/or on platform PL. See also FIGS. 4A-4B.

As shown schematically in FIGS. 3A-3C and 31A-31C, the system/component may comprise a module M with a radiation system comprising a light source and a controller/control system (operating with a control program, data, etc.) connected to the control panel/user interface and to a power source/supply and other vehicle systems/networks. As indicated schematically in FIG. 3C, the system/component may comprise a fan (e.g. configured to provide cooling for the module, light source, electronic components, etc.). As indicated schematically in FIGS. 31B and 32A-32D, the system/component may comprise a safety system such as a sensor/switch configured to provide a signal to the controller/control system (e.g. for the module with light source) indicating whether the light source should be operated/activated and to provide data/signal for monitoring operation of the system/component (e.g. fault, interrupt, continuation, cycle operation, etc. according to the control program for module M). See FIGS. 5A-5B and 6A-6D and 16A-16F (showing sensor/switch SW for system indicating whether cover/door CV for compartment BN is closed or open). As shown schematically in FIGS. 3A-3C, 4A-4B and 31A-31B, the system/module M may be configured to actuate a light source LS shown as comprising an LED arrangement (e.g. single and/or multi-LED, array, etc.) configured to administer the dose of ultraviolet light UV to the object/article AC in the compartment BN according to the control program. See also FIGS. 2B, 30B and 32A-32D.

As indicated schematically according to an exemplary embodiment in FIGS. 2A-2C, the component/system may be configured to administer treatment (e.g. dose) of ultraviolet light UV from the module M providing the light source LS directed to an object/article AC (e.g. item shown representationally as mobile device/phone) placed in the bin/compartment BN according to the control program for the control system/controller for module M (e.g. according to a process, cycle, program, algorithm, etc. in a dose intended to neutralize biomatter such as may be upon the surface of the article within the range of the UV light). See also FIGS. 3A-3C, 4A-4B, 25, 26, 31A-31C and 32A-32D. As indicated schematically in FIGS. 1C, 2A-2C, 3A-3C and 31A-31C, at the user interface UI provided by the control panel CP (e.g. configured to provide instrumentation and/or control) for the module M the vehicle occupant may be able to actuate the system/component to administer the dose of radiation/UV light to the article according to a selectable cycle according to a control program. See also FIGS. 32A-32D (e.g. when the cover/door is closed the light source/LED arrangement of the module may be operated to administer the UV light to the article in a cycle according to the control program but if the cover/door is not closed a fault/interrupt signal may be provided according to the control program).

As indicated schematically according to an exemplary embodiment in FIGS. 5A-5B and 6A-6D, the system/component C may comprise a base/frame B with a compartment/bin BN (e.g. for materials, articles, objects, etc.) and a cover CV with release/button BR movable between a closed position and an open position to facilitate access; the system/component C may comprise a module M with light source LS/LED and with connection to a control panel configured to present a user interface (e.g. comprising an input device/operator control shown as a button and an indicator configured to provide indicator signals such as visual/light from a light/light panel and/or audible/sound from a sound transmitter/speaker) and with connection to a sensor/switch SW configured to provide a signal to the control system/controller (e.g. to detect whether cover CV is open or closed). See also FIGS. 1C, 3A-3C, 31A-31B and 32A-32D.

As shown schematically according to an exemplary embodiment in FIGS. 1C, 28A-28C, 29 and 30A-30, the component C may comprise a console shown as a floor console with a base B and cover CV with a compartment shown as bin BN and a module M comprising a radiation source shown as a ultraviolet light source comprising and LED arrangement configured to direct light UV to an object AC; the module may be configured to administer a dose of radiation comprising ultraviolet light UV to the object AC according to a control program; the module may comprise a controller/control system (with control program and/or connected to vehicle systems/networks) operated at a control panel CP configured to provide a user interface UI; the user interface may comprise an input device and/or indicators to provide a signal of system status, etc. (e.g. audible signal and/or visual signal) for a vehicle occupant. See also FIGS. 3A-3C, 31A-31B and 32A-32D.

As shown schematically in FIGS. 2A-2C and 28A-28C, the component may comprise a base B configured to provide the compartment BN and a cover CV (e.g. complete or at least partial) for the compartment with a user interface UI (e.g. configured to provide instrumentation and/or control) for the module M. As indicated schematically in FIGS. 2A-2C, 4A-4B, 7F, 8A, 9F, 10A, 13F, 14F, 15F. 16F, 17F, 18F, 19E, 20E, 25, 26 and 30A-30B, the light source/LED arrangement of the module M may be operated to administer the UV light to the articles/objects AC or material MT (e.g. according to a process, cycle, program, algorithm, etc. in a dose intended to neutralize biomatter such as may be upon the surface of the article within the range of the UV light). See also FIGS. 27A-27B (user interface comprising illuminated indicators shown as light-transmissive elements/light guides LG on the cover CV to provide illumination from indicators IC on control panel CP) and 31A-31B.

As shown schematically according to an exemplary embodiment in FIGS. 32A-32D, the system for a vehicle interior configured to administer a dose of radiation to an object (with module and control panel/user interface) may be operated according to a method provided by the control system/control program (e.g. a software/firmware program for the module). See also FIGS. 3A-3C and 31A-31B. As indicates schematically in FIGS. 32A-32D, the method may comprise the steps of: (a) setting a cycle for operation of the system (e.g. at the control panel); (b) initiating the cycle for operation of the system (e.g. in the control program); (c) monitoring the system in operation (e.g. according to the control panel using data from systems/sensors); and (d) providing the signal at the user interface. The step of setting the cycle may comprise selection of the cycle at the control panel. The step of monitoring the system in operation may comprise determining status of the system (e.g. using data, etc. according to the control program). As indicated in FIGS. 32A-32D, operation of the system may comprise at least one of applying the dose of radiation to the object or ending the cycle if a fault is detected (e.g. according to the control program with data from a sensor, switch, etc.). See also FIGS. 6A-6D (sensor/switch for cover/door). As shown schematically, the signal may be provided at the user interface to indicate status of the system. See also FIGS. 2C and 27B. The status of the system may be determined according to the control program. The signal may indicate status such as ready for operation, selection/setting of a cycle of operation, operation of cycle, fault (e.g. sensor indicating fault, cover open, etc.), interrupt (e.g. fault not corrected, user abort, etc.), completion of cycle, etc. See FIGS. 32A-32D. As shown schematically in FIGS. 32A-32D, ending the cycle if a fault is detected may comprise an interrupt of operation; ending the cycle may comprise not applying the dose of radiation to the object. The signal may comprise a completion signal when the cycle of operation is completed. The signal may comprise an operation signal during operation of the system. The signal may comprise a fault signal if the cycle of operation is not completed (e.g. if a cover/door is open or opened in operation). The component may comprise a sensor to indicate status; and monitoring the system in operation may comprise monitoring status indicated by the sensor. See FIGS. 32A-32D. Status may comprise presence of the object in the compartment; status may comprise status of the cover. The step of monitoring status may comprise detection of whether the door is in an open position; when the door is in an open position the step of monitoring the system in operation may comprise indicating a fault status and providing a fault signal. As indicated in FIGS. 32A-32D, monitoring the system may comprise ending the cycle by an interrupt if the fault status is not corrected; monitoring the system may comprise ending the cycle if an interrupt status is detected. Interrupt status may be provided at the control panel. As indicated in FIGS. 3A-3C, 31A-31B and 32A-32D, the signal may be provided according to the control program; the cycle for operation may be provided according to the control program; the control program may comprise a cycle time; the control program may operate using data from a control system; the control program may be configured to operate the module to administer the dose of radiation to the object; the object may comprise biomatter; the dose of radiation is intended to sanitize the object of biomatter.

As indicated schematically according to an exemplary embodiment, the system may comprise a set of ultraviolet LEDs as a radiation source (e.g. two UV-C LEDs configured to deliver 100 mW total at a wavelength of 275 nm); the radiation source may be configured to deliver output for a 60-second cycle time with the object at 15 cm (e.g. intended to provide greater than 99.9 percent (log 3) reduction in biomatter (e.g. virus/bacteria) or with a 120-second cycle time intending a 99.99 percent reduction in biomatter. The system may comprise a push-button "on" switch and an "override" switch, intended to cut off and indicate a fault condition if the door/cover is opened (e.g. glovebox switch to override and turn the system off if the door/cover and/or latch/closure is detected to be open). The indicator of the control panel for the user interface may comprise a visible signal such as from a LED light arrangement (e.g. LED lights on button to alert of status, such as blinking pattern when active and solid when complete) and/or an audible signal such as from a speaker/buzzer (e.g. sound tone to transmit every five seconds while cycle is active in operation, such as one second tone and four seconds silent until the cycle is completed). As indicated schematically, a fault condition or an interrupt can be indicated at the user interface/control panel with an audible signal and/or a visible signal. After a fault condition is indicated, correction of a fault (e.g. verification of door/cover closure, latch engagement, etc.) may be detected as to allow reset or restart/initiation of the cycle to provide the dose of radiation to the object.

As indicated schematically according to an exemplary embodiment in FIGS. 2A-2C, 3A-3C, 4A-4B, 27A-27B, 28A-28C, 29, 30A-30B, 31A-31B and 32A-32D, implementation and operation of the system and method to administer ultraviolet radiation/light to an object (e.g. from a radiation/light source, module, etc.) may comprise interaction/connectivity of the control system with a safety system (e.g. comprising sensors, switches, other source inputs, etc.) as well as with a user interface shown as implemented through a control panel (e.g. comprising operator control and indicators, etc.). As indicated schematically in FIGS. 32A-32D, operation of the system/method with the control system (e.g. with control program) may comprise the steps of selecting/setting the cycle (e.g. with a standard control program, with a selectable control program, etc.) and then a system/status check (e.g. with input from sensors such as for door/cover closure, presence of object, etc.) and then initiating of the set/selected cycle for administration of the dose of radiation/light to the object; during operation, the safety system may conduct monitoring and/or error detection (e.g. with input from sensors such as for door/cover closure, presence of object, additional user input such as to interrupt the cycle, etc.) and an error such as a fault condition may produce a fault signal (e.g. door/cover fault, latch/closure fault, redundant subsystem fault, object not present fault, etc.) or an input/interrupt may product a terminate signal; each signal may be indicated at the user interface (along with any other audible and/or visible status signal from the control system); in the absence of a fault condition or interrupt the system will apply radiation/light for the selected/set cycle (e.g. in a dose for the object) and provide the audible and/or visible status signal until the cycle is completed (e.g. cycle time, dose of radiation, etc.); when the cycle is completed an audible and/or visible status signal will be provided. At completion of the cycle, the object can be removed from the compartment after having been provided the dose of radiation and/or another cycle may be initiated to apply an additional dose of radiation to the object. A fault/interrupt signal will indicate that the cycle to administer the dose of radiation has not been completed (e.g. the object has not been administered the dose of radiation intended to sanitize the object of biomatter); a fault/interrupt signal may signify or indicate an issue with the door/cover, with the latch/closure, with the object, etc.; the user interface may present an indicator relating to the fault/interrupt signal (e.g. to inform and/or facilitate next actions by the vehicle occupant).

As indicated in FIGS. 3A-3C, 31A-31B and 32A-32D, in operation of the system/method to administer a dose of radiation to an object, each signal for operation/status and/or for fault/interrupt may be provided at the user interface according to the control program; the cycle for operation may be provided according to the control program to comprise a cycle time and or other parameters (e.g. intensity, duration, etc.) as set or selected; the control program may operate using data from the control system (e.g. including system memory, network data, etc.) to operate the module to administer the dose of radiation for the object; the dose of radiation is intended to sanitize the object of biomatter on the object (e.g. with set/selected dose as may be based on data relating to the biomatter, type of biomatter, object, type of object, user input, etc.).

Exemplary Embodiments—A

According to an exemplary embodiment as shown in FIGS. 1C, 2A-2C, 3A-3C, 4A-4B, 6A-6D, 7A-7F, 8A-8F, 9A-9F, 10A-10F, 11A-11B, 12, 13A-13F, 14A-14F, 15A-15F, 16A-16F, 17A-17F, 18A-18F, 19A-19F, 20A-20F, 25, 26, 27A-27B, 28A-28C, 30A-30B, 31A-31B and 32A-32D, a component for a vehicle interior configured to administer a dose of light from a module providing a light source directed to an object may comprise a base configured to provide a compartment; a cover for the base; and a control panel configured to provide a user interface; the light source may be configured to administer the dose of light to the object; the user interface may be configured for operation of the module. The dose of light may comprise ultraviolet radiation; the cover may be moveable from a closed position to an open position relative to base. The component may comprise a sensor configured to detect whether the cover may be in the closed position. The compartment may be configured to contain the object and the light source may comprise an LED arrangement configured to direct light onto the object in the compartment. The module may comprise the LED arrangement. The component may comprise a sensor configured to detect whether an object may be in the compartment. The user interface may be configured to provide a signal; the signal may comprise an audible signal and/or a light signal. The component may comprise a storage compartment, a console, a removable compartment. The control panel may be on the cover; the control panel may be separate from the base; the control panel may comprise a remote button within the vehicle interior.

According to an exemplary embodiment as shown in FIGS. 1C, 2A-2C, 3A-3C, 4A-4B, 6A-6D, 7A-7F, 8A-8F, 9A-9F, 10A-10F, 11A-11B, 12, 13A-13F, 14A-14F, 15A-15F, 16A-16F, 17A-17F, 18A-18F, 19A-19F, 20A-20F, 25, 26, 27A-27B, 28A-28C, 30A-30B, 31A-31B and 32A-32D, a component for a vehicle interior configured to administer a dose of radiation to an object may comprise a base configured to provide a compartment; a cover for the base; a module comprising radiation source; a control panel for the module configured to provide a user interface; the radiation source may be configured to administer the dose of radiation to the object; the user interface may be configured for operation of the module. The user interface may be configured to provide a signal; the signal may comprise an audible signal and/or a light signal. The radiation source may comprise a light source. The light source may comprise ultraviolet light source. The compartment may be configured to contain the object and the light source may comprise an LED arrangement configured to direct light onto the object in the compartment. The cover may be moveable from a closed position to an open position relative to the base providing access to the compartment. The component may comprise a sensor configured to detect whether the cover may be in the closed position. The module may be configured to administer the dose of radiation only when the sensor detects that the cover may be in the closed position. The compartment may comprise a removable bin for the object. The control panel for the user interface may comprise an indicator light. The control panel for the user interface may comprise a speaker. The control panel for the user interface may comprise a button. The control panel for the user interface may comprise a button adjacent to the cover. The user interface may comprise a light signal. The user interface may be presented by a transmissive light guide on the cover; the light guide may be aligned with an indicator light on the control panel when the cover may be in a closed position. The cover may comprise at least one of (a) a light guide aligned with the user interface; and/or (b) a light pipe aligned with the user interface. The radiation source may comprise an ultraviolet light source; the ultraviolet light source may comprise at least one of (a) an LED; (b) an LED lamp; (c) an LED array; (d) at least one LED; (e) a set of two LEDs; (f) a lamp installed within the base; (g) a light emitting diode installed within the base; and/or (h) a UV-C LED installed within the base. The ultraviolet light source may comprise a lamp installed within the base. The module may be mounted in the base. The base may be configured to be installed in/under an instrument panel. The control panel may comprise a button. The component may comprise a glove box; the cover may comprise a door for the glove box. The component may comprise a platform configured to position the object for access when the cover may be in the open position; the platform may be configured to position the object for administration of the dose of ultraviolet light when the cover may be in the closed position. The ultraviolet light source may comprise an upper light source and a lower light source separated from the upper light source by the platform; the platform may comprise a mesh configured to facilitate passage of light from the lower light source to the object. The base may comprise a platform for the object; the platform may comprise a shelf; the platform may comprise a first compartment for a first object and a second compartment for a second object. The component may comprise a storage compartment comprising the platform; the platform may comprise the compartment of the base. The component may comprise a control system for the module; the control system may be operated on a cycle intended to administer a dose of ultraviolet light to the object. The cover may comprise a door; the control system for the module may be operated by a method comprising the steps of (a) opening the door; (b) placing the object; (c) closing the door; (d) administering the dose of light to the object; (e) opening the door; and (f) removing the object. The object may comprise biomatter; the dose of radiation is intended to sanitize the object of biomatter.

According to an exemplary embodiment as shown in FIGS. 1C, 2A-2C, 3A-3C, 4A-4B, 6A-6D, 7A-7F, 8A-8F, 9A-9F, 10A-10F, 11A-11B, 12, 13A-13F, 14A-14F, 15A-15F, 16A-16F, 17A-17F, 18A-18F, 19A-19F, 20A-20F, 25, 26, 27A-27B, 28A-28C, 30A-30B, 31A-31B and 32A-32D, a system for a vehicle interior configured to administer a dose of radiation to an object may comprise a component comprising a base and a cover and a compartment for the object; a module comprising a radiation source operated by a control program; a control panel configured to provide a user interface in operation of the module; the user interface may comprise presentation of a signal; the radiation source may be configured to administer the dose of radiation to the object according to a control program. The radiation may comprise ultraviolet light; the radiation source may comprise an ultraviolet light source configured to administer the dose of ultraviolet light to the object. The user interface may be configured for operation of the module. The component may comprise a platform. The cover may be configured to move between a closed position and an open position. The cover may be configured to be moved to the closed position for administration of the dose of radiation. The cover may be configured to be moved to the open position relative to the base providing access to the compartment. The compartment may comprise a bin; the radiation source may be configured to direct radiation into the bin. The radiation source may comprise at least one LED. The radiation source may comprise an ultraviolet light source configured to administer a dose of ultraviolet light to the object. The base may be configured to provide the compartment. The control panel may comprise an indicator light; the user interface may comprise a light transmissive light guide on the cover; the light guide may be aligned with the indicator light on the control panel when the cover may be in the closed position. The base may comprise the user interface; the cover may comprise at least one of (a) a light guide aligned with the user interface; and/or (b) a light pipe aligned with the user interface. The radiation source may comprise at least one of (a) an LED; (b) an LED lamp; (c) an LED array; (d) at least one LED; (e) a set of two LEDs; (f) a lamp installed within the base; (g) a light emitting diode installed within the base; and/or (h) a UV-C LED installed within the base. The radiation source may comprise a lamp installed within the base. The module may be mounted in the base; the base may be configured to be installed in/under an instrument panel. The control panel may comprise a button. The component may comprise a control system for the module; the control system may be operated according to the control program on a cycle intended to administer a dose of ultraviolet light to the object. The cover may comprise a door; the control system for the module may be operated by a method comprising the steps of (a) opening the door; (b) placing the object; (c) closing the door; (d) administering the dose of light to the object; (e) opening the door; and (f) removing the object. The signal of the user interface may comprise at least one of a light signal and/or an audible signal; the light signal may be provided at the control panel; the audible signal may be provided at the control panel. The signal of the user interface may be provided by the control program of the module. The signal may comprise feedback. The control panel may comprise an operator control configured to operate the module of the component; the operator control may be configured to select an operation cycle for the module; the operation cycle may comprise administration of the dose of radiation to the object. The signal may comprise a completion signal for the module. The completion signal may be configured to indicate completion of an operation cycle for the module. The signal may comprise a fault signal for the module. The signal may comprise an interrupt signal for the module. The signal may be provided by an indicator; the indicator may comprise a sound transmitter; the indicator may comprise a light. The light may comprise a light-transmissive element to provide illumination. The radiation source may comprise an LED arrangement configured to provide at least 100 mW of LED light; the LED light comprise a wavelength of about 275 nm. The LED arraignment may comprise two LED lights; each LED light may comprise a 50 mA LED configured to provide at least 100 mA total UVC energy. The control program may be configured to operate the module with an operation cycle. The operation cycle may comprise a 60 second cycle time. The compartment may be configured to place the object at about 15 cm from the radiation source; the radiation source may be configured to provide at least a 3 log reduction in virus/bacteria on the object; the radiation source may be configured to provide at least a 99.9 percent reduction in active biomatter on the object. The module may be configured to provide 100 mA of UVC power; the operation cycle may comprise a cycle time of about 120 seconds. The control panel may comprise an override switch. The component may comprise a glovebox comprising a switch configured to turn off the radiation source; the cover may comprise a door for the glove box and the control program may be configured to turn off the radiation source if the switch detects that the door is open. The control panel may comprise a push button to activate the module. The control panel may comprise a remote button to activate the module. The remote button may be within the vehicle interior. The remote button may be within the centerstack of the vehicle interior. The user interface may comprise LED lights. The user interface may comprise a button. The signal from the user interface may be configured to indicate of status of operation of the module. The signal may comprise a blinking light when in operation during administration of the dose of radiation and a solid light administration of the dose of radiation may be completed. The signal may comprise a light that may be off when the module may be not in operation. The signal may comprise a sound during administration of the dose of radiation. The signal may comprise a sound to indicate completion of administration of the dose of radiation. The signal may comprise an alert in a fault condition. The signal may comprise an audible tone every 5 seconds during administration of radiation. The signal may comprise a buzzer with transmit with a pattern. The pattern may comprise a tone every 1 second when in operation and for 4 seconds when completed. The component may comprise at least one of a storage compartment, a glove box, a console, a floor console, an overhead console, a trim panel, and/or a door panel. The object may comprise biomatter; the dose of radiation may be intended to sanitize the object of biomatter.

According to an exemplary embodiment as shown in FIGS. 3A-3C, 4A-4B, 31A-31B and 32A-32D, the system may be operated according to a method comprising the steps of: (a) setting a cycle for operation of the system; (b) initiating the cycle for operation of the system; (c) monitoring the system in operation; and (d) providing the signal at the user interface; monitoring the system in operation may comprise determining status of the system; operation of the system may comprise at least one of applying the dose of radiation to the object or ending the cycle if a fault is detected; the signal may be provided to indicate status of the system. The status of the system may be determined according to the control program. Ending the cycle if a fault is detected may comprise an interrupt of operation; ending the cycle may comprise not applying the dose of radiation to the object. The signal may comprise a completion signal when the cycle of operation is completed. The signal may comprise an operation signal during operation of the system. The signal may comprise a fault signal if the cycle of operation is not completed. Setting the cycle may comprise selection of the cycle at the control panel. The component may comprise a sensor to indicate status; and monitoring the system in operation may comprise monitoring status indicated by the sensor. Status may comprise presence of the object in the compartment; status may comprise status of the cover. The cover may comprise a door movable from an open position to a closed position; status may comprise detection of whether the door is in an open position; when the door is in an open position the step of monitoring the system in operation may comprise indicating a fault status and providing a fault signal. Monitoring the system may comprise ending the cycle by an interrupt if the fault status is not corrected. Monitoring the system may comprise ending the cycle if an interrupt status is detected. Interrupt status may be provided at the control panel.

As shown schematically in FIGS. 3A-3C, 4A-4B, 31A-31B and 32A-32D, the signal may be provided according to the cycle for operation may be provided according to the control program. The control program may comprise a cycle time. The control program may operate using data from a control system. The control program may be configured to operate the module to administer the dose of radiation to the object; the object may comprise biomatter; the dose of radiation is intended to sanitize the object of biomatter. See also FIGS. 25 and 26.

Exemplary Embodiments—B

Referring to FIGS. 1A-1C and 2A-2C, a vehicle V is shown with an interior I comprising components such as an instrument panel IP and a system/component C shown as a compartment/bin BN with a pivoting cover CV and a platform/shelf PL for an article AC or materials MT. As indicated in FIGS. 2A-2C and 4A-4B, the component may comprise a system with a module M configured to administer radiation such as ultraviolet light from a light source to the article AC on the platform PL in the bin BN; the system of the component may comprise a control panel CP configured to present a user interface UI providing instrumentation and/or control elements (e.g. such as button BT, indicator/icon IC, etc.) for operation/monitoring of the module M. See also FIGS. 3A-3C (showing system arrangement comprising module/controller operable with data/control program and with light source/LED, fan, etc.). As shown schematically in FIGS. 4A-4B, the system/module M may comprise a light source LS shown as comprising an LED arrangement (e.g. LED configured to administer ultraviolet light for effect). Compare FIG. 4A (dual/multi-LED) with FIG. 4B (single LED).

As indicated schematically according to an exemplary embodiment in FIGS. 7A-7F and 8A-8F, the component/system may be configured to administer treatment (e.g. dose) of ultraviolet light UV from the module M providing the light source LS directed to an object/article AC (e.g. item shown representationally as mobile device) placed in the bin/compartment BN. See also FIGS. 9A-9F and 10A-10F. The component may comprise a base configured to provide the compartment BN and a cover CV moveable from a closed position to an open position providing access to the compartment and a user interface UI (e.g. configured to provide instrumentation and/or control) for the module M; as indicated, when the cover/door is closed, the light source/LED arrangement of the module may be operated to administer the UV light to the article (e.g. according to a process, cycle, program, algorithm, etc. in a dose intended to neutralize biomatter such as may be upon the surface of the article within the range of the UV light).

According to an exemplary embodiment indicated schematically in FIGS. 3A-3B, 11A-11B and 12, the light source/LED arrangement of the system/module M may be configured to administer the dose of ultraviolet light UV to the object/article in the compartment by operation of the user interface/control panel when the cover is in the closed position; indication may be provided at the user interface when the cover is open to remove the object/article from the compartment; as indicated schematically, the user interface may be configured for operation and/or monitoring of the module. See also FIGS. 27A-27B (user interface comprising illuminated indicators shown as light-transmissive elements/light guides LG on the cover CV to provide illumination from indicators IC on control panel CP).

As indicated schematically in FIGS. 13A-13F and 14A-14F, the component may comprise a platform PL shown as a movable tray for the article to be placed for the light source/LED arrangement of the module M in the compartment; the platform PL may comprise a set of compartments with a frame FR and/or a mesh/net arrangement. See FIGS. 19A-19F, 21, 22, 23 and 24. The platform/tray may comprise the control panel for the user interface. See FIGS. 15A-15F (e.g. control button/element for operation of the platform/tray and/or for the module). As indicated schematically in FIGS. 16A-16F, the system/module may comprise a switch SW to indicate the state/position (e.g. engagement, disengagement) of the platform/tray PL; controller may use a signal from switch SW (and/or a signal from the cover/door to indicate the closed position) to determine whether to operate the module to administer UV light within the compartment.

As indicated schematically, the component/system may comprise a control system for the module operated by a method comprising the steps of (a) opening the door; (b) placing the object; (c) closing the door; (d) administering the dose of UV light to the object; (e) opening the door; and (f) removing the object. The article/object may comprise biomatter; the dose of UV light is intended to sanitize the object of biomatter.

Figure 25:
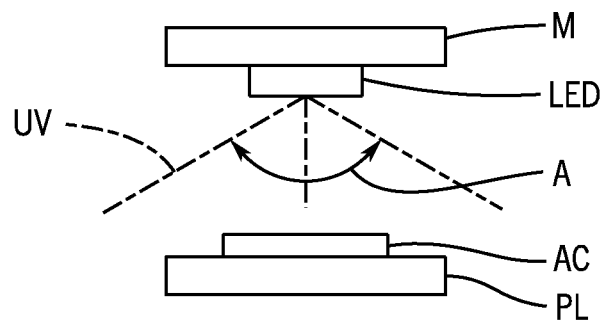
FIG. 25 is a schematic section view of a component/system for treatment/radiation of an article/object in a vehicle interior according to an exemplary embodiment.
Figure 26:
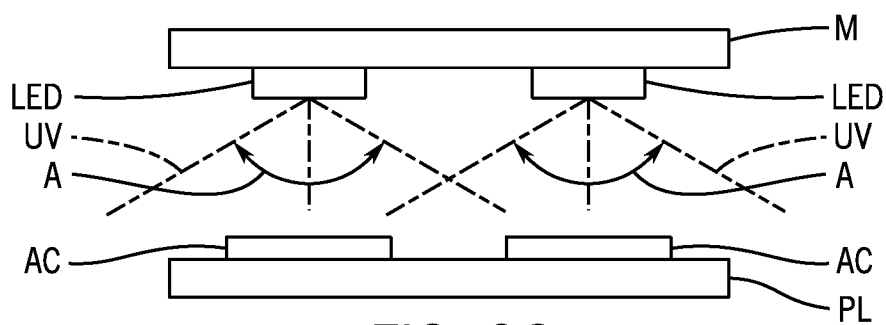
FIG. 26 is a schematic section view of a component/system for treatment/radiation of an article/object in a vehicle interior according to an exemplary embodiment.
Figure 27A:
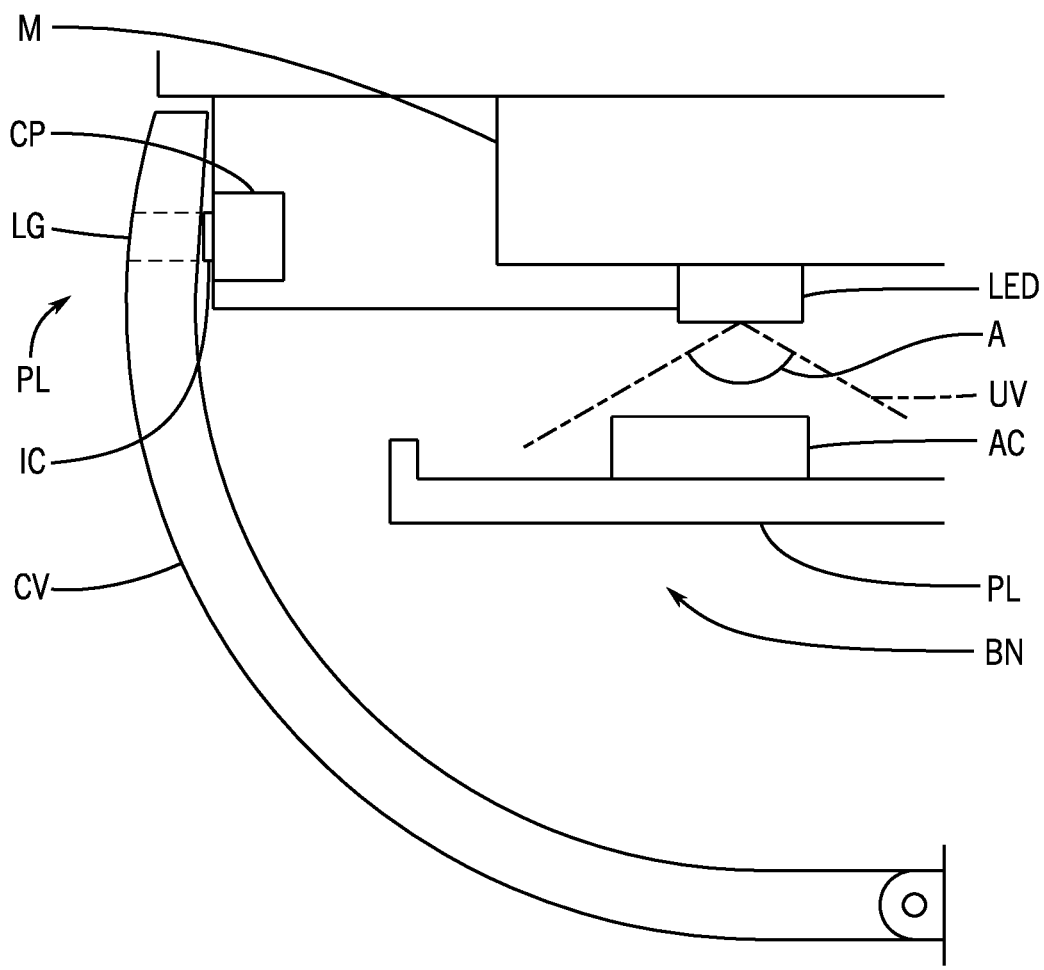
FIG. 27A is a schematic partial section view of a component/system for treatment/radiation of an article/object in a vehicle interior according to an exemplary embodiment.
Figure 27B:
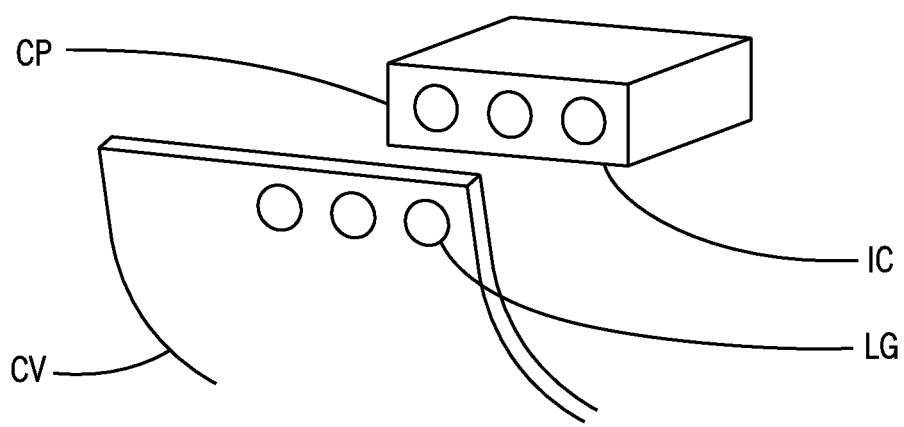
FIG. 27B is a schematic partial perspective view of a component with cover and control panel for module of the system to administer treatment/radiation to an article/object in a vehicle interior according to an exemplary embodiment.
Figure 29:
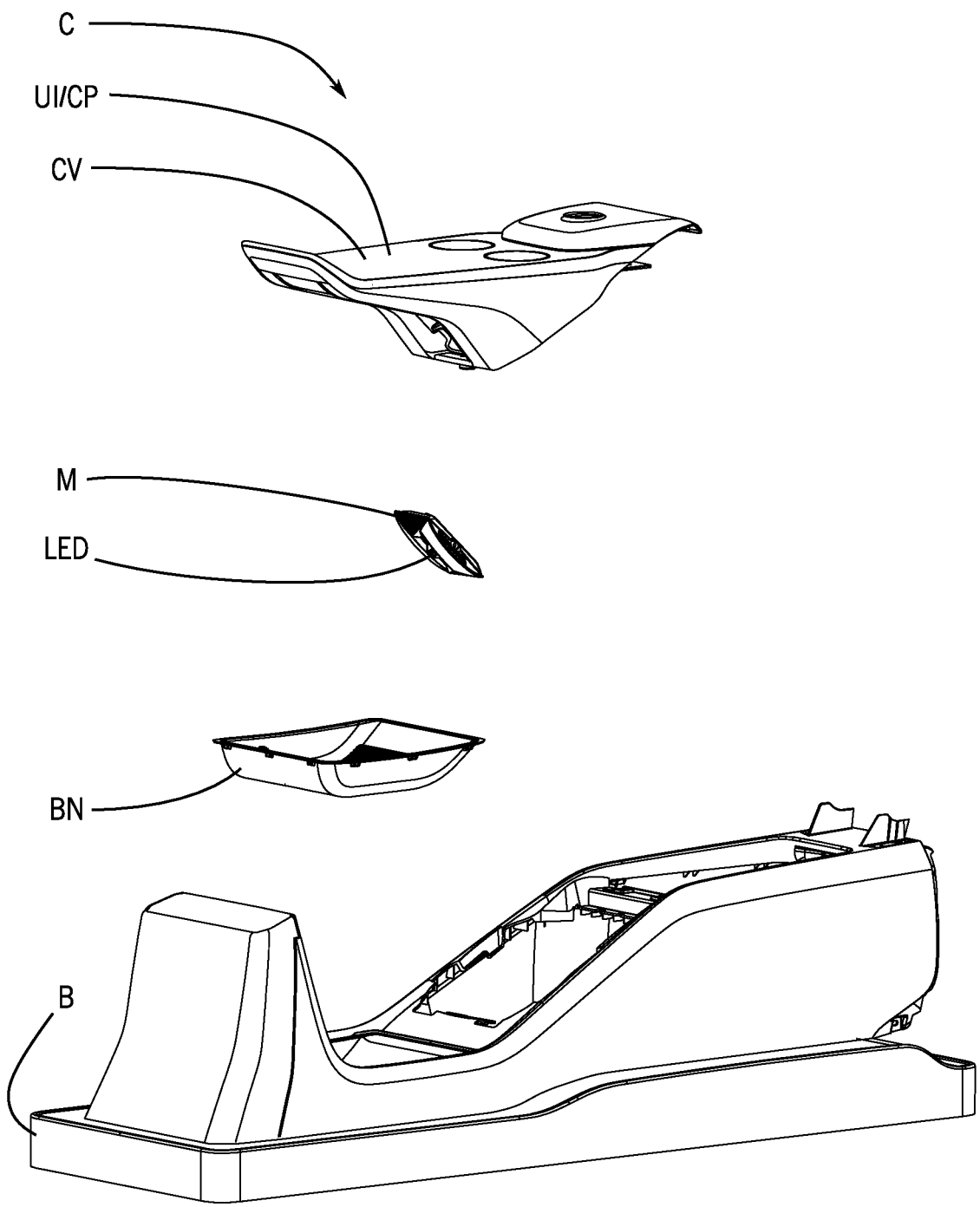
FIG. 29 is a schematic exploded perspective view of a component/system for treatment/radiation of an article/object in a vehicle interior according to an exemplary embodiment.
Figure 30A:
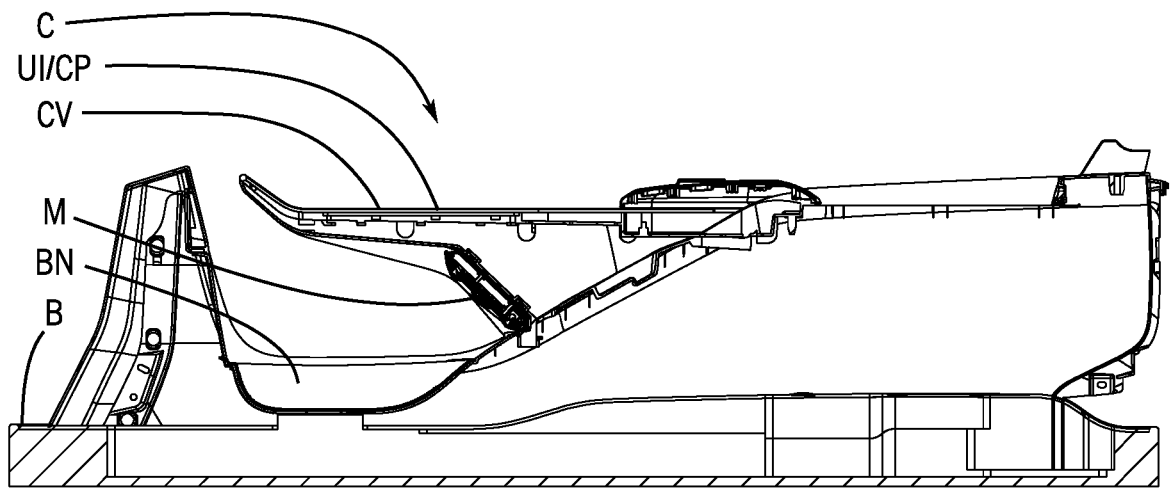
FIGS. 30A and 30B are schematic side elevation section views of a component/system for treatment/radiation of an article/object in a vehicle interior according to an exemplary embodiment.
Figure 30B:
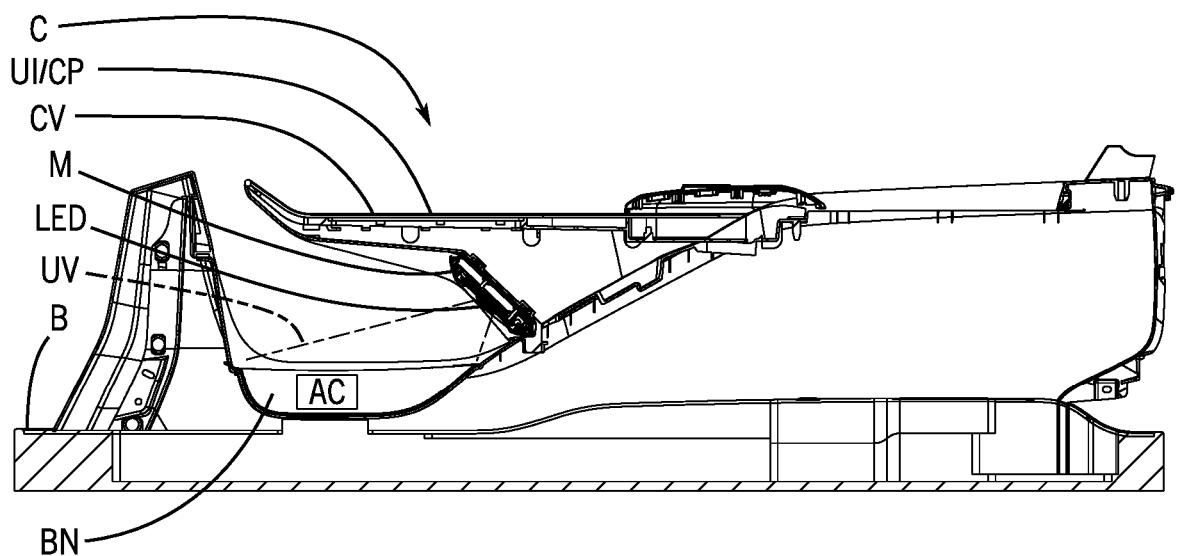
Figure 31A:
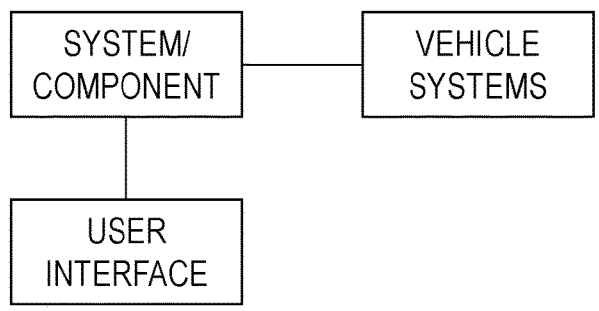
FIGS. 31A and 31B are schematic block diagrams of a component/system for treatment/radiation of an article/object in a vehicle interior according to an exemplary embodiment.
Figure 31B:
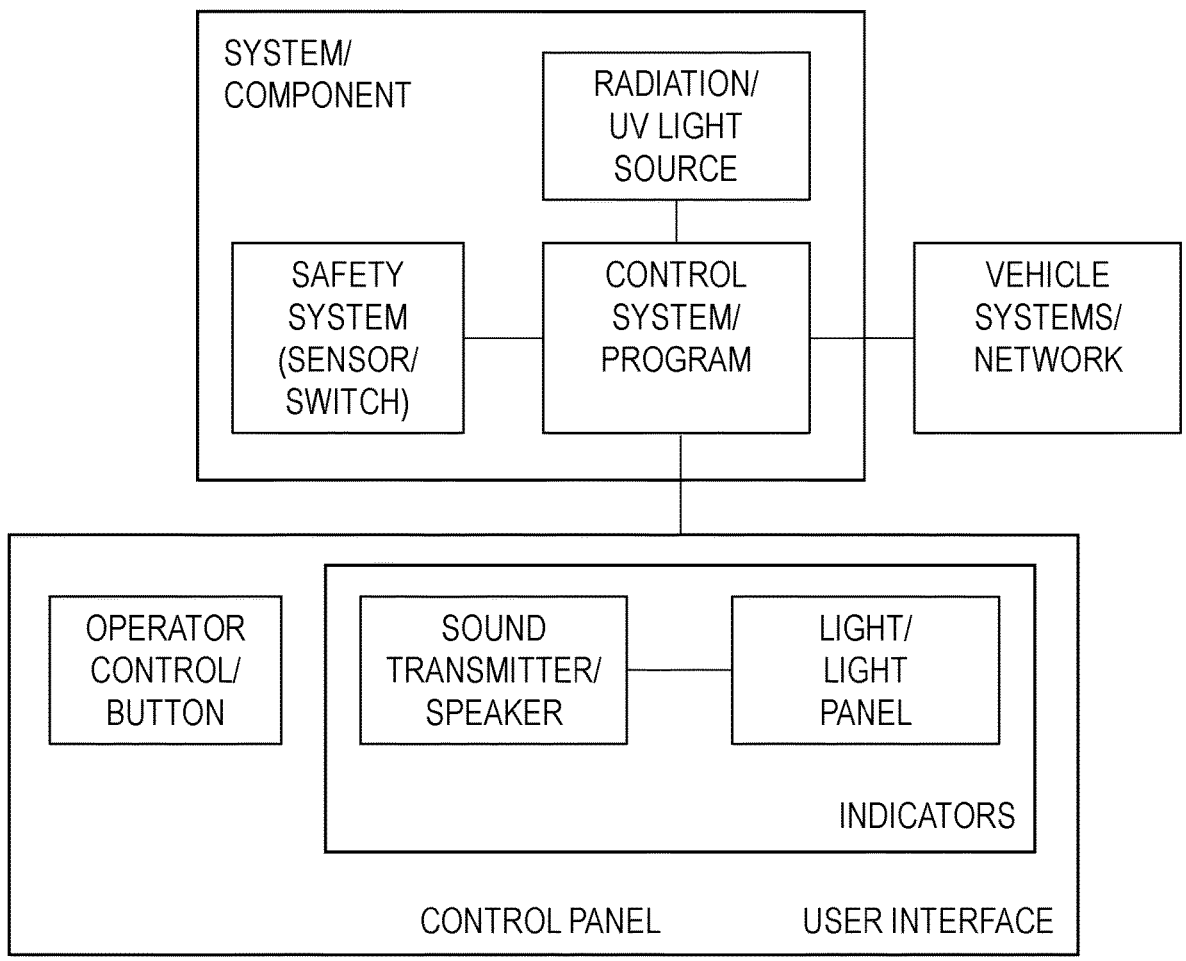
Figure 32A:
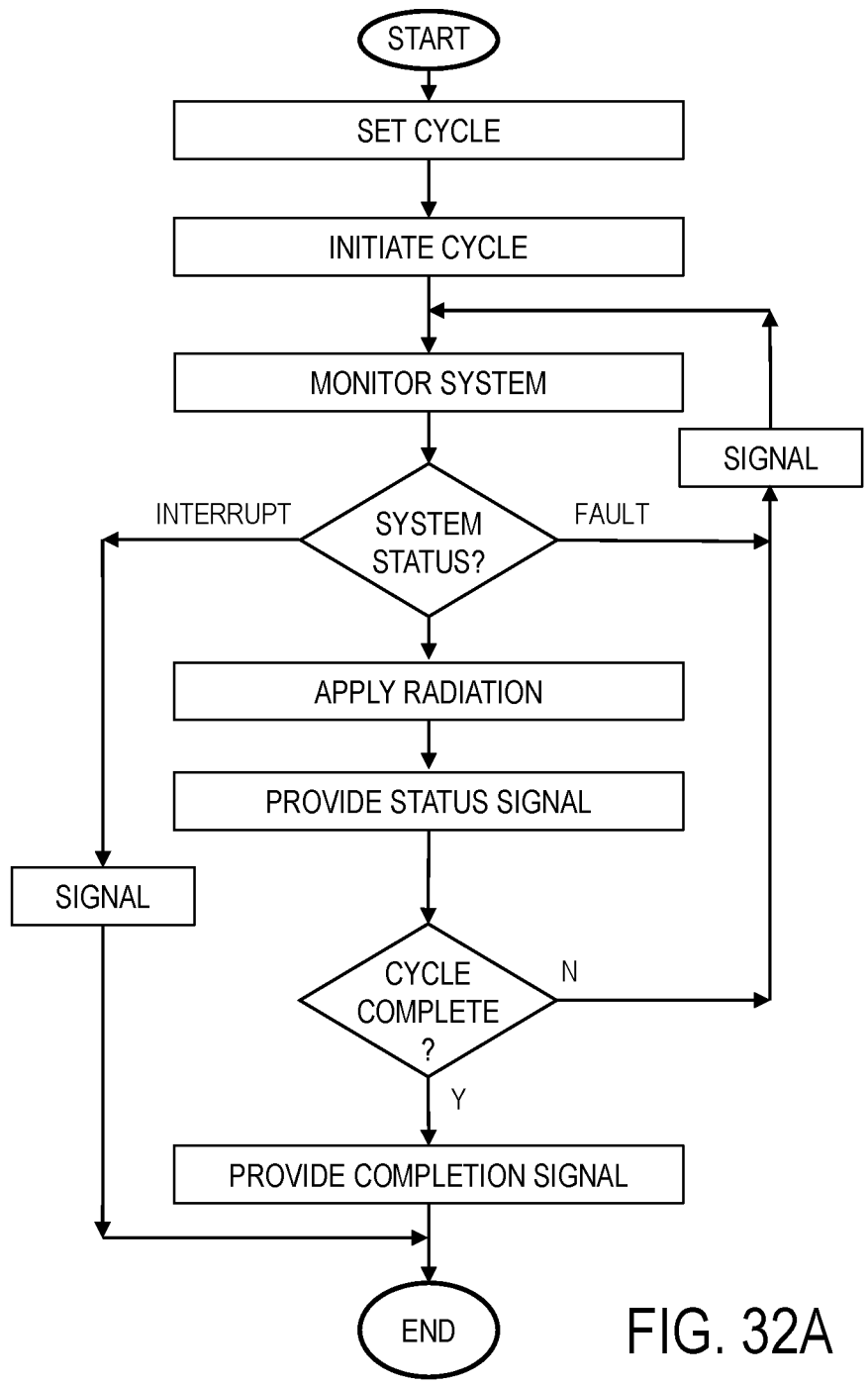
Figure 32D:
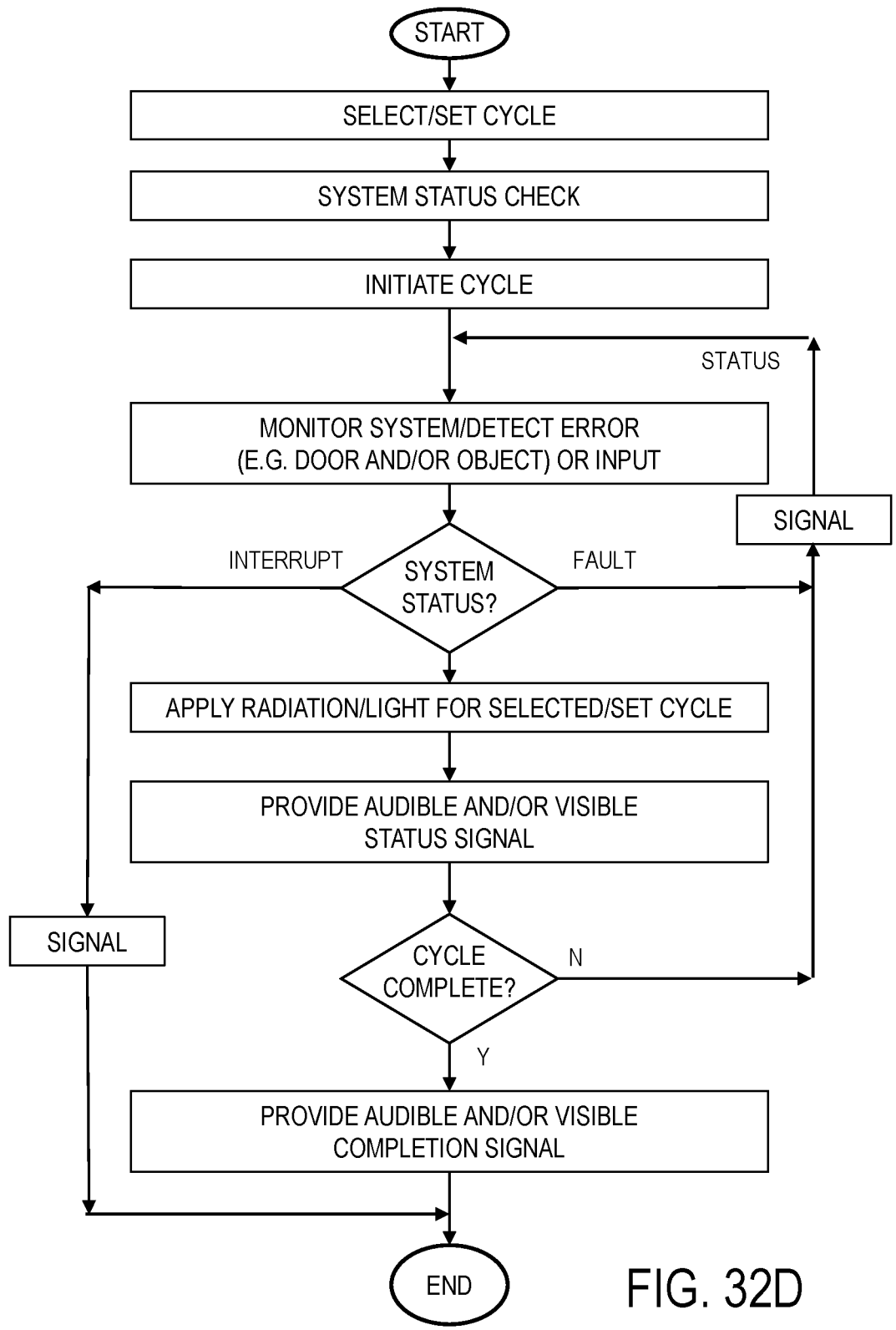

As indicated schematically in FIGS. 25 and 26, the LED arrangement of the module M may comprise a single LED or multiple LEDs; as indicated schematically, the UV light from the LED arrangement may comprise an angle A (e.g. a cone of 115 to 120 degrees); a multiple LED arrangement may provide wider coverage than a single LED arrangement for effective dosage/administration of UV light to articles/objects on the platform in the compartment of the component.

As indicated schematically, the system/component C may comprise a module M comprising an irradiation system to administer a dose of ultraviolet light UV for the article and a controller; the controller may be operated at a user interface UI provided by a control panel CP and a control system; the radiation/irradiation system of the component C may be operated by the controller and provide instrumentation and/or control at the user interface UI. See FIGS. 1C, 2A-2C, 3A-3C, 4A-4B, 6A-7B, 11A-11B, 12, 13A-13F, 15A-15F, 19A-19F, 25, 26, 27A-27B, 28A-28C, 29, 30A-30B, 31A-31B and 32A-32D. As indicated schematically in FIGS. 1C, 2A-2C, 3A-3C, 4A-4B, 11A-11B, 12, 13A-13F, 15A-15F, 19A-19F, 25, 26, 27A-27B, 30A-30B, 31A-31B and 32A-32D, the module with irradiation system may be configured to administer the dose of UV light for the article; the controller for the module may be operated by the control panel and a control system; the radiation/irradiation system may be operated by the controller to provide instrumentation and/or control at the user interface.

According to an exemplary embodiment, the system/module may be configured with a sensor-detector arrangement to detect that the cover/door has been moved to the closed position and/or that an article is present and/or that the platform is in an engaged position and/or to indicate that the dose of UV light has been administered to the article and/or to indicate if there has been a fault or interrupt detected in operation (e.g. without administration of UV light to the article or the system/module is inoperable, requires service, etc.). See FIGS. 32A-32D.

According to an exemplary embodiment as indicated schematically in FIGS. 15A-15F and 16A-16F, the operation of the module to administer a dose of UV light to the article on the platform may be actuated by an occupant of the vehicle at a button on a control panel; position of the platform may also be actuated by a controller (e.g. at the control panel) with a mechanism (e.g. spring release, etc.).

Figure 20A:
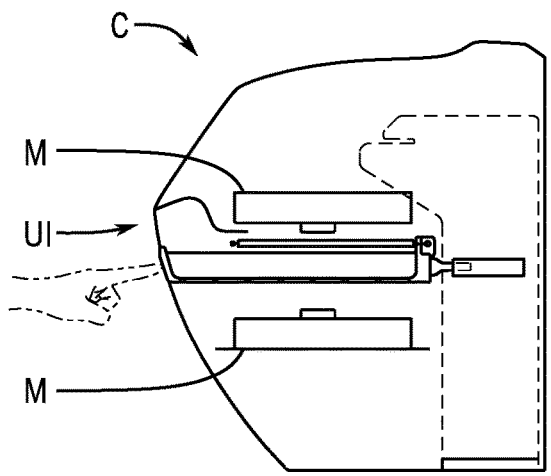
FIGS. 20A through 20F are schematic side views of a component/system for treatment/radiation of an article/object in a vehicle interior according to an exemplary embodiment.
Figure 20B:
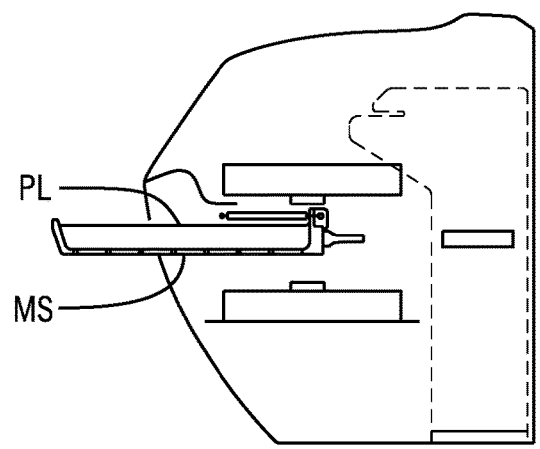
Figure 20C:
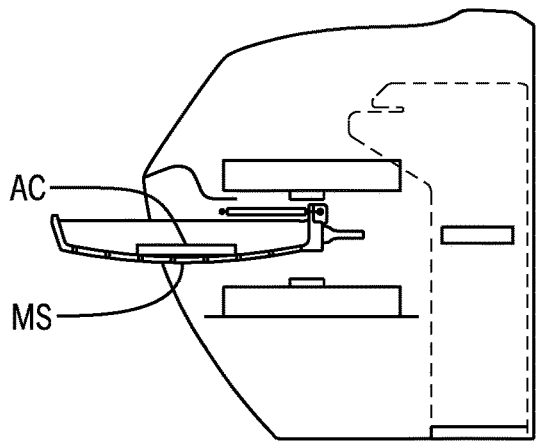
Figure 20D:
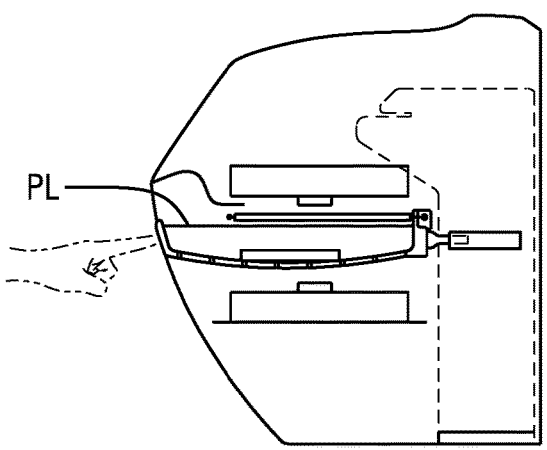
Figure 20E:
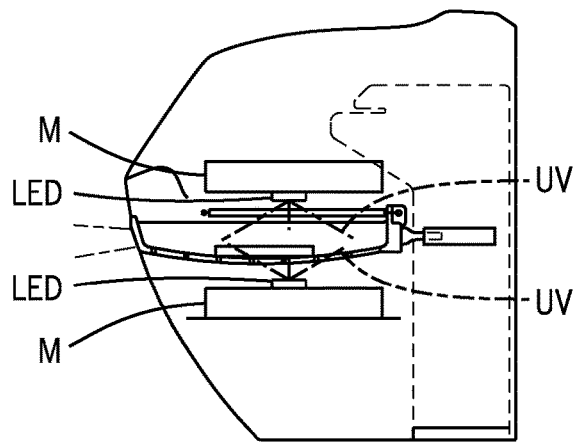
Figure 20F:
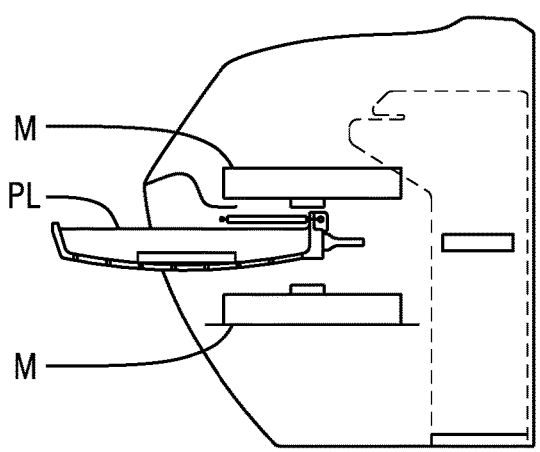
Figure 21:
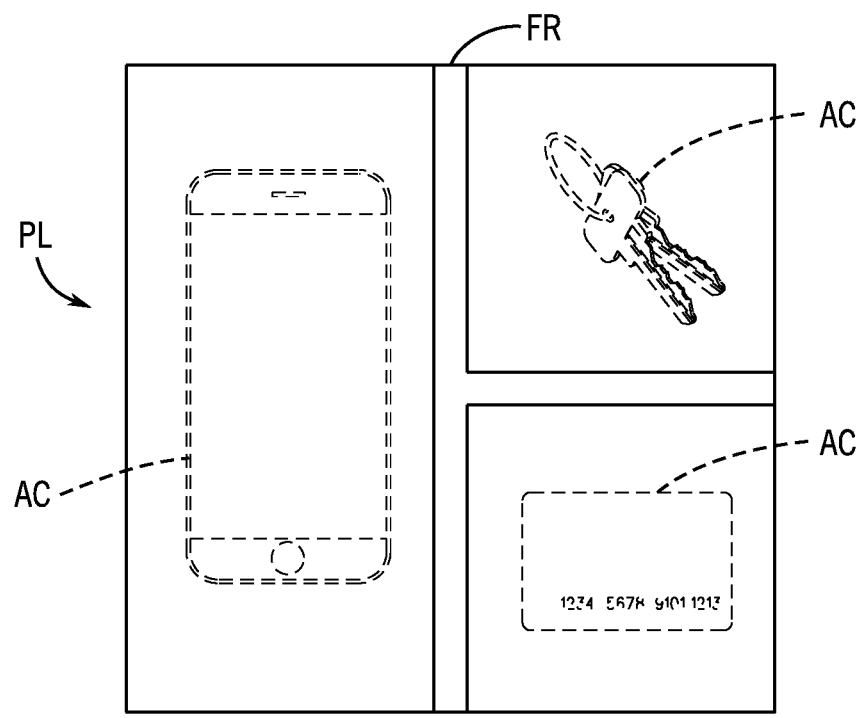
FIG. 21 is a schematic plan view of a platform of a component/system for treatment/radiation of an article/object in a vehicle interior according to an exemplary embodiment.
Figure 22:
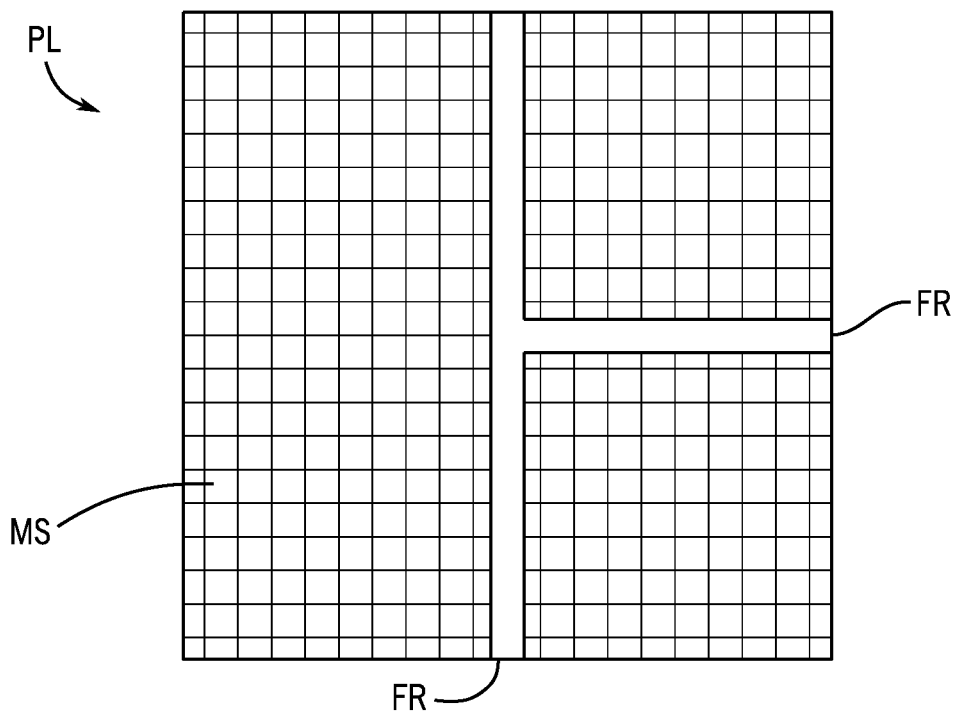
FIG. 22 is a schematic plan view of a platform of a component/system for treatment/radiation of an article/object in a vehicle interior according to an exemplary embodiment.
Figure 23:
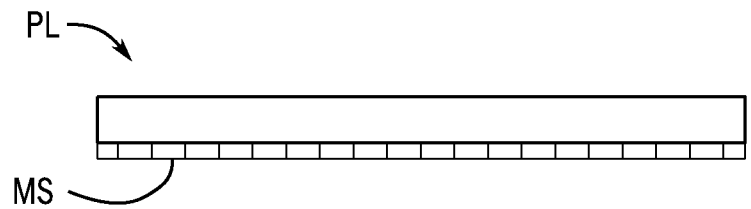
FIG. 23 is a schematic section view of a platform of a component/system for treatment/radiation of an article/object in a vehicle interior according to an exemplary embodiment.
Figure 24:
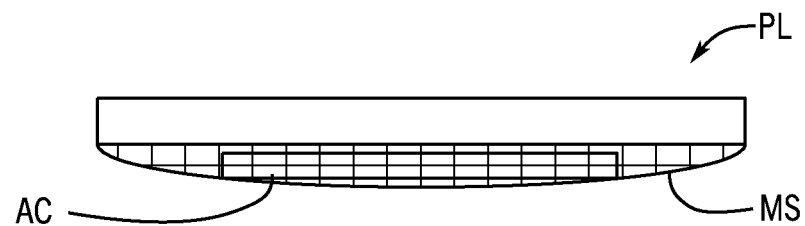
FIG. 24 is a schematic section view of a platform of a component/system for treatment/radiation of an article/object in a vehicle interior according to an exemplary embodiment.

According to an exemplary embodiment as indicated schematically in FIGS. 19A-19F and 20A-20F, the operation of the module to administer a dose of UV light to the article on the platform may be actuated by manual positioning of the platform from the extended position (see FIGS. 20B-20C) to the retracted position (see FIGS. 20D-20E) (e.g. a position as detected by a switch and/or sensor/detector); the platform may also be configured to be moved to the extended position (e.g. by release of a latch, spring action, etc. for removal of the article) at the direction of the controller after completion of the administration/treatment with UV light (see FIG. 20F). The system/component C may comprise a sensor/switch SW; spring action for the platform PL may be provided by a spring SG; the latch LP for the cover CV of the component C may comprise a push-push latch (e.g. with a plunger/striker SK), as indicated schematically in FIGS. 14A-14F, 16A-16F, 17A-17F and 18A-18F.

Exemplary Embodiments—C

According to an exemplary embodiment as shown schematically in FIGS. 1A-1C, 2A-2C, 3A-3C, 4A-4B, 6A-6D, 7A-7F, 8A-8F, 9A-9F, 12, 14A-14F, 15A-15F, 17A-17F, 18A-18F, 19A-19F, 20A-20F, 25, 26, 27A-27B, 28A-28C, 30A-30B, 31A-31B and 32A-32D, a vehicle V comprising an interior I may comprise a component C configured to administer a dose of ultraviolet light UV from a module M providing an ultraviolet light source LS/LED directed to an object such as article AC. As indicated schematically, the system/component C may comprise a module M comprising an irradiation system to administer a dose of ultraviolet light UV for the article and a controller; the controller may be operated at a user interface UI provided by a control panel CP and a control system; the radiation/irradiation system of the component C may be operated by the controller and provide instrumentation and/or control at the user interface UI. See FIGS. 1C, 2A-2C, 3A-3C, 4A-4B, 6A-7B, 11A-11B, 12, 13A-13F, 15A-15F, 19A-19F, 25, 26, 27A-27B, 28A-28C, 29, 30A-30B, 31A-31B and 32A-32D.

As indicated schematically in FIGS. 1C, 2A-2C, 3A-3C, 4A-4B, 12, 14A-14F, 15A-15F, 17A-17F, 18A-18F, 19A-19F, 20A-20F, 25, 26 and 27A-27B, the component C may comprise a base B; a tray PL coupled to the base and comprising a compartment BN and a user interface UI such as presented by a control panel CP. The ultraviolet light source may be configured to administer the dose of ultraviolet light to the object in the compartment. The user interface may be configured for operation of the module. The tray may be configured to move relative to the base from a retracted position for administration of the dose of ultraviolet light to an extended position for access. The component may comprise a mechanism configured to (a) retain the tray in the retracted position (b) guide movement of the tray from the retracted position to the extended position. The mechanism may be configured to move the tray from the retracted position to the extended position after administration of the dose of ultraviolet light. The mechanism may comprise (a) a latch LP configured to retain the tray in the retracted position and (b) an actuator configured to unlatch the tray after administration of the dose of ultraviolet light. The latch may comprise a push-push latch (e.g. with a plunger/striker SK), as indicated schematically in FIGS. 14A-14F, 16A-16F, 17A-17F and 18A-18F. The mechanism may be configured to move the tray from the retracted position to the extended position in response to an external force applied to the tray. The mechanism may comprise a motor configured to move the tray between the retracted position and the extended position; the motor may be configured to move the tray from the retracted position to the extended position after administration of the dose of ultraviolet light. The ultraviolet light source may comprise an upper lamp and a lower lamp separated from the upper lamp by the tray. The tray may comprise a mesh MS configured to facilitate passage of light from the lower lamp to the article. The component may comprise a cover CV coupled to the base; the cover may be configured to move from (a) an upward position to cover the tray to (b) a lowered position to uncover the tray. The cover may be configured to prevent movement of the tray when the cover is in the upward position; the cover may be configured to allow movement of the tray when the cover is in the lowered position. The component may comprise a harness/wire harness WH for the cover; the cover may comprise the user interface. At least one of (a) the base; and/or (b) the tray may comprise the user interface; the cover may comprise a light guide LG aligned with the user interface. The component may comprise a bin BN coupled to the base comprising a receptacle into which an article can be stowed and configured to move relative to the base in an opening direction from a closed position to an open position for access; the ultraviolet light source may be configured to administer a dose of ultraviolet light to the article in the receptacle. The component may comprise (a) a cover CV configured to cover the tray and the bin and (b) a mechanism; the mechanism may be configured to guide movement of the cover and the bin. The mechanism may comprise (a) a latch configured to retain the bin in the closed position and (b) a gear and a rack configured to guide movement of the cover and the bin. The tray may be configured to move between the retracted position and the extended position when the bin is in the closed position and the open position. The component may comprise a button/release BR; the mechanism may be configured to move the cover and the tray in response to actuation of the button. The component may comprise a first button and a second button. The first button may be configured to (a) move the cover relative to the bin from the upward position to the lowered position to uncover the tray and (b) move the tray relative to the base from the retracted position to the intermediate/extended position for access. The first button may be configured to move the tray relative to the base from the retracted position to the intermediate/extended position for access when the first button is pressed after the second button. The second button may be configured to move the bin relative to the base from the closed position to the open position for access. The second button may be configured to (a) move the cover from the upward position to the lowered position and (b) move the bin relative to the base from the closed position to the open position for access. The ultraviolet light source may comprise at least one of (a) a lamp installed within the base; (b) a light emitting diode installed within the base; and/or (c) a UV-C LED installed within the base. The module may be mounted in the base. The component may comprise a platform PL in the base for the object. The user interface may comprise a control panel CP. The component may comprise a control system for the module. The control system may be operated on a cycle intended to administer a dose of ultraviolet light to the object. The control system for the module may be operated by a method comprising the steps of (a) extending the tray; (b) placing the object; (c) retracting the tray; (d) administering the dose of light to the object; (e) extending the tray; and (f) removing the object. The component may comprise a glove box. The base may be configured to be installed in/under an instrument panel. The object may comprise biomatter; the dose of ultraviolet light may be intended to sanitize the object of biomatter.

According to an exemplary embodiment as shown schematically in FIGS. 1C, 2A-2C, 3A-3C, 4A-4B, 6A-6D, 7A-7F, 8A-8F, 9A-9F, 12, 14A-14F, 15A-15F, 17A-17F, 18A-18F, 19A-19F, 20A-20F, 25, 26, 27A-27B, 31A-31B and 32A-32D, a component C for a vehicle interior configured to stow an article may comprise a base; a bin BN coupled to the base comprising a receptacle into which the article can be stowed and configured to move relative to the base in an opening direction from a closed position to an open position for access; a tray coupled to the base and configured to move relative to the base from a retracted position to an intermediate/extended position for access; a cover CV coupled to the base configured to move from an upward position to cover the tray to a lowered position to uncover the tray; and a module M coupled to the base providing an ultraviolet light source. The bin may be configured to move relative to the base from the closed position to the open position when the tray is in the retracted position and the intermediate/extended position. The ultraviolet light source may be configured to administer a dose of ultraviolet light to the article. The tray may be configured to move from the retracted position to the intermediate/extended position when the bin is in the closed position and the open position. The tray may be configured to move relative to the base from the intermediate/extended position to an extended position. The component may comprise a spring; the spring may be configured to move the tray from the extended position to the intermediate/extended position. The tray may be configured to move from the intermediate/extended position to the extended position when the bin is in the closed position and the open position. The component may comprise a mechanism configured to (a) latch the tray to the base in the retracted position and (b) unlatch the tray from the base. The component may comprise a mechanism configured to (a) retain the bin in the closed position (b) guide movement of the bin from the closed position to the open position and (c) guide movement of the cover from the upward position to the lowered position. The component may comprise a mechanism configured to (a) retain the tray in the retracted position and (b) move the tray from the retracted position to the intermediate/extended position. The component may comprise a mechanism configured to (a) retain the tray in the retracted position (b) guide movement of the tray from the retracted position to the intermediate/extended position. The mechanism may be configured to move the tray from the retracted position to the intermediate/extended position after administration of the dose of ultraviolet light. The component may comprise a user interface UI configured for operation of the module. At least one of (a) the base; and/or (b) the tray may comprise the user interface; the cover may comprise a light guide LG aligned with the user interface. The component may comprise a harness/wire harness WH for the cover; the cover may comprise the user interface.

According to an exemplary embodiment as shown schematically in FIGS. 1C, 2A-2C, 3A-3C, 4A-4B, 6A-6D, 7A-7F, 8A-8F, 9A-9F, 12, 14A-14F, 15A-15F, 17A-17F, 18A-18F, 19A-19F, 20A-20F, 25, 26, 27A-27B, 28A-28C, 30A-30B, 31A-31B and 32A-32D, a vehicle interior component C configured to administer a dose of ultraviolet light from a module M providing an ultraviolet light source directed to an object may comprise a base configured to provide the compartment; a cover CV moveable from a closed position to an open position providing access to the compartment; a user interface UI; and a platform PL for the object. The ultraviolet light source may be configured to administer the dose of ultraviolet light to the object in the compartment. The user interface may be configured for operation of the module. The platform may be configured to move with the cover between the closed position and the open position. The platform may be configured to position the object for access when the cover is in the open position; the platform may be configured to position the object for administration of the dose of ultraviolet light when the cover is in the closed position. The ultraviolet light source may comprise an upper light source and a lower light source separated from the upper light source by the platform; the platform may comprise a mesh MS configured to facilitate passage of light from the lower light source to the object. The ultraviolet light source may comprise a lamp installed within the base. The module may be mounted in the base. The user interface may comprise a control panel CP. The platform may comprise a shelf. The platform may comprise a first compartment for a first object and a second compartment for a second object. The component may comprise a harness/wire harness WH for the cover; the cover may comprise the user interface. The component may comprise a glove box. The base may be configured to be installed in/under an instrument panel. The component may comprise a control system for the module; the control system may be operated on a cycle intended to administer a dose of ultraviolet light to the object. The cover may comprise a door. The control system for the module may be operated by a method comprising the steps of (a) opening the door; (b) placing the object; (c) closing the door; (d) administering the dose of light to the object; (e) opening the door; and (f) removing the object. The object may comprise biomatter; the dose of ultraviolet light may be intended to sanitize the object of biomatter. The base may comprise the user interface; the cover may comprise at least one of (a) a light guide LG aligned with the user interface; and/or (b) a light pipe aligned with the user interface.

According to an exemplary embodiment as shown schematically in FIGS. 1C, 2A-2C, 3A-3C, 4A-4B, 6A-6D, 7A-7F, 8A-8F, 9A-9F, 12, 14A-14F, 15A-15F, 17A-17F, 18A-18F, 19A-19F, 20A-20F, 25, 26, 27A-27B, 28A-28C, 30A-30B, 31A-31B and 32A-32D, a vehicle interior component configured to administer a dose of ultraviolet light from a module providing an ultraviolet light source directed to an object may comprise a cover moveable from a closed position to an open position providing access to a compartment; a user interface UI; and a platform PL for the object. The ultraviolet light source may be configured to administer the dose of ultraviolet light to the object. The user interface may be configured for operation of the module. The platform may be configured to move with the cover between the closed position and the open position. The component may comprise a base configured to provide the compartment. The base may comprise a control panel CP for the user interface; the control panel may comprise an indicator light; the user interface may comprise a light transmissive light guide on the cover; the light guide may be aligned with the indicator light on the control panel when the cover is in the closed position. The base may comprise the user interface; the cover may comprise at least one of (a) a light guide LG aligned with the user interface; and/or (b) a light pipe aligned with the user interface. The ultraviolet light source may comprise at least one of (a) an LED; (b) an LED lamp; (c) an LED array; (d) at least one LED; (e) a set of two LEDs; (f) a lamp installed within the base; (g) a light emitting diode installed within the base; and/or (h) a UV-C LED installed within the base. The base may comprise the platform for the object. The ultraviolet light source may comprise a lamp installed within the base. The module may be mounted in the base. The base may be configured to be installed in/under an instrument panel. The component may comprise a control panel CP for the user interface; the control panel may comprise a button. The component may comprise a glove box; the cover may comprise a door for the glove box. The platform may be configured to position the object for access when the cover is in the open position; the platform may be configured to position the object for administration of the dose of ultraviolet light when the cover is in the closed position. The ultraviolet light source may comprise an upper light source and a lower light source separated from the upper light source by the platform; the platform may comprise a mesh MS configured to facilitate passage of light from the lower light source to the object. The user interface may comprise a control panel CP. The platform may comprise a shelf. The platform may comprise a first compartment for a first object and a second compartment for a second object. The component may comprise a harness for the cover; the cover may comprise the user interface. The component may comprise a glove box. The component may comprise a control system for the module; the control system may be operated on a cycle intended to administer a dose of ultraviolet light to the object. The cover may comprise a door. The control system for the module may be operated by a method comprising the steps of (a) opening the door; (b) placing the object; (c) closing the door; (d) administering the dose of light to the object; (e) opening the door; and (f) removing the object. The object may comprise biomatter; the dose of ultraviolet light may be intended to sanitize the object of biomatter.

Exemplary Embodiments—D

According to an exemplary embodiment as shown in FIGS. 1C, 2A-2C, 3A-3C, 4A-4B, 6A-6D, 7A-7F, 8A-8F, 9A-9F, 10A-10F, 11A-11B, 12, 13A-13F, 14A-14F, 15A-15F, 16A-16F, 17A-17F, 18A-18F, 19A-19F, 20A-20F, 25, 26, 27A-27B, 28A-28C, 30A-30B, 31A-31B and 32A-32D, a component for a vehicle interior configured to administer a dose of radiation to an object may comprise a base comprising a compartment for the object, a cover CV moveable relative to the base from a closed position to an open position providing access to the compartment, a module M comprising a radiation source and a user interface comprising a control panel for the module. The radiation source may be configured to administer the dose of radiation to the object in the compartment. The user interface may be configured to provide a signal comprising an audible signal and/or a light signal. The object may comprise biomatter; the dose of radiation may be intended to sanitize the object of biomatter. The component may comprise a sensor configured to detect whether the cover is in the closed position. The module may be configured to administer the dose of radiation only when the sensor detects that the cover is in the closed position. The component may comprise a sensor configured to detect whether the object is in the compartment. The control panel may comprise at least one of (a) an indicator light; (b) a speaker; and/or (c) a button. The control panel may be on the cover. The control panel may comprise a button BR adjacent to the cover. The control panel may be separate from the base. The control panel may comprise a remote button within the vehicle interior. The dose of radiation may be selected at the control panel. The component may comprise a control system for the module. The control system may be operated on a cycle intended to administer the dose of ultraviolet light to the object. The control system may be operable by a control program. The control program may be configured to provide a fault signal to stop operation of the radiation source when a fault condition is detected. A fault condition may be detected when at least one of (a) the object is not detected in the compartment; and/or (b) the cover is not detected in a closed position. The fault condition may be detected at a sensor. The compartment may be configured to contain the object; the radiation source may comprise an LED arrangement configured to direct light onto the object in the compartment. The radiation source may comprise an ultraviolet light source. The radiation source may comprise a light source LS; the light source may comprise at least one of (a) an LED; (b) an LED lamp; (c) an LED array; (d) at least one LED; (e) a set of two LEDs; (f) a lamp installed within the base; (g) a light emitting diode installed within the base; (h) a UV-C LED installed within the base; (i) an LED arrangement; and/or (j) an ultraviolet light source. The user interface may be configured for operation of the module; the user interface may comprise a light signal. The user interface may be presented by a light guide LG on the cover. The light guide may be aligned with an indicator light on the control panel when the cover is in the closed position. The compartment may comprise a removable bin for the object. The cover may comprise at least one of (a) a light guide aligned with the user interface; and/or (b) a light pipe aligned with the user interface. The cover may comprise a door; the control system for the module may be operated by a method comprising the steps of (a) opening the door; (b) placing the object; (c) closing the door; (d) administering the dose of light to the object; (e) opening the door; and (f) removing the object. The component may comprise a platform PL configured to position the object for access when the cover is in the open position; the dose of radiation may comprise a dose of ultraviolet light; the platform may be configured to position the object for administration of the dose of ultraviolet light when the cover is in the closed position. The radiation source may comprise an upper light source and a lower light source separated from the upper light source by the platform (see FIGS. 20A-20F); the platform may comprise a mesh MS configured to facilitate passage of light from the lower light source to the object. The base may comprise at least one of (a) a platform for the object; (b) a shelf for the object; and/or (c) a first compartment for a first object and a second compartment for a second object. The base may be configured to be installed in an instrument panel. The base may be configured to be installed under an instrument panel. The component may comprise a glove box; the cover may comprise a door for the glove box. The component may comprise at least one of (a) a storage compartment; (b) a console; and/or (c) a removable compartment.

According to an exemplary embodiment as shown in FIGS. 1C, 2A-2C, 3A-3C, 4A-4B, 6A-6D, 7A-7F, 8A-8F, 9A-9F, 10A-10F, 11A-11B, 12, 13A-13F, 14A-14F, 15A-15F, 16A-16F, 17A-17F, 18A-18F, 19A-19F, 20A-20F, 25, 26, 27A-27B, 28A-28C, 30A-30B, 31A-31B and 32A-32D, a system for a vehicle interior configured to administer a dose of radiation to an object may comprise a component comprising a base providing a compartment and a cover CV, a module M comprising a radiation source operated by a control program, and a control panel configured to provide a user interface in operation of the module. The user interface may comprise presentation of a signal; the compartment may be configured to contain the object; the cover may be configured to move between a closed position and an open position to allow access within the compartment; the radiation source may be configured to administer the dose of radiation to the object according to the control program. The radiation may comprise ultraviolet light; the radiation source may comprise an ultraviolet light source configured to administer the dose of ultraviolet light to the object. The user interface may be configured for operation of the module. The component may comprise a platform PL. The cover may be configured to be moved to the closed position for administration of the dose of radiation. The cover may be configured to be moved to the open position relative to the base providing access to the compartment. The compartment may comprise a bin BN; the radiation source may be configured to direct radiation into the bin. The control panel may comprise an indicator light; the user interface may comprise a light transmissive light guide on the cover; the light guide may be aligned with the indicator light on the control panel when the cover is in the closed position. The base may comprise the user interface; the cover may comprise at least one of (a) a light guide aligned with the user interface; and/or (b) a light pipe aligned with the user interface. The system may comprise a control system for the module; the control system may be operated according to the control program on a cycle intended to administer a dose of ultraviolet light to the object. The cover may comprise a door; the control system for the module may be operated by a method comprising the steps of (a) opening the door; (b) placing the object; (c) closing the door; (d) administering the dose of light to the object; (e) opening the door; and (f) removing the object. The signal of the user interface may comprise at least one of a light signal and/or an audible signal. The light signal may be provided at the control panel. The audible signal may be provided at the control panel. The control panel may comprise an operator control configured to operate the module of the component; the operator control may be configured to select an operation cycle for the module. The signal may comprise a completion signal. The signal may comprise at least one of (a) a fault signal; and/or (b) an interrupt signal for the module. The signal may be provided by at least one of (a) an indicator; (b) a sound transmitter; (c) a light; and/or (d) light-transmissive elements to provide illumination. The radiation source may comprise an LED arrangement configured to provide at least 100 mW of LED light. The LED light may comprise a wavelength of about 275 nm. The LED arrangement may comprise two LED lights; each LED light of the two LED lights may comprise an LED configured to provide at least 100 mA total UVC energy. The control program may be configured to operate the module with an operation cycle comprising a cycle time of between 15 seconds and 120 seconds. The compartment may be configured to place the object at about 15 cm from the radiation source. The radiation source may be configured to provide at least a 3 log reduction in virus/bacteria on the object. The radiation source may be configured to provide at least a 99 percent reduction in active biomatter on the object. The module may be configured to provide 100 mA of UVC power; the control program may be configured to operate the module with an operation cycle comprising a cycle time of about 120 seconds. The control panel may comprise an override switch. The component may comprise a glovebox comprising a switch SW configured to turn off the radiation source. (See e.g. FIGS. 5A-5B and 6A-6D.) The cover may comprise a door for the glove box and the control program may be configured to turn off the radiation source if the switch detects that the door is open. The control panel may comprise a push button to activate the module. The control panel may comprise a remote button to activate the module. The signal from the user interface may be configured to indicate of status of operation of the module. The signal may comprise a blinking light when in operation during administration of the dose of radiation and a solid light when the dose of radiation is completed. The signal may comprise a light that is off when the module is not in operation. The signal may comprise a sound during administration of the dose of radiation. The signal may comprise a sound to indicate completion of administration of the dose of radiation. The signal may comprise an alert in a fault condition. The signal may comprise an audible tone at an interval during administration of radiation. The signal may comprise a pattern comprising a tone at an interval when in operation and a tone when completed. The component may comprise at least one of a storage compartment; a glove box; a console; a floor console; an overhead console; a trim panel; and/or a door panel. The system may be operated according to a method comprising the steps of setting a cycle of operation of the system, initiating the cycle of operation of the system, monitoring the system in operation and providing the signal at the user interface. Monitoring the system in operation may comprise determining status of the system; operation of the system may comprise at least one of applying the dose of radiation to the object or ending the cycle if a fault is detected. The signal may be provided to indicate status of the system. The signal may comprise at least one of (a) a completion signal when the cycle of operation is completed; (b) an operation signal during operation of the system; and/or (c) a fault signal if the cycle of operation is not completed. The component may comprise a sensor to indicate status, and monitoring the system in operation may comprise monitoring status indicated by the sensor. Status of the system may comprise at least one of (a) presence of the object in the compartment; and/or (b) status of the cover. The cover may comprise a door movable from an open position to a closed position; status of the system may comprise detection of whether the door is in the open position of the door. When the door is in the open position of the door, the step of monitoring the system in operation may comprise indicating a fault status and providing a fault signal.

According to an exemplary embodiment as shown in FIGS. 1C, 2A-2C, 3A-3C, 4A-4B, 11A-11B, 12, 13A-13F, 14A-14F, 15A-15F, 16A-16F, 17A-17F, 18A-18F, 19A-19F, 20A-20F, 25, 26, 27A-27B, 31A-31B and 32A-32D, a vehicle interior component configured to administer a dose of ultraviolet light from a module M providing an ultraviolet light source directed to an object may comprise a base, a tray PL coupled to the base and comprising a compartment, and a user interface. The ultraviolet light source may be configured to administer the dose of ultraviolet light to the object in the compartment; the user interface may be configured for operation of the module; the tray may be configured to move relative to the base from a retracted position for administration of the dose of ultraviolet light to an extended position for access (See FIGS. 13C, 14C, 15C, 16C, 17C, 18C, 19C and 20C). The component may comprise a mechanism configured to (a) retain the tray in the retracted position (b) guide movement of the tray from the retracted position to the extended position. The mechanism may be configured to move the tray from the retracted position to the extended position after administration of the dose of ultraviolet light. The mechanism may comprise (a) a latch LP configured to retain the tray in the retracted position and (b) an actuator configured to unlatch the tray after administration of the dose of ultraviolet light. The mechanism may comprise a motor configured to move the tray between the retracted position and the extended position; the motor may be configured to move the tray from the retracted position to the extended position after administration of the dose of ultraviolet light. The ultraviolet light source may comprise an upper lamp and a lower lamp separated from the upper lamp by the tray. The component may comprise a bin BN coupled to the base comprising a receptacle into which an article can be stowed and configured to move relative to the base in an opening direction from a closed position to an open position for access; the ultraviolet light source may be configured to administer a dose of ultraviolet light to the article in the receptacle. The component may comprise (a) a cover CV configured to cover the tray and the bin and (b) a mechanism; the mechanism may be configured to guide movement of the cover and the bin. The tray may be configured to move between the retracted position and the extended position when the bin is in the closed position and the open position. The component may comprise a button BR; the mechanism may be configured to move the cover and the tray in response to actuation of the button. The component may comprise a control system for the module; the control system for the module may be operated by a method comprising the steps of (a) extending the tray, (b) placing the object, (c) retracting the tray, (d) administering the dose of light to the object, (e) extending the tray, and (f) removing the object.

According to an exemplary embodiment as shown in FIGS. 1C, 2A-2C, 3A-3C, 4A-4B, 11A-11B, 12, 13A-13F, 14A-14F, 15A-15F, 16A-16F, 17A-17F, 18A-18F, 25, 26, 27A-27B, 31A-31B and 32A-32D, a component for a vehicle interior configured to stow an article may comprise a base, a bin BN coupled to the base comprising a receptacle into which the article can be stowed and configured to move relative to the base in an opening direction from a closed position to an open position for access, a tray PL coupled to the base and configured to move relative to the base from a retracted position to an intermediate position for access (See FIGS. 13C, 14C, 15C, 16C, 17C, 18C, 19C and 20C), a cover CV coupled to the base configured to move from an upward position to cover the tray to a lowered position (See FIGS. 13B, 14B, 15B, 16B, 17B and 18B) to uncover the tray and a module M coupled to the base providing an ultraviolet light source configured to administer a dose of ultraviolet light to the article. The bin may be configured to move relative to the base from the closed position to the open position when the tray is in the retracted position and the intermediate position. The tray may be configured to move from the retracted position to the intermediate position when the bin is in the closed position and the open position. The tray may be configured to move relative to the base from the intermediate position to an extended position. The tray may be configured to move from the intermediate position to the extended position when the bin is in the closed position and the open position. The component may comprise a mechanism configured to (a) latch the tray to the base in the retracted position and (b) unlatch the tray from the base. The component may comprise a mechanism configured to (a) retain the bin in the closed position (b) guide movement of the bin from the closed position to the open position and (c) guide movement of the cover from the upward position to the lowered position. The component may comprise a mechanism configured to (a) retain the tray in the retracted position and (b) move the tray from the retracted position to the intermediate position. The component may comprise a mechanism configured to (a) retain the tray in the retracted position and (b) guide movement of the tray from the retracted position to the intermediate position. The mechanism may be configured to move the tray from the retracted position to the intermediate position after administration of the dose of ultraviolet light. The component may comprise a user interface configured for operation of the module; at least one of (a) the base; and/or (b) the tray may comprise the user interface; the cover may comprise a light guide LG aligned with the user interface.

According to an exemplary embodiment as shown in FIGS. 1C, 2A-2C, 3A-3C, 4A-4B, 7A-7F, 8A-8F, 25, 26, 27B, 31A-31B and 32A-32D, a vehicle interior component configured to administer a dose of ultraviolet light from a module M providing an ultraviolet light source directed to an object may comprise a base configured to provide a compartment, a cover CV moveable from a closed position to an open position providing access to the compartment, a user interface and a platform PL for the object. The ultraviolet light source may be configured to administer the dose of ultraviolet light to the object in the compartment; the user interface may be configured for operation of the module; the platform may be configured to move with the cover between the closed position and the open position (See FIGS. 7C and 8C). The platform may be configured to position the object for access when the cover is in the open position; the platform may be configured to position the object for administration of the dose of ultraviolet light when the cover is in the closed position. The ultraviolet light source may comprise an upper light source and a lower light source separated from the upper light source by the platform; the platform may comprise a mesh MS configured to facilitate passage of light from the lower light source to the object. The cover may comprise a door; the control system for the module may be operated by a method comprising the steps of (a) opening the door, (b) placing the object, (c) closing the door, (d) administering the dose of light to the object, (e) opening the door, and (f) removing the object.

According to an exemplary embodiment as shown in FIGS. 1C, 2A-2C, 3A-3C, 4A-4B, 7A-7F, 8A-8F, 25, 26, 27B, 31A-31B and 32A-32D, a vehicle interior component configured to administer a dose of ultraviolet light from a module M providing an ultraviolet light source directed to an object may comprise a cover CV moveable from a closed position to an open position providing access to a compartment, a user interface and a platform PL for the object. The ultraviolet light source may be configured to administer the dose of ultraviolet light to the object; the user interface may be configured for operation of the module; the platform may be configured to move with the cover between the closed position and the open position. The platform may be configured to position the object for access when the cover is in the open position; the platform may be configured to position the object for administration of the dose of ultraviolet light when the cover is in the closed position. The cover may comprise a door; the control system for the module may be operated by a method comprising the steps of (a) opening the door, (b) placing the object, (c) closing the door, (d) administering the dose of light to the object, (e) opening the door, and (f) removing the object.

It is important to note that the present inventions (e.g. inventive concepts, etc.) have been described in the specification and/or illustrated in the FIGURES of the present patent document according to exemplary embodiments; the embodiments of the present inventions are presented by way of example only and are not intended as a limitation on the scope of the present inventions. The construction and/or arrangement of the elements of the inventive concepts embodied in the present inventions as described in the specification and/or illustrated in the FIGURES is illustrative only. Although exemplary embodiments of the present inventions have been described in detail in the present patent document, a person of ordinary skill in the art will readily appreciate that equivalents, modifications, variations, etc. of the subject matter of the exemplary embodiments and alternative embodiments are possible and contemplated as being within the scope of the present inventions; all such subject matter (e.g. modifications, variations, embodiments, combinations, equivalents, etc.) is intended to be included within the scope of the present inventions. It should also be noted that various/other modifications, variations, substitutions, equivalents, changes, omissions, etc. may be made in the configuration and/or arrangement of the exemplary embodiments (e.g. in concept, design, structure, apparatus, form, assembly, construction, means, function, system, process/method, steps, sequence of process/method steps, operation, operating conditions, performance, materials, composition, combination, etc.) without departing from the scope of the present inventions; all such subject matter (e.g. modifications, variations, embodiments, combinations, equivalents, etc.) is intended to be included within the scope of the present inventions. The scope of the present inventions is not intended to be limited to the subject matter (e.g. details, structure, functions, materials, acts, steps, sequence, system, result, etc.) described in the specification and/or illustrated in the FIGURES of the present patent document. It is contemplated that the claims of the present patent document will be construed properly to cover the complete scope of the subject matter of the present inventions (e.g. including any and all such modifications, variations, embodiments, combinations, equivalents, etc.); it is to be understood that the terminology used in the present patent document is for the purpose of providing a description of the subject matter of the exemplary embodiments rather than as a limitation on the scope of the present inventions.

It is also important to note that according to exemplary embodiments the present inventions may comprise conventional technology (e.g. as implemented and/or integrated in exemplary embodiments, modifications, variations, combinations, equivalents, etc.) or may comprise any other applicable technology (present and/or future) with suitability and/or capability to perform the functions and processes/operations described in the specification and/or illustrated in the FIGURES. All such technology (e.g. as implemented in embodiments, modifications, variations, combinations, equivalents, etc.) is considered to be within the scope of the present inventions of the present patent document.

What is claimed is:

1. A component for a vehicle interior configured to administer a dose of radiation to an object comprising:
    (a) a base comprising a compartment for the object;
    (b) a cover moveable relative to the base from a closed position to an open position providing access to the compartment;
    (c) a module comprising a radiation source; and
    (d) a user interface comprising a control panel for the module;
    wherein the radiation source is configured to administer the dose of radiation to the object in the compartment;
    wherein the user interface is configured to provide a signal comprising an audible signal and/or a light signal; and
    wherein the user interface is provided by a light guide on the cover.

2. The component of claim 1 wherein the object comprises biomatter; wherein the dose of radiation is intended to sanitize the object of biomatter.

3. The component of claim 1 further comprising a sensor configured to detect whether the object is in the compartment.

4. The component of claim 1 wherein the compartment is configured to contain the object; wherein the radiation source comprises an LED arrangement configured to direct light onto the object in the compartment.

5. The component of claim 1 wherein the radiation source comprises a light source; wherein the light source comprises at least one of (a) an LED; (b) an LED lamp; (c) an LED array; (d) at least one LED; (e) a set of two LEDs; (f) a lamp installed within the base; (g) a light emitting diode installed within the base; (h) a UV-C LED installed within the base; (i) an LED arrangement; and/or (j) an ultraviolet light source.

6. The component of claim 1 wherein the light guide comprises at least one of (a) a light guide aligned with the user interface; and/or (b) a light pipe aligned with the user interface.

7. The component of claim 1 wherein the compartment comprises a bin; wherein the radiation source is configured to direct radiation into the bin.

8. The component of claim 1 further comprising a control system for the module; wherein the control system is operated according to control program on a cycle intended to administer a dose of ultraviolet light to the object.

9. The component of claim 8 wherein the cover comprises a door; wherein the control system for the module is operated by a method comprising the steps of (a) opening the door; (b) placing the object; (c) closing the door; (d) administering the dose of light to the object; (e) opening the door; and (f) removing the object.

10. The component of claim 1 wherein the signal comprises at least one of (a) a completion signal or (b) a fault signal or (c) an interrupt signal for the module.

11. The component of claim 1 wherein the signal is provided by at least one of (a) an indicator; (b) a sound transmitter; (c) a light; and/or (d) light-transmissive elements to provide illumination.

12. The component of claim 1 wherein the cover comprises a door for a glove box and a control program is configured to turn off the radiation source if a switch detects that the door is open.

13. The component of claim 1 wherein the light signal comprises at least one of (a) a blinking light when in operation during administration of the dose of radiation or (b) a solid light when the dose of radiation is completed or (c) a light that is off when the module is not in operation.

14. The component of claim 1 wherein the signal comprises at least one of (a) a sound during administration of the dose of radiation; (b) a sound to indicate completion of administration of the dose of radiation; (c) an alert in a fault condition; (d) an audible tone at an interval during administration of radiation; and/or (e) a pattern comprising a tone at an interval when in operation and a tone when completed.

15. The component of claim 1 further comprising a tray coupled to the base and configured to move between a retracted position and an extended position.

16. The component of claim 1 wherein the component comprises at least one of a storage compartment; a glove box; a console; a floor console; an overhead console; and/or a removable compartment.

17. The component of claim 1 wherein the light guide is aligned with an indicator light on the control panel when the cover is in the closed position.

18. The component of claim 1 further comprising a platform configured to position the object for access when the cover is in the open position; wherein the dose of radiation comprises a dose of ultraviolet light; wherein the platform is configured to position the object for administration of the dose of ultraviolet light when the cover is in the closed position.

19. The component of claim 18 wherein the radiation source comprises an upper light source and a lower light source separated from the upper light source by the platform; wherein the platform comprises a mesh configured to facilitate passage of light from the lower light source to the object.

* * * * *